(12) United States Patent
Lim et al.

(10) Patent No.: US 11,827,920 B2
(45) Date of Patent: Nov. 28, 2023

(54) NANOSTRUCTURE, A BIOSENSOR INCLUDING THE NANOSTRUCTURE, AND A SCREENING METHOD

(71) Applicant: POSTECH Research and Business Development Foundation, Pohang-si (KR)

(72) Inventors: Hyun-Suk Lim, Pohang-si (KR); Kang Ju Lee, Pohang-si (KR)

(73) Assignee: POSTECH RESEARCH AND BUSINESS DEVELOPMENT FOUNDATION, Gyeongsangbuk-Do (KR)

( * ) Notice: Subject to any disclaimer, the term of this patent is extended or adjusted under 35 U.S.C. 154(b) by 155 days.

(21) Appl. No.: 16/803,731

(22) Filed: Feb. 27, 2020

(65) Prior Publication Data

US 2021/0262014 A1    Aug. 26, 2021

(30) Foreign Application Priority Data

Feb. 26, 2020    (KR) ......................... 10-2020-0023925

(51) Int. Cl.
| | |
|---|---|
| *B82Y 5/00* | (2011.01) |
| *B82Y 15/00* | (2011.01) |
| *C12Q 1/6825* | (2018.01) |
| *C12Q 1/686* | (2018.01) |
| *C12Q 1/6869* | (2018.01) |
| *C12Q 1/6876* | (2018.01) |

(52) U.S. Cl.
CPC .......... *C12Q 1/6825* (2013.01); *C12Q 1/686* (2013.01); *C12Q 1/6869* (2013.01); *C12Q 1/6876* (2013.01); *B82Y 5/00* (2013.01); *B82Y 15/00* (2013.01); *C12Q 2563/155* (2013.01)

(58) Field of Classification Search
CPC ............... C12Q 1/6825; C12Q 1/6876; C12Q 2563/155; B82Y 5/00; B82Y 15/00
See application file for complete search history.

(56) References Cited

U.S. PATENT DOCUMENTS

| 5,639,603 A * | 6/1997 | Dower ................... C07H 19/10 506/28 |
|---|---|---|
| 8,642,514 B2 | 3/2014 | Neri et al. |
| 8,673,824 B2 | 3/2014 | Neri et al. |
| 9,359,601 B2 | 6/2016 | Wagner |
| 9,783,843 B2 | 10/2017 | Neri et al. |
| 2016/0369267 A1 | 12/2016 | Wagner |
| 2017/0003288 A1 | 1/2017 | Heath et al. |
| 2018/0245141 A1 | 8/2018 | Neri et al. |

FOREIGN PATENT DOCUMENTS

| KR | 100916889 A | 9/2009 |
|---|---|---|
| KR | 1020100123794 A | 11/2010 |
| KR | 20110036638 A | 4/2011 |
| KR | 20170040080 A | 4/2017 |
| KR | 101789216 A | 10/2017 |
| KR | 20190035613 A | 4/2019 |
| WO | WO-2017192633 A1 * | 11/2017 ........... C12Q 1/6869 |

OTHER PUBLICATIONS

Patel et al. Proceedings of the National Academy of Sciences, USA 2008; 105: 17222-17226. (Year: 2008).*
Christian Heinis, et al., Phage-encoded combinatorial chemical libraries based on bicyclic peptides, vol. 5, No. 7, Jul. 2009, Nature Chemical Biologyarticles, 7 pp.
Dmitry L. Usanov, et al., Second-Generation DNA-Templated Macrocycle Libraries for the Discovery of Bioactive Small Molecules, Author Manuscript, Published in final edited form as: Nat Chem. Jul. 2018; 10(7): 704-714. 23 pp.
Finny G Kuruvilla, et al., Dissecting glucose signalling withdiversity-oriented synthesis and small-molecule microarrays, Nature | vol. 416 | Apr. 11, 2002 | www.nature.com, 5 pp.
Ganesh A. Sable, et al., Solid-Phase Synthesis and Circular Dichroism Study of B-ABpeptoids, Molecules 2019, 24, 178; doi:10.3390/molecules24010178, 13 pp.
Hee-Jo Moon, et al., Design, Solid-Phase Synthesis, and Evaluation of a Phenyl-Piperazine-Triazine Scaffold as #-Helix Mimetics, ACS Comb. Sci., Just Accepted Manuscript • DOI: 10.1021/co500114f • Publication Date (Web): Oct. 21, 2014, 20 pp.
Hiroshi Murakami, et al., A highly flexible tRNAacylation method for non-natural polypeptide synthesis, Nature Methods | vol. 3 No. 5 | May 2006 | 357-359.
Ji Hoon Lee, et al., A simple strategy for the construction of combinatorial cyclic peptoid libraries, Chem Commun., 2010, 46, 8615-1617.

(Continued)

*Primary Examiner* — Angela M. Bertagna
(74) *Attorney, Agent, or Firm* — CANTOR COLBURN LLP

(57) ABSTRACT

Disclosed are a nanostructure including a nanoparticle, and a first compound including a probe and bound to the surface of the nanoparticle, a second compound including a DNA sequence encoding the probe and bound to the surface of the nanoparticle, and optionally substituted or unsubstituted polyalkylene glycol bound to the surface of the nanoparticle, wherein when the nanostructure does not include substituted or unsubstituted polyalkylene glycol bound to the surface of the nanoparticle, a ratio $((n^1+n^2)/w)$ of the sum of the number of moles $(n^1)$ of the first compound and the number of moles $(n^2)$ of the second compound relative to the weight (w) of the nanostructure is about 1.2 nmol/g to about 85 μmol/g on average, a biosensor including the nanostructure, and a method of screening a biological material using the nanostructure or the biosensor.

12 Claims, 32 Drawing Sheets

Specification includes a Sequence Listing.

(56) References Cited

OTHER PUBLICATIONS

Ji Hoon Lee, et al., Converting One-Face #-Helix Mimetics into Amphiphilic #-Helix Mimetics as Potent Inhibitors of Protein-Protein Interactions, ACS Publications, Dec. 18, 2015, 19 pp.

Ji Hoon Lee, et al., Design and Facile Solid-Phase Synthesis of Conformationally Constrained Bicyclic Peptides, American Chemical Society, 2011, 4 pp.

Ji Hoon Lee, et al., Novel Pyrrolopyrimidine-Based R-Helix Mimetics: Cell-Permeable Inhibitors of Protein-Protein Interactions, J. Am. Chem. Soc. 2011, 133, 676-679.

Ji Hoon Lee, et al., Solid-phase synthesis of tetrasubstituted pyrrolo[2,3-d]pyrimidines, The Royal Society of Chemistry, Org. Biomol. Chem., 2012, 10, 4229-4235.

John McCafferty, et al., Phage antibodies: filamentous phage displaying antibody variable domains, Nature: vol. 348, Dec. 6, 1990, 3 pp.

John P. Overington, et al., How many drug targets are there?, Nature Reviews, Perspectives, Dec. 2006, 993-996.

Kang Ju Lee, et al., Facile Method to Sequence Cyclic Peptides/Peptoids via One-Pot Ring-Opening/Cleavage Reaction, American Chemical Society, Org. Lett. 2014, 16, 5710-5713.

Kit S. Lam, et al., A new type of synthetic peptide library for identifying ligand-binding activity, Nature, vol. 354, Nov. 7, 1991, 3 pp.

L. K. Petersen, et al., Novel p38α MAP kinase inhibitors identified from yoctoReactor DNA-encoded small molecule library, Med. Chem. Commun., 2016, 7, 1332-1339.

Min-Kyung Shin, et al., Comparison of Cell Permeability of Cyclic Peptoids and Linear Peptoids, American Chemical Society, Published Feb. 26, 2018, 6 pp.

Misook Oh, et al., A Chemical Inhibitor of the Skp2/p300 Interaction that Promotes p53-Mediated Apoptosis, Angew. Chem. Int. Ed. 2016, 55, 602-606.

Misook Oh, et al., Potential pharmacological chaperones targeting cancer-associated MCL-1 and Parkinson disease-associated α-synuclein, PNAS, Jul. 29, 2014, vol. 111, No. 30, 11007-11012.

Rita Santos, et al., A comprehensive map of molecular drug targets, Nature Reviews | Drug Discovery, Advance Online Publication, 16 pp., publication date = Dec. 2, 2016.

Robert K. Y. Cheng, Structural insight into allosteric modulation of protease-activated receptor 2, Nature, vol. 000, 2017, 15 pp.

Samu Melkko, et al., Encoded self-assembling chemical libraries, vol. 22, No. 5, May 2004, Nature Biotechnology, 8 pp.

Seungkirl Ahn, et al., Allosteric "beta-blocker" isolated from a DNA-encoded small molecule library, PNAS, Feb. 14, 2017, vol. 114, No. 7, 1708-1713.

Yizhou Li, et al., Versatile protein recognition by the encoded display of multiple chemical elements on a constant macrocyclic scaffold, Nature Chemistry | www.nature.com/naturechemistry, 2018, 10, 441, 11 pp.

Zev J. Gartner, et al., DNA-Templated Organic Synthesis and Selection of a Library of Macrocycles, www.sciencemag.org, Science, vol. 305, Sep. 10, 2004, 6 pp.

Christina Nadolny, et al., Liver receptor homolog-1 (LRH-1): a potential therapeutic target for cancer, Cancer Biology & Therapy 16:7, 997-1004; Jul. 2015.

Cindy Benod, et al., Nuclear receptor liver receptor homologue 1 (LRH-1) regulates pancreatic cancer cell growth and proliferation, PNAS | Oct. 11, 2011 | vol. 108 | No. 41 | 16927-16931.

Claudio Zambaldo, et al., PNA-encoded chemical libraries, Current Opinion in Chemical Biology 2015, 26:8-15.

Ganesh A. Sable, et al., Submonomer Strategy toward Divergent Solid-Phase Synthesis of α-ABpeptoids, Feb. 25, 2018, American Chemical Society, 4 pp.

J. P. Daguer, et al. Chem. Sci., 2011, 2, 625-632.

James A. Wells, et al., Reaching for high-hanging fruit in drug discovery at protein-protein interfaces, Nature, vol. 450, Dec. 13, 2007, 1001-1009.

James R. Bayrer, et al., Silencing LRH-1 in colon cancer cell lines impairs proliferation and alters gene expression programs, PNAS, Feb. 24, 2015, vol. 112, No. 8, 2467-2472.

Kang Ju Lee, et al., Oligomers of N-Substituted β2-Homoalanines: Peptoids with Backbone Chirality, American Chemical Society, Jun. 14, 2016, 4 pp.

Loren D. Walensky, et al., Hydrocarbon-Stapled Peptides: Principles, Practice, and Progress, 2014 American Chemical Society, 57, 6275-6288.

M. Oh, et al. Angew. Chem. Int. Ed. 2016, 55, 602-606.

Markus Seitz, et al., Molecular Characterization of the NCoA-1-STAT6 Interaction, ChemBioChem 2008, 9, 1318-1322.

Matthew Clark, et al., Design, synthesis and selection of DNA-encoded small-molecule libraries, Nat. Chem. Biol. 2009, 5, 647-654.

Raheleh Rezaei Araghi, et al., Rapid Optimization of Mcl-1 Inhibitors using Stapled Peptide Libraries Including Non-Natural Side Chains, ACS Chem. Biol. 2016, 11, 1238-1244.

Rong-jun He, et al., Protein tyrosine phosphatases as potential therapeutic targets, Acta Pharmacologica Sinica (2014) 35: 1227-1246.

S Bianco, et al., LRH-1 controls proliferation in breast tumor cells by regulating CDKN1A gene expressionOncogene, (2015) 34, 4509-4518.

Theodore O. Johnson, et al., Protein Tyrosine Phosphatase 1B Inhibitors for Diabetes, Nature Publishing Group, Sep. 2002, vol. 1, 696-709.

Yeongju Lee, et al., Targeted Inhibition of the NCOA1/STAT6 Protein-Protein Interaction, J. Am. Chem. Soc., 2017, 4 pp.

Young-Woo Kim, et al., Synthesis of all-hydrocarbon stapled a-helical peptides by ring-closing olefin metathesis, nature protocols, vol. 6 No. 6, 2011, 761-771.

Yu Heng Lau, et al., Peptide stapling techniques based on different macrocyclisation chemistries, Chem. Soc. Rev., 2014, 12 pp.

Zev J. Gartner et al., DNA-Templated Organic Synthesis and Selection of a Library of Macrocycles, Science 2004, 305, 1601-1605.

* cited by examiner

| Rank | R1 | R2 | R3 | R4 | R5 | R6 | Stapling site | Count | | |
|---|---|---|---|---|---|---|---|---|---|---|
| 1 | Ser | Nle | Arg | Nle | Ser | Phe² | C1 | 22865 | (SEQ ID NO: 75) | Hit 1 |
| 2 | Nap | Ile | ²Arg | Leu | Arg | Phe | C2 | 19361 | (SEQ ID NO: 76) | |
| 3 | Gln | Val | Arg | Phe² | Arg | Nap | C2 | 15146 | (SEQ ID NO: 77) | |
| 4 | Tyr | Nle | Arg | Cha | ²Arg | Trp | C1 | 10929 | (SEQ ID NO: 78) | Hit 2 |
| 5 | Nap | Leu | Nap | Ile | Trp | Tyr | C2 | 10373 | (SEQ ID NO: 79) | |
| 6 | Trp | Nle | Phe²ᶜ | Phe² | Ala | Ile | C1 | 10217 | (SEQ ID NO: 80) | |
| 7 | Gln | Nap | Trp | Val | Arg | Leu | C2 | 9756 | (SEQ ID NO: 81) | |
| 8 | Ala | Ile | Phe²ᶜ | Ile | Arg | Nle | C2 | 8033 | (SEQ ID NO: 82) | |
| 9 | Ser | Phe² | ²Arg | Nle | ²Arg | Phe² | C2 | 7884 | (SEQ ID NO: 83) | Hit 3 |
| 10 | Arg | Tyr | Arg | Tyr | Trp | Thr | C3 | 8650 | (SEQ ID NO: 84) | |
| 11 | Tyr | Val | Arg | Tyr | Arg | Gln | C1 | 6244 | (SEQ ID NO: 85) | |
| 12 | Ala | Nle | Arg | Nap | Ser | Phe² | C1 | 6205 | (SEQ ID NO: 86) | Hit 4 |
| 13 | Nap | Cha | Ala | Phe² | Arg | ²Arg | C1 | 6194 | (SEQ ID NO: 87) | |
| 14 | Ala | Tyr | Tyr | Phe²ᶜ | Nap | Cha | C1 | 6088 | (SEQ ID NO: 88) | Hit 5 |
| 15 | Ala | Nap | Phe | Leu | Ile | Trp | C2 | 6063 | (SEQ ID NO: 89) | |
| 16 | Gln | Ile | ²Arg | Ile | Ala | Ala | C2 | 5919 | (SEQ ID NO: 90) | |
| 17 | Cha | Phe² | ²Arg | Phe² | Gln | Cha | C2 | 5882 | (SEQ ID NO: 91) | |
| 18 | Ile | Val | Nap | Leu | Nap | Ala | C2 | 5828 | (SEQ ID NO: 92) | |
| 19 | Arg | Leu | Phe | Phe | Nle | Cha | C1 | 5791 | (SEQ ID NO: 93) | |
| 20 | Ser | Leu | Phe² | Cha | Nap | Phe² | C1 | 5706 | (SEQ ID NO: 94) | |
| 21 | Tyr | Cha | Tyr | Val | Ser | Phe²ᶜ | C2 | 5701 | (SEQ ID NO: 95) | |
| 22 | Ser | Nle | ²Arg | Ile | Ala | Leu | C1 | 5668 | (SEQ ID NO: 96) | |
| 23 | Ile | Tyr | Phe² | Leu | Phe² | Thr | C2 | 5619 | (SEQ ID NO: 97) | |
| 24 | Phe | Tyr | Phe² | Phe² | Nle | Tyr | C1 | 5547 | (SEQ ID NO: 98) | |
| 25 | Cha | Tyr | Arg | Ile | Leu | Cha | C2 | 5498 | (SEQ ID NO: 99) | |
| 26 | Leu | Phe²ᶜ | Phe² | Ile | ²Arg | Ala | C1 | 5446 | (SEQ ID NO: 100) | |
| 27 | Ser | Leu | Arg | Tyr | Ala | Ala | C1 | 5410 | (SEQ ID NO: 101) | |
| 28 | Ile | Tyr | Arg | Trp | Nle | Trp | C2 | 5409 | (SEQ ID NO: 102) | |
| 29 | ²Arg | Phe² | Nap | Tyr | ²Arg | Trp | C2 | 5378 | (SEQ ID NO: 103) | |
| 30 | Ala | Nap | Arg | ²Phe | Leu | Trp | C2 | 5369 | (SEQ ID NO: 104) | |

FIG. 24D

| Rank | R1 | R2 | R3 | R4 | R5 | R6 | Stapling site | Count | |
|---|---|---|---|---|---|---|---|---|---|
| 1 | Tyr | Nle | Arg | Nle | Trp | ʸArg | C1 | 46771 | (SEQ ID NO: 105) Hit 3 |
| 2 | ʸArg | Tyr | Pheᶜ⁵ | ʸPhe | Trp | ʸArg | C2 | 21690 | (SEQ ID NO: 106) |
| 3 | Thr | Nle | Trp | Pheᶜ⁵ | Ser | Leu | C1 | 21766 | (SEQ ID NO: 107) |
| 4 | ʸArg | Pheᶜ⁵ | Pheᶜ⁵ | Nap | Ile | Cha | C1 | 21507 | (SEQ ID NO: 108) |
| 5 | Tyr | Ile | Pheᶜ⁵ | Nle | Ala | Ala | C1 | 21308 | (SEQ ID NO: 109) Hit 6 |
| 6 | Trp | Leu | Tyr | Pheᶜ⁵ | Ala | Ser | C2 | 21247 | (SEQ ID NO: 110) |
| 7 | Gln | Nle | Pheᶜ⁵ | Pheᶜ⁵ | Gln | Pheᶜ⁵ | C1 | 19779 | (SEQ ID NO: 111) |
| 8 | Phe | Ile | Arg | Nap | Ala | Thr | C1 | 17141 | (SEQ ID NO: 112) |
| 9 | Ser | Cha | Trp | Leu | Ile | Nle | C2 | 16697 | (SEQ ID NO: 113) |
| 10 | Ile | Nle | Phe | Leu | Trp | Arg | C1 | 14544 | (SEQ ID NO: 114) |
| 11 | Tyr | Val | Nap | Pheᶜ⁵ | Gly | Trp | C1 | 14341 | (SEQ ID NO: 115) |
| 12 | Arg | Nle | Pheᶜ⁵ | Phe | Trp | Arg | C1 | 13960 | (SEQ ID NO: 116) |
| 13 | Ile | Nle | Trp | Cha | Ala | Nap | C2 | 13894 | (SEQ ID NO: 117) |
| 14 | Ile | Nle | Nap | Leu | Ile | Ala | C1 | 12735 | (SEQ ID NO: 118) |
| 15 | Ala | Nle | Trp | Ala | Nle | Trp | C2 | 12552 | (SEQ ID NO: 119) |
| 16 | Ala | Nle | Pheᶜ⁵ | Ile | Phe | Ser | C2 | 12337 | (SEQ ID NO: 120) |
| 17 | Ile | Tyr | Tyr | Ile | Cha | ʸArg | C1 | 12313 | (SEQ ID NO: 121) |
| 18 | Arg | Pheᶜ⁵ | Pheᴺᵒᶜ⁵ | Pheᶜ⁵ | Arg | Gln | C2 | 12270 | (SEQ ID NO: 122) |
| 19 | Arg | Val | Tyr | Ile | Ser | Nle | C1 | 11962 | (SEQ ID NO: 123) |
| 20 | Ala | Pheᶜ⁵ | Pheᶜ⁵ | Ile | Thr | ʸArg | C2 | 11900 | (SEQ ID NO: 124) |
| 21 | Trp | Tyr | Arg | Pheᶜ⁵ | Nle | Pheᶜ⁵ | C1 | 11749 | (SEQ ID NO: 125) |
| 22 | Ala | Trp | Phe | Nle | Ala | ʸArg | C1 | 11743 | (SEQ ID NO: 126) |
| 23 | Tyr | Ile | ʸArg | Tyr | Gln | ʸArg | C1 | 11676 | (SEQ ID NO: 127) |
| 24 | Phe | Nle | Arg | Pheᶜ⁵ | Gln | Trp | C1 | 11540 | (SEQ ID NO: 128) Hit 7 |
| 25 | Ser | Nle | Pheᴺᵒᶜ⁵ | Trp | Ala | Nle | C2 | 11509 | (SEQ ID NO: 129) |
| 26 | Ile | Nap | Tyr | Phe | Nap | Ile | C2 | 11496 | (SEQ ID NO: 130) |
| 27 | Leu | Tyr | Tyr | Pheᶜ⁵ | Tyr | Gln | C1 | 11469 | (SEQ ID NO: 131) |
| 28 | Phe | Ile | Trp | Phe | ʸArg | Nle | C1 | 11324 | (SEQ ID NO: 132) |
| 29 | Gln | Cha | Arg | Tyr | Trp | Arg | C2 | 11293 | (SEQ ID NO: 133) |
| 30 | Nap | Val | Tyr | Ile | Phe | Thr | C1 | 11291 | (SEQ ID NO: 134) |

FIG. 26

| Top 10 Sequences | Count | |
|---|---|---|
| TCTTCCTGAAGGTCAACTGGTGGTGAGATCTAGCGGTAGCAGGTGTCTTGAAGGTTGTCTGTGCAACC | 36104 | (SEQ ID NO: 135) |
| TCTTCCTGGTGACAACTGCTGAGATTCTCCTATAGCTGTGACTTGAAGGTGTCTTGAGTTGTCAGGTGTACC | 23173 | (SEQ ID NO: 136) |
| TCTTCCTGATGAGAAGACTTGAGATAGGACATTAGTTCGAGTGTCTTGCTGCAGTCTCTACGATGTTGGAATGAACC | 16464 | (SEQ ID NO: 137) |
| TCTTCCTTAGCACAACTGTCGCAGATAGGACATTAGCATTAGCACCAGGTGTCTTCGACAGGTCCTGCTGATGTCAAGGTGTACC | 14251 | (SEQ ID NO: 138) |
| TCTTCCTCTAGACAACTTAGCAGATAGGACATTAGCAACTGTCTTCTTAGCAGTGTCTTCGAGTGTCTTAGCTGACC | 10994 | (SEQ ID NO: 139) |
| TCTTCCTGGTGACAATGACAGGATTGGATGATAGTGGATGAGACTTCTCCTAGTCTCTAGCATGTTTCGAGTACC | 8501 | (SEQ ID NO: 140) |
| TCTTCCTGACAAGACTTCAGATCTGAGCATCGTTGGATTAGCTGGATGAGTGTGACTTCAACC | 4507 | (SEQ ID NO: 141) |
| TCTTCCTGAAGACTGTCGAATCGACAGGATTTCGAGTTAGCTGCTGACTTCTAGCAGTCTGGTCCATGTGATGACTACC | 4057 | (SEQ ID NO: 142) |
| TCTTCCTGGTGACAACTGCTGAGATTCTCCTATAGCTGTGACTTGAAGGTGTCTTGAGTTGCCAAGGTGTACC | 3306 | (SEQ ID NO: 143) |
| TCTTCCTGTGCAAAGGACATGATTCTAGCATAGCTAGCTGCTTCAACTGTGTGGACTTCATGTCTGTGCAACC | 3248 | (SEQ ID NO: 144) |

FIG. 27A

| Rank | Variable | Count | |
|---|---|---|---|
| 1 | TCTCCTACAATCGACAGGATTGCTCCATAGCAACTGTCTTCTAGCTG | 5357 | (SEQ ID NO: 145) |
| 2 | TGGATGACAACTGTGCAGATGACTTCATAGCTTAGCACTTCAACTGT | 2368 | (SEQ ID NO: 146) |
| 3 | GATGACTCAACTTAGCACAGATCTGCTGATAGCAACTGTCTTTCTCCTA | 2160 | (SEQ ID NO: 147) |
| 4 | CAACTGTCAAAGGACATGATTCTAGCATAGTCTCCTACTTCAGGTGT | 1763 | (SEQ ID NO: 148) |
| 5 | TGGATGACAACTTAGCAGATCTGCTGATAGCAACTGTCTTTCTCCTA | 843 | (SEQ ID NO: 149) |
| 6 | TGAAGGTCAATTCGAGTGATTGAAAGGTTAGTTCGAGTCTTTCGACAG | 629 | (SEQ ID NO: 150) |
| 7 | CTTAGCACAATGAAGGTGATCTTAGCATAGTCTCCTACTTAGGACAG | 606 | (SEQ ID NO: 151) |
| 8 | TCTCCTACAATGAAGGTGATTGGATAGTCTAGCACTTCTGTGCA | 583 | (SEQ ID NO: 152) |
| 9 | CAACTGTCAACTGTGCAGATTGAAGGTTAGCAACTGTCTTCTGTGCA | 570 | (SEQ ID NO: 153) |
| 10 | CTTAGCACAACTGTGCAGATTGCTCCATAGCAACTGTCTTCTGTGCA | 511 | (SEQ ID NO: 154) |

FIG. 27B

NANOSTRUCTURE, A BIOSENSOR INCLUDING THE NANOSTRUCTURE, AND A SCREENING METHOD

CROSS-REFERENCE TO RELATED APPLICATION

This application claims priority to and the benefit of Korean Patent Application No. 10-2020-0023925, filed in the Korean Intellectual Property Office on Feb. 26, 2020, the entire contents of which are incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted herewith and identified as follows: ASCII text file named "OPP20200372US_Revised_SEQ221214.TXT", created 12/14/22, having 67,194 bytes in size.

BACKGROUND OF THE INVENTION

(a) Field of the Invention

A nanostructure, a biosensor including the nanostructure, and a screening method are disclosed.

(b) Description of the Related Art

It is estimated that there are about 10,000 genes associated with human diseases, but only hundreds of target proteins are currently used in clinical trials with FDA approval. However, traditional drug development processes cost 1.2 to 1.7 billion dollars on average and 10 to 15 years to develop a new drug. Accordingly, there is a need for a technology capable of discovering new drug candidates acting on a target substance faster and at a lower cost than traditional drug development processes.

Identifying moieties and/or compounds that specifically interact with target substances is an important process in a discovery of new drug candidates. Recently, technology for discovering new drug candidates using a DNA-encoded chemical library (DECL) has attracted attention.

The DNA-encoded chemical library includes probes that are likely to interact with a target substance, and various types of structures that combine DNA sequences encoding the probes. The DNA-encoded chemical library is treated with a target substance to select a structure (Hit-structure) that has interacted with the target substance. Subsequently, new drug candidates may be found by analyzing a DNA sequence encoding the probe bound to the Hit-structure and then by identifying a structure of the probe, that is, the Hit-compound, that interacted with the target substance.

However, in a library construction, DNA is poorly soluble in both aqueous solutions and organic solvents, and may be particularly aggregated in most organic solvents. Therefore, possible reactions are limited and reaction rates are very slow, and thus types of probes capable of building the library are quite limited. In addition, separation and/or purification procedures to remove excess reagents, solvents, and the like are essential for each reaction process to build each library, but this requires considerable time and cost.

On the other hand, after selecting Hit-structure, the DNA sequence encoding the probe in the Hit-structure is amplified by a polymerase chain reaction (PCR) and analyzed by next generation sequencing (NGS). However, in general, the number of probes in the Hit-structure, that is, the Hit-compound ranges from tens to hundreds of thousands, and thus it may be very difficult and complicated to select bona fide probes among these many hit compounds.

Therefore, there is a need for the development of a DNA-encoded chemical library technology that is easy to build, and is used to easily to analyze and to select Hit-compounds at screening.

SUMMARY OF THE INVENTION

An embodiment provides a nanostructure capable of constructing an ultra-large DNA-encoded chemical library at a low cost and with high efficiency and detecting new drug candidates.

Another embodiment provides a biosensor including the nanostructure.

Another embodiment provides a method of screening a compound that is bound to a biological material using the biosensor.

An embodiment of the present disclosure provides a nanostructure including
a nanoparticle,
a first compound including a probe and bound to the surface of the nanoparticle,
a second compound including a DNA sequence encoding the probe and bound to the surface of the nanoparticle, and
optionally substituted or unsubstituted polyalkylene glycol bound to the surface of the nanoparticle,
wherein when the nanostructure does not include the substituted or unsubstituted polyalkylene glycol, a ratio $((n^1+n^2)/w)$ of the sum of the number of moles $(n^1)$ of the first compound and the number of moles $(n^2)$ of the second compound relative to the weight (w) of the nanostructure is about 1.2 nmol/g to about 85 μmol/g on average.

The nanoparticle may include an organic polymer nanoparticle, an inorganic nanoparticle, an organic-inorganic composite nanoparticle, or a combination thereof.

The nanoparticle may have a core-shell structure wherein the core may include substituted or unsubstituted polystyrene optionally including ferrite, substituted or unsubstituted polyglycidyl methacrylate optionally including ferrite, a substituted or unsubstituted polystyrene-polyglycidyl methacrylate copolymer optionally including ferrite, or a combination thereof, and the shell may include a substituted or unsubstituted polyglycidyl methacrylate.

The nanoparticle may have a size of about 10 nm to about 1,000 nm.

The first compound, and the second compound may independently have at least two ends, wherein one end of which may be bound to the nanoparticle.

The probe may include a peptide, a peptide mimetic, a small molecule, or a combination thereof. Herein, the small molecule that can be synthesized by general DNA-encoded library technology.

The probe may include a D-peptide, an L-peptide, a cyclic peptide, a stapled peptide, a peptoid, a cyclic peptoid, a foldamer, a small molecule including a triazine moiety, a small molecule including a pyrrolopyrimidine moiety, a small molecule including a benzimidazole moiety, or a combination thereof.

The second compound may include a primer at both ends of the DNA sequence encoding the probe.

A weight average molecular weight of the substituted or unsubstituted polyalkylene glycol may be about 1,000 Da to about 10,000 Da.

The substituted or unsubstituted polyalkylene glycol may be substituted or unsubstituted polyethylene glycol.

A ratio ($n^1$:$n^2$) of the number of moles ($n^1$) of the first compound and the number of moles ($n^2$) of the second compound may be about 3:1 to about 1,000:1.

When the nanostructure includes the substituted or unsubstituted polyalkylene glycol, a ratio ($n^3$/w) of the number of moles ($n^3$) of the substituted or unsubstituted polyalkylene glycol relative to the weight (w) of the nanostructure may be greater than or equal to about 100 μmol/g on average.

When the nanostructure does not include the substituted or unsubstituted polyalkylene glycol, a ratio ($n^1$/w) of the number of moles ($n^1$) of the first compound relative to the weight (w) of the nanostructure may be less than or equal to about 60 μmol/g.

In another embodiment of the present disclosure, a biosensor including the nanostructure is provided.

In another embodiment of the present disclosure, in the biosensor, a screening method includes contacting a biological material with the biosensor.

The biological material is labeled with a labeling material, and the labeling material may be biotin, histag, Ni-NTA, N-hydroxysuccinmide, amine, thiol, histidine, phosphine, aldehyde tag, hydrazide tag, halide, alkyne, azide, halotag, benzlguanin, snap tag, benzylcytosine, CLIP-tag, flag-tag, maleimide, or a combination thereof.

The screening method may further include selecting a nanostructure that is interacted with the biological material in the biosensor.

The selecting of the nanostructure that is interacted with the biological material may include preparing a container coated with a material that is bound to the biological material, and attaching the nanostructure interacted with the biological material to the container.

The screening method may further include identifying a compound interacted with the biological material from the selected nanostructure interacted with the biological material.

The identifying of the compound interacted with the biological material from the selected nanostructure interacted with the biological material may include amplifying a DNA sequence of the second compound of the selected nanostructure interacted with the biological material, and analyzing the amplified DNA sequence.

The nanostructure or biosensor according to the embodiment may identify a new drug candidate material by identifying a compound that is bound to a biological material at a low cost and with high efficiency, thereby reducing a new drug development period and a development cost.

BRIEF DESCRIPTION OF THE DRAWINGS

FIG. 24A and FIG. 24B illustrate the top 30 DNA sequences selected by screening LRH-1 in the stapled peptide library according to Example 1, and FIG. 24C and FIG. 24D illustrate decoded sequences of peptides (Hit-stapled peptides) that are bound to LRH-1 protein, from the DNA sequences selected in FIG. 24A and FIG. 24B.

FIG. 26 illustrates the top 10 DNA sequences selected by screening PTP1B in the peptoid library according to Example 2.

FIG. 27A illustrates the top 10 DNA sequences selected by screening Bcl-xL in an alpha-helix analogue library having the triazine-piperazine-triazine backbone according to Example 3, and FIG. 27B illustrates decoded sequences of an alpha-helix analogue having a triazine-piperazine-triazine backbone (Hit-triazine-piperazine-triazine backbone) that is bound to the Bcl-xL protein, from the selected DNA sequences.

DETAILED DESCRIPTION OF THE EMBODIMENTS

Figure 1:
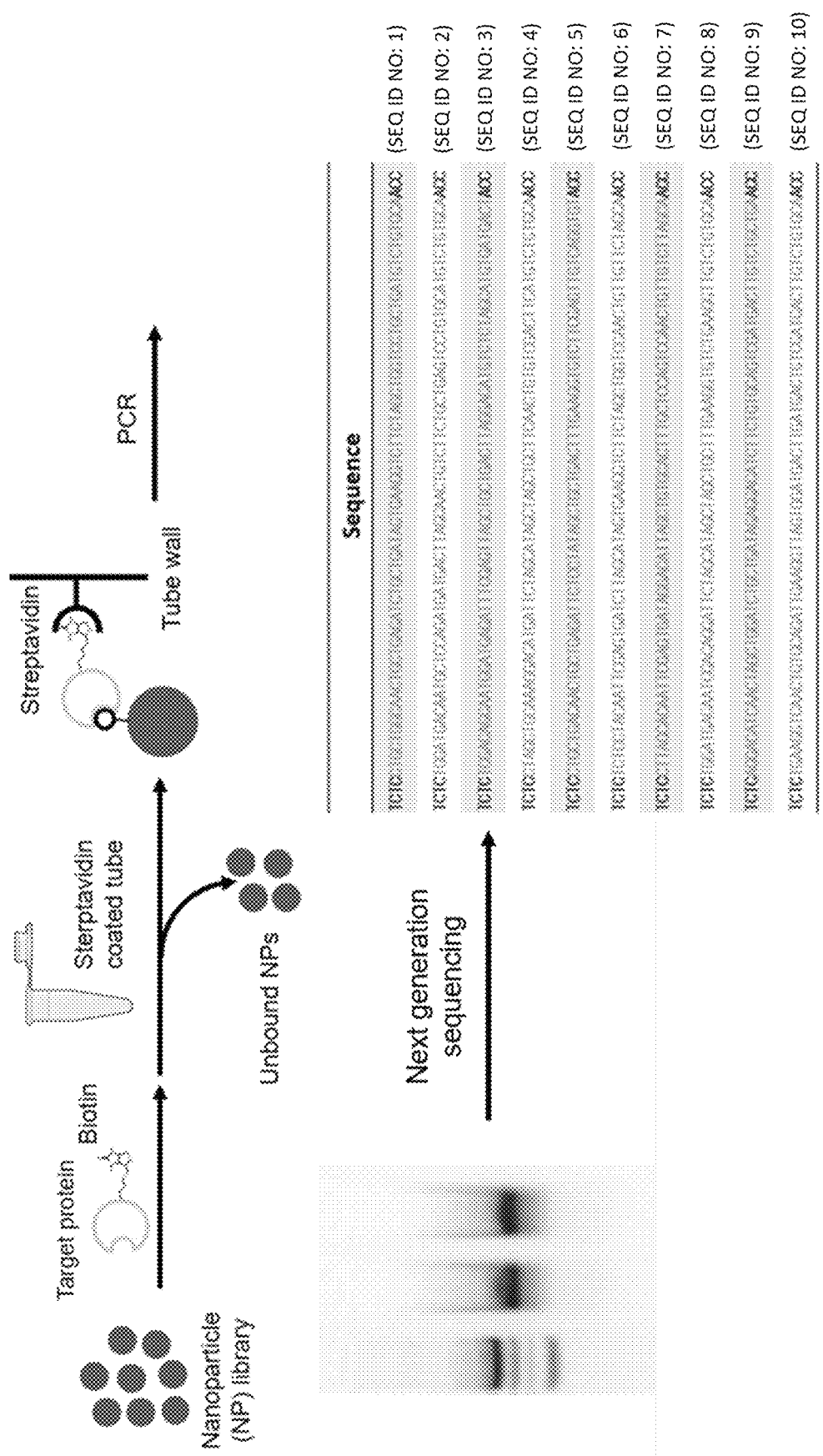
FIG. 1 is a flowchart schematically illustrating a method of screening a biological material using a biosensor including a nanostructure according to an embodiment of the present disclosure.

Hereinafter, exemplary embodiments of the present disclosure will be described in detail with reference to the accompanying drawings so that those skilled in the art may easily implement the present disclosure. However, this disclosure may be embodied in many different forms and is not construed as limited to the example embodiments set forth herein.

The terminology used herein is for the purpose of describing particular embodiments only and is not intended to be limiting of the invention. As used herein, the singular also includes the plural unless specifically stated otherwise in the phrase. As used herein, "comprises" and/or "comprising" refers to a component, or step, that does not exclude the presence or addition of one or more other components, or steps.

As used herein, when a definition is not otherwise provided, "substituted" refers to replacement of a hydrogen atom of a compound by a substituent selected from deuterium, a halogen atom (F, Br, Cl, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C30 alkyl group, a C2 to C30 alkenyl group, a C2 to C30 alkynyl group, a C6 to C30 aryl group, a C7 to C30 arylalkyl group, a 01 to C30 alkoxy group, a 01 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C30 heterocyclic group, and a combination thereof.

In addition, two adjacent substituents of the substituted halogen atom (F, Br, Cl, or I), hydroxy group, nitro group, cyano group, amino group, azido group, amidino group, hydrazino group, hydrazono group, carbonyl group, carbamyl group, thiol group, ester group, carboxyl group or salt thereof, sulfonic acid group or salt thereof, phosphoric acid group or salt thereof, 01 to C30 alkyl group, C2 to C30 alkenyl group, C2 to C30 alkynyl group, C6 to C30 aryl group, C7 to C30 arylalkyl group, 01 to C30 alkoxy group, 01 to C20 heteroalkyl group, C3 to C20 heteroarylalkyl group, C3 to C30 cycloalkyl group, C3 to C15 cycloalkenyl group, C6 to C15 cycloalkynyl group, and C2 to C30 heterocyclic group may be fused to form a ring. For example, the substituted C6 to C30 aryl group may be fused with another adjacent substituted C6 to C30 aryl group to form a substituted or unsubstituted fluorene ring.

As used herein, when a definition is not otherwise provided, "hetero" refers to one including 1 to 3 heteroatoms selected from N, O, S, Se, and P.

As used herein, an average may be a mean, a mode, or a median.

As used herein, a particle size may be obtained by analyzing two-dimensional images obtained from dynamic light scattering methods, and/or electron microscopy (e.g., TEM or SEM) with commercially available image analysis programs (e.g., image J).

As used herein, the polymer may refer to an oligomer, a polymer, or both.

As used herein, the compound may include a chemical moiety.

As used herein, a small molecule is an organic compound of less than or equal to about 900 Da, and may mean a compound that is bound to a biopolymer such as a protein or a nucleic acid to control a function of a biopolymer. For example, the small molecule may be a cell signaling substance.

As used herein, "building block" is a basic chemical structural unit to synthesize a combinatorial chemical library, and may be linkable to or linked to other chemical structural units. For, example, building blocks used for the synthesis of a combinatorial chemical library of a polymer or oligomer may refer to a structural unit derived from the monomer constituting the polymer or oligomer.

As used herein, "initiating oligonucleotide" refers to a starting oligonucleotide for library synthesis of oligonucleotides. The initiating oligonucleotides may be a single strand or a double strand and may include natural bases, non-natural bases, or a combination thereof.

As used herein, "linker" refers to a molecule that links a first compound, a second compound, or a substituted or unsubstituted polyalkylene glycol to a nanoparticle.

As used herein, "probe" refers to a compound that is likely to interact with a target substance.

As used herein, "a DNA sequence encoding a probe" refers to a DNA tag that encodes the type, the number, and the order of building blocks constituting the probe.

As used herein, "library" refers to a combination of different compounds, or fragments thereof.

As used herein, "Hit" may be one interacted with a target substance, for example, one bound to the target substance. For example, "Hit-nanostructure" refers to a nanostructure combined with a target substance. In addition, "Hit-compound" refers to a compound that is bound to a target substance or a probe that interacts with a target substance in the compound that is bound to the target substance.

As used herein, "screening" refers to a task of identifying a probe (Hit-compound) that interacts with a target substance by selecting a structure (Hit-nanostructure) that interacts with the target substance in the library.

When building DNA-encoded libraries in a liquid phase, there are very limited types of probes that may be synthesized. Since DNA has a very low solubility in an organic solvent phase, it should be synthesized in a water-containing condition during library synthesis, while most organic reactions occur in organic solvent phases. Thus, types of available reactions are very limited and structural diversity of the constructible probes is also low. In addition, a repetitive purification process is essential to remove excess DNA tags or reactants in each reaction step. It takes high cost and a lot of time due to complicated separation and/or purification of high-performance liquid chromatography (HPLC) and freeze drying.

Thus, in order to build libraries with various types of probes, and to simplify separation and/or purification process, it is advantageous to build DNA-encoding libraries in the solid phase.

A nanostructure according to an embodiment of the present disclosure includes nanoparticles, a first compound including a probe and bound to the surface of the nanoparticles, a second compound including a DNA sequence encoding the probe and bound to the surface of the nanoparticles, and optionally a substituted or unsubstituted polyalkylene glycol bound to the surface of the nanoparticles.

The nanostructure may construct solid-phase DNA-encoded chemical libraries having various types of probes that are not available with conventional methods, without limitation of a solvent. In addition, the nanostructure may be separated and/or purified by a simple method such as centrifugation or using a magnet from excess reactants, solvents, enzymes, and the like and a huge DNA-encoded chemical library may be constructed.

The nanoparticles may be a two-dimensional or three-dimensional particle having a nanoparticle size, and may include organic polymer nanoparticles, inorganic nanoparticles, organic-inorganic composite nanoparticles, or a combination thereof.

The organic polymer nanoparticles may be composed of an organic polymer or may include an organic polymer as a main component, and the organic polymer may include a homopolymer and/or a copolymer. For example, the organic polymer may be a homopolymer, a block copolymer, a random copolymer, an alternating copolymer, a crosslinked copolymer branch copolymer, or a combination thereof.

For example, the organic polymer may include a substituted or unsubstituted polystyrene, a substituted or unsubstituted polyethylene glycol, a substituted or unsubstituted polyamide, a substituted or unsubstituted polyacrylamide, a substituted or unsubstituted polyester, a substituted or unsubstituted polyurethane, a substituted or unsubstituted polycarbonate, a substituted or unsubstituted polyalkylene, a substituted or unsubstituted polyglycidylmethacrylate, or a combination thereof, but is not limited thereto.

Specifically, the organic polymer may include a substituted or unsubstituted polystyrene, a substituted or unsubstituted polyglycidyl methacrylate, a substituted or unsubstituted polyethylene glycol-polystyrene copolymer, a substituted or unsubstituted polyethylene glycol-polyacrylamide copolymer, a substituted or unsubstituted polystyrene-polyglycidylmethacrylate copolymer, or a combination thereof, but is not limited thereto.

More specifically, the organic polymer nanoparticles may include Tentagel (Rapp-Polymere, Inc.), Dynabead (Invitrogen, Inc.), AccuNanoBead (Bionner, Inc.), FG-beads (Tamagawa Seiki, Inc.), or a combination thereof, but is not limited thereto.

The inorganic nanoparticles may be made of an inorganic material or may include an inorganic material as a main component. The inorganic nanoparticles may be a compound consisting of one element, a binary element compound, a ternary element compound, or a quaternary element compound. In the case of the binary element compound or more, these may be present in the nanoparticles at uniform concentrations, or may be present in the same nanoparticles which are divided to have partially different concentrations. For example, the inorganic nanoparticles may have a core-shell structure, and the interface between the core and the shell may have a concentration gradient that a concentration of the element in the shell decreases toward the center.

The inorganic material may include a metal, a non-metal, a semi-metal, a semiconductor, an oxide thereof, an alloy thereof, or a combination thereof. For example, the inorganic material may be gold, silver, copper, platinum, iron, cobalt, manganese, zinc, barium, nickel, aluminum, indium, titanium, tellurium, selenium, silicon, phosphorus, sulfur, an oxide thereof, an alloy thereof, or a combination thereof.

For example, the inorganic material may be a magnetic material, and the magnetic material may be iron (Fe), cobalt (Co), iron oxide, cobalt oxide, manganese oxide, zinc oxide, or an alloy thereof, or a combination thereof. For example, the magnetic material may be an oxide of iron and/or zinc. Accordingly, the magnetic field may be used to easily purify and/or separate nanostructures including the nanoparticles and the compound bound to the nanostructure.

For example, the inorganic material may include ferrite, and may be, for example, ferrite coated with silica. Herein, the ferrite may be a ceramic material including a large amount of iron (III) oxide mixed with a small amount of barium, manganese, nickel, and/or zinc, and may include soft ferrite and hard ferrite.

The organic-inorganic nanoparticles may include both of an organic material and an inorganic material. For example, the organic material and the inorganic material may be uniformly present in the nanoparticles, or may non-uniformly be present in the same nanoparticles which are divided to have partially different concentrations. For example, the organic-inorganic nanoparticles may have a core-shell structure, and the interface between the core and the shell may have a concentration gradient that a concentration of the element in the shell decreases toward the center. Herein, the organic material may include an organic polymer, and the organic polymer and the inorganic material are as described above, respectively.

For example, the nanoparticles may have a core-shell structure. The core may be an organic polymer optionally including ferrite, and the shell may be an organic polymer or an inorganic material. Herein, the ferrite, the organic-inorganic nanoparticles, the organic polymer, and the inorganic material are as described above.

For example, the core may include substituted or unsubstituted polystyrene optionally including ferrite, substituted or unsubstituted polyglycidyl methacrylate optionally including ferrite, a substituted or unsubstituted polystyrene-polyglycidyl methacrylate copolymer optionally including ferrite, or a combination thereof, and for example, the shell may include silica, a substituted or unsubstituted polyglycidylmethacrylate, a substituted or unsubstituted polyethylene glycol, or a combination thereof.

When synthesizing a DNA sequence encoding the probe on an organic polymer bead having a particle size of several micro level, there is a possibility that the DNA sequence encoding the probe is also synthesized inside the organic polymer bead. However, since a ligase used to synthesize the DNA sequence is difficult to access inside the organic polymer bead, the DNA sequence encoding the probe is uneven and inaccurate. According to an embodiment, when the nanoparticles have a core-shell structure, a reaction may occur only on the surface of the nanoparticles. Accordingly, the DNA sequence encoding the probe may be uniform, and accuracy of DNA sequence analysis may be improved at screening. It is also possible to select Hit-compound that is strongly bound to biological material. The biological material may be a target substance, and descriptions related to the biological material will be described later.

The nanoparticles may have a size of about 10 nm to about 1000 nm, for example, about 20 nm to about 800 nm, about 40 nm to about 700 nm, about 60 nm to about 500 nm, about 80 nm to about 500 nm, about 90 nm to 400 nm, about 100 nm to about 300 nm, about 150 nm to about 250 nm, about 170 nm to about 230 nm, or about 190 nm to about 210 nm. When the nanoparticles are spherical nanoparticles, the sizes of the nanoparticles refer to particle diameters of the spherical nanoparticles. Here, the spherical shape may not be a perfect spherical shape, wherein the size of the nanoparticles may refer to the largest particle diameter among the particle diameters. When the nanoparticles are core-shell nanoparticles, the size of the nanoparticles refer to a particle diameter of the entire nanoparticles including the core and the shell.

Since the nanoparticles have a size in the above-described range, a volume may be reduced compared with the case of using the polymer bead having a size of the micrometer level, and thus it is possible to build trillions or more ultra-large library. In addition, compared with the use of micrometer-level organic polymer beads, it is also possible to reduce false positive reactions to select nanostructures in which the biological material is physically trapped inside the organic polymer bead, as Hit-nanostructures.

As described above, in the nanostructures according to an embodiment, the first compound and the second compound may exist only on the surface of the nanoparticles. Accordingly, it is compatible with most solvents and thus may be synthesized at a high concentration regardless of low solubility of DNA, thereby reducing a time required for constructing the library. Reactions in organic solvents, which are not possible with current technology, may enable the construction of a wide variety of libraries. In addition, since the reaction occurs only at the surface, a ligase for synthesizing the second compound may be uniformly accessed, the DNA sequence may be uniformly synthesized, and the accuracy of the structural analysis of the Hit-compound after screening may be improved.

According to an embodiment, the nanostructures may include a first compound including one type of the probe and a second compound including a DNA sequence encoding one type of the probe, per one nanoparticle. The DNA sequence encoding one species of the probe encodes only one species of the probe. Accordingly, at affinity-based screening for biological materials, the structure of the Hit-compound may be confirmed by analyzing DNA sequence of the Hit-nanostructure bound to the biological material.

The first compound has at least two ends, one end of which may be bound to the surface of the nanoparticles. Accordingly, the first compound and the biological material may interact with each other and bind to each other only on the surface of the nanoparticles, for example, the probe of the first compound and the biological material may interact with each other and bind to each other. Thus, at the affinity-based screening using the aforementioned nanostructure, it is possible to suppress a false positive reaction that the biological material is trapped inside the nanoparticles.

The probe may be any organic molecule or inorganic molecule, and may be designed to be bound to a biological material based on properties such as hydrogen bonding potential, solubility, rotational freedom of bonding, positive charge, and negative charge.

The probe may be formed by polymerization of one or more first building blocks, for example, by polymerization in a solid phase.

The first building block may be, for example, an amino acid, or an analogue thereof; N-alkylated glycine; a combination of substituted or unsubstituted amine, substituted or unsubstituted triazine, and substituted or unsubstituted triazines; or a combination thereof. Herein, the amino acid may include natural amino acids and non-natural amino acids, and may be L-form and/or D-form.

For example, the amino acid may include alanine (Ala), arginine (Arg), asparagine (Asn), aspartic acid (Asp), cysteine (Cys), glutamic acid (Glu), glutamine (Gln), glycine (Gly), histidine (His), hydroxyproline (Hyp), isoleucine (Ile), leucine (Leu), lysine (Lys), methionine (Met) phenylalanine (Phe), proline (Pro), pyroglutamic acid (Glp), serine, threonine (Thr), tryptophan (Trp), tyrosine (Tyr), Valine (Val), or norleucine (Nle), cyclohexylalanine (Cha), 1-naphthylalanine (Nap), 4-chlorophenylalanine ($Phe^{Cl}$), 4-fluorophenylalanine ($Phe^{F}$), 4-nitrophenylalanine ($Phe^{NO2}$), homophenylalanine ($^{h}Phe$), homoarginine ($^{h}Arg$), 2-amino isobutyric acid (Aib), and the like, but is not limited thereto.

Analogues of the amino acids may be capped with a protecting group so that each of the aforementioned amino acids may be polymerized in a solid phase. They may be, for example, protected with Fmoc (fluorenylmethyloxycarbonyl) protecting group, Nosyl (nitrobenzensulfonyl), Trt (trityl), Dde (1-(4,4-dimethyl-2,6-dioxacyclohexylidene)ethyl), Alloc (allyloxycarbonyl), Mmt (monomethoxytrityl), azide, or a combination thereof. The protecting group may be substituted or capped at the N-terminus of the amino acid.

Specifically, the analogue of the amino acid may be Fmoc-Ala-OH, Fmoc-Arg-OH, Fmoc-Asn-OH, Fmoc-Asp-OH, Fmoc-Cys-OH, Fmoc-Glu-OH, Fmoc-Gln-OH, Fmoc-Gly-OH, Fmoc-His-OH, Fmoc-Hyp-OH, Fmoc-Ile-OH, Fmoc-Leu-OH, Fmoc-Lys-OH, Fmoc-Met-OH, Fmoc-Phe-OH, Fmoc-Pro-OH, Fmoc-Glp-OH, Fmoc-Ser-OH, Fmoc-Thr-OH, Fmoc-Trp-OH, Fmoc-Tyr-OH, Fmoc-Val-OH, or Fmoc-Nle-OH, Fmoc-Cha-OH, Fmoc-Nap-OH, Fmoc-$Phe^{Cl}$-OH, Fmoc-$Phe^{F}$-OH, Fmoc-$Phe^{NO2}$-OH, Fmoc-$^{h}Phe$-OH, Fmoc-$^{h}Arg$-OH, Fmoc-Aib-OH, and the like, but is not limited thereto.

For example, the N-alkylated glycine may be formed by a reaction of a primary amine compound with halocarboxylic acid.

The primary amine compound may be represented by Chemical Formula 1.

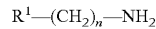

[Chemical Formula 1]

In Chemical Formula 1, $R^1$ is hydrogen, deuterium, a halogen, an alkoxy group, a hydroxy group, a carboxyl group, an amino group, a nitro group, an azide group, a substituted or unsubstituted C1 to C30 alkyl group, a substituted or unsubstituted C3 to C20 cycloalkyl group, a substituted or unsubstituted C2 to C20 heterocycloalkyl group, a substituted or unsubstituted C6 to C20 aryl group, a substituted or unsubstituted C2 to C20 heteroaryl group, or a combination thereof, and n is an integer of 1 or more.

For example, $R^1$ may be hydrogen, an alkoxy group, a hydroxy group, a carboxyl group, an amino group, a nitro group, an azide group, a linear or branched C1 to C10 alkyl group, C1 to C10 alkoxy group, a substituted or unsubstituted C6 to C10 aryl group, a substituted or unsubstituted C3 to C10 cycloalkyl group, a substituted or unsubstituted C3 to C10 heterocycloalkyl group, a substituted or unsubstituted C2 to C10 heteroaryl group, or a combination thereof, but is not limited thereto.

In an embodiment, the substituted or unsubstituted C6 to C10 aryl group may be a substituted or unsubstituted phenyl group, or a substituted or unsubstituted naphthyl group, the substituted or unsubstituted C3 to C10 cycloalkyl group may be a substituted or unsubstituted cyclohexyl group, the substituted or unsubstituted C3 to C10 heterocycloalkyl group may be a substituted or unsubstituted lactam group, the 01 to 010 alkoxy group may be a substituted or unsubstituted methoxy group, a substituted or unsubstituted ethoxy group, a substituted or unsubstituted propoxy group, or a combination thereof, and the substituted or unsubstituted C2 to C10 heteroaryl group may be a substituted or unsubstituted furanyl group, or a substituted or unsubstituted pyridinyl group, but are not limited thereto.

In an embodiment, the primary amine compound may be selected from Group 1-1, and/or Group 1-2.

[Group 1-1]

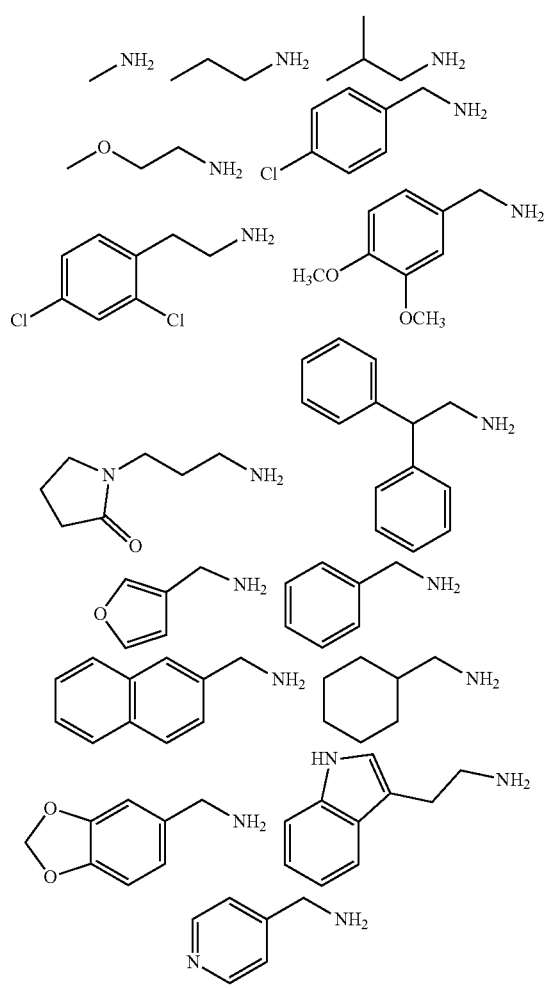

[Group 1-2]

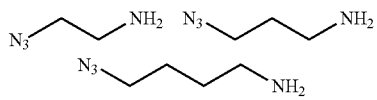

For example, the N-alkylated glycine may be represented by Chemical Formula 2, and in Chemical Formula 2, $R^1$ may be derived from the primary amine compound.

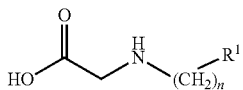

[Chemical Formula 2]

In Chemical Formula 2, $R^1$ and n are the same as $R^1$ and n in Chemical Formula 1, respectively.

For example, the halocarboxylic acid may be haloacetic acid, halopropionic acid, halobutyric acid, halovaleric acid, or a combination thereof. Specifically, the halocarboxylic acid may be chloroacetic acid, bromoacetic acid, chloropropionic acid, bromopropionic acid, chlorobutyric acid, bromobutyric acid, chlorovaleric acid, bromovaleric acid, or a combination thereof, but is not limited thereto.

The substituted or unsubstituted amine may be substituted amine wherein the substituent may be a substituted or unsubstituted C1 to C30 alkyl group, a substituted or unsubstituted C3 to C30 cycloalkyl group, a substituted or unsubstituted C1 to C30 heteroalkyl group, a substituted or unsubstituted C6 to C30 aryl group, a substituted or unsubstituted C2 to C30 heterocyclic group, or a combination thereof. Herein, the substituted or unsubstituted C1 to C30 alkyl group may be a substituted or unsubstituted C1 to C30 linear alkyl group and a substituted or unsubstituted C3 to C20 branched alkyl group and the substituted or unsubstituted C3 to C20 branched alkyl group may be a substituted or unsubstituted C3 to C20 iso-alkyl group, a substituted or unsubstituted C4 to C20 sec-alkyl group, a substituted or unsubstituted C4 to C20 tert-alkyl group, and a substituted or unsubstituted C5 to C20 neo-alkyl group.

Specifically, the substituted or unsubstituted amine may be substituted with a substituted or unsubstituted methyl group, a substituted or unsubstituted ethyl group. substituted or unsubstituted n-propyl group, a substituted or unsubstituted iso-propyl group, a substituted or unsubstituted n-butyl group, a substituted or unsubstituted iso-butyl group, a substituted or unsubstituted sec-butyl group, a substituted or unsubstituted tert-butyl group, a substituted or unsubstituted n-pentyl group, a substituted or unsubstituted iso-pentyl group, a substituted or unsubstituted sec-pentyl group, a substituted or unsubstituted tert-pentyl group, a substituted or unsubstituted neo-pentyl group, a substituted or unsubstituted cyclopropyl group, a substituted or unsubstituted cyclobutyl group, a substituted or unsubstituted cyclopentyl group, a substituted or unsubstituted cyclohexyl group, a substituted or unsubstituted cycloheptyl group, a substituted or unsubstituted phenyl group, a substituted or unsubstituted naphthyl group, a substituted or unsubstituted biphenyl group, a substituted or unsubstituted phenanthrenyl group, a substituted or unsubstituted anthracenyl group, a substituted or unsubstituted pyrenyl group, or a substituted or unsubstituted pyrrolo group, a substituted or unsubstituted pyrrolidinyl group, a substituted or unsubstituted imidazolyl group, a substituted or unsubstituted pyrazolyl group, a substituted or unsubstituted triazolyl group, a substituted or unsubstituted piperidinyl group, a substituted or unsubstituted piperazinyl group, a substituted or unsubstituted pyridyl group, a substituted or unsubstituted pyridmidyl group, a substituted or unsubstituted pyridazinyl group, a substituted or unsubstituted pyrazinyl group, a substituted or unsubstituted morpholinyl group, a substituted or unsubstituted betalactam group, a substituted or unsubstituted gammalactam group, a substituted or unsubstituted deltalactam group, a substituted or unsubstituted furanyl group, a substituted or unsubstituted pyranyl group, a substituted or unsubstituted thiophenyl group, a substituted or unsubstituted tetrahydrothiophenyl group, a substituted or unsubstituted indolo group, a substituted or unsubstituted benzofuranyl group, a substituted or unsubstituted benzothiophenyl group, or a combination thereof.

Specifically, the substituted or unsubstituted amine may be selected from Group 2 or Group 3, but is not limited thereto.

[Group 2]

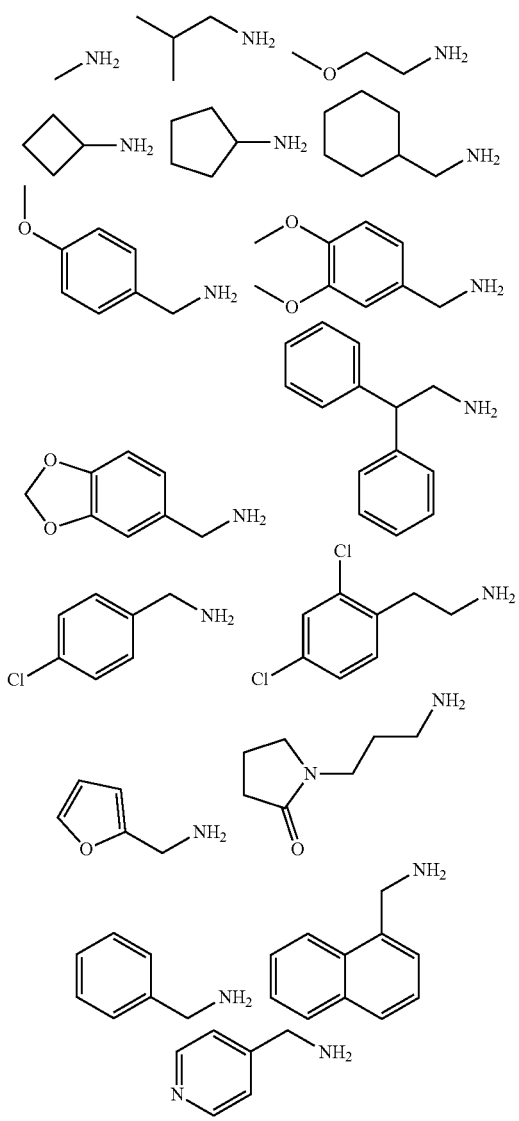

[Group 3]

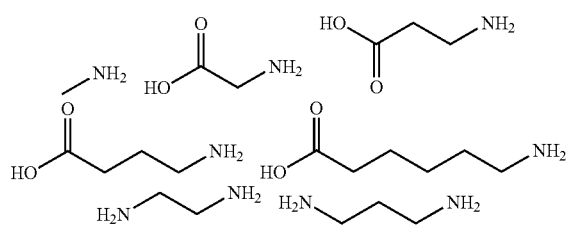

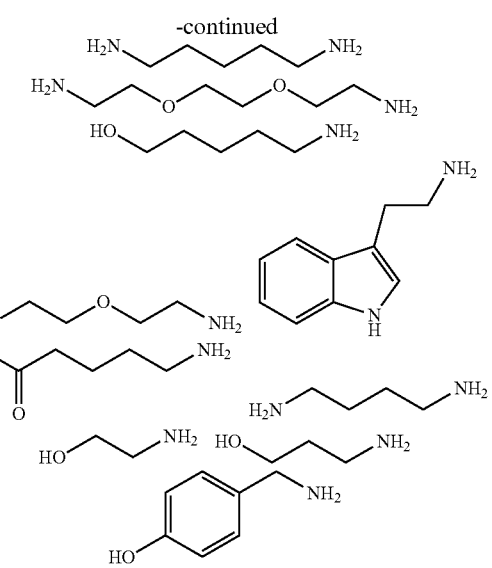

For example, the substituted or unsubstituted triazine may be substituted with at least one halogen group, a substituted or unsubstituted amino group, or a combination thereof.

For example, the substituted or unsubstituted triazine may be substituted with at least two halogen groups, and may be substituted with at least one substituted or unsubstituted amino group.

Specifically, the substituted or unsubstituted amino group may be a substituted amino group, where the substituent may be the same as defined in the substituent of the substituted or unsubstituted amine.

Specifically, the substituted or unsubstituted triazine may be selected from Group 4, but is not limited thereto.

[Group 4]

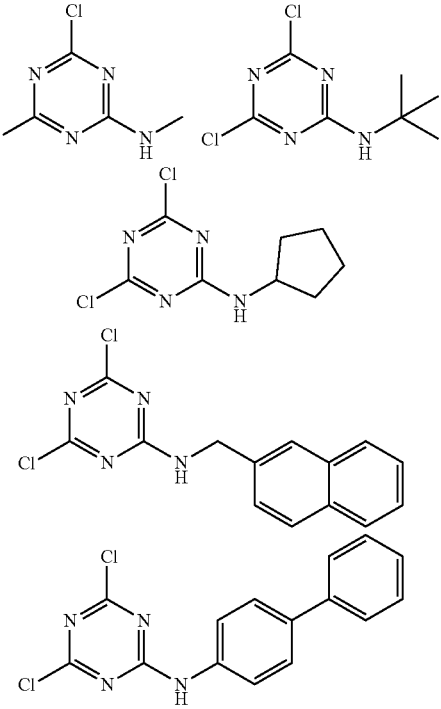

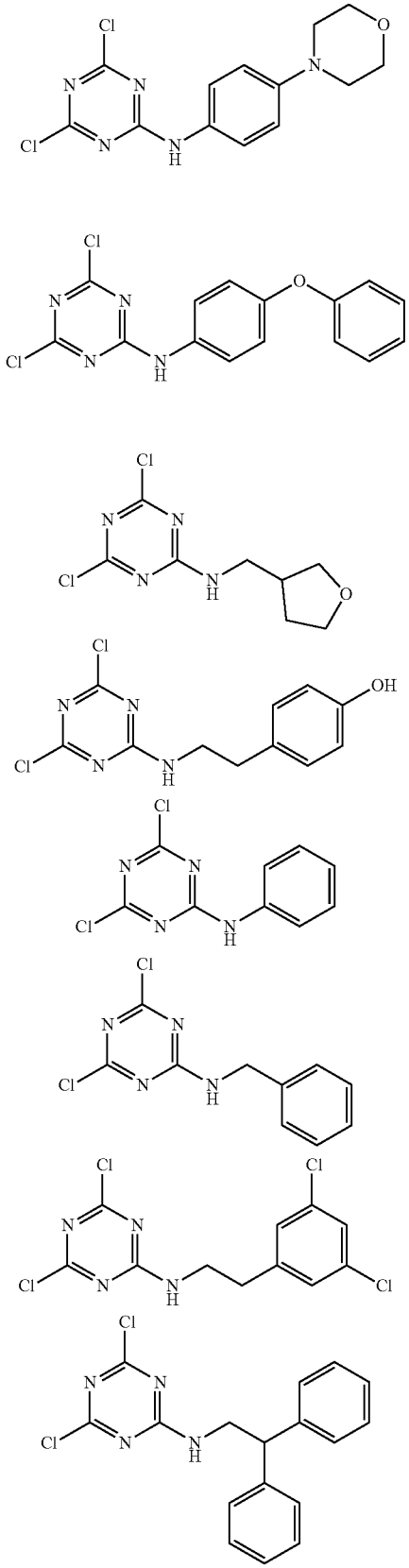

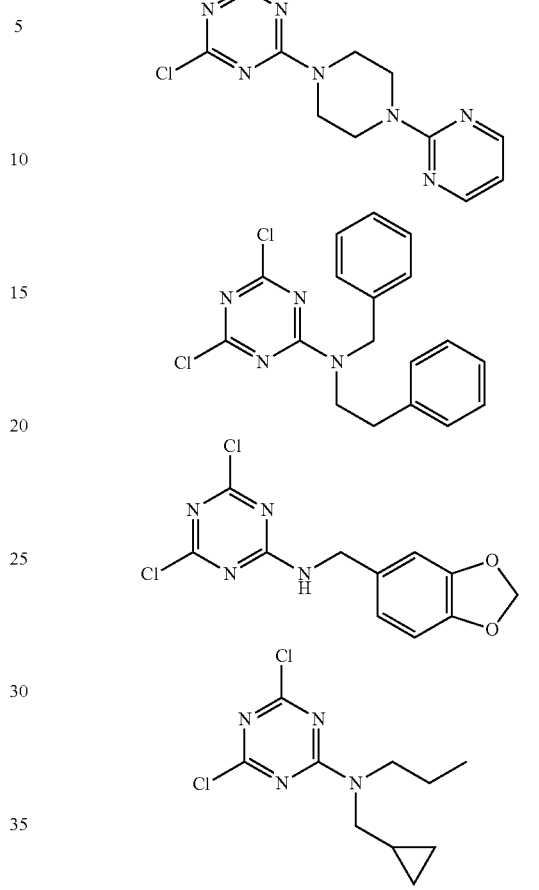

For example, the substituted or unsubstituted piperazine may be substituted with at least one substituted or unsubstituted alkyl group. Herein, the substituted or unsubstituted C1 to C30 alkyl group may be a substituted alkyl group, wherein the substituent may be the same as defined in the substituents of the substituted or unsubstituted amine.

Specifically, the substituted or unsubstituted piperazine may be selected from Group 5, but is not limited thereto.

[Group 5]

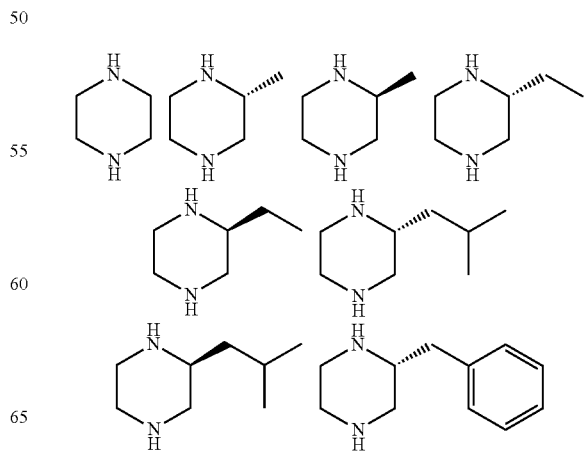

-continued

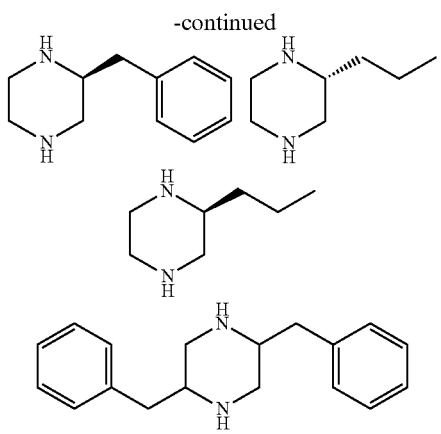

The probe is not limited as long as it is a compound capable of interacting with a biological material, for example, a target substance, and may be desirably a compound capable of binding to a biological material.

For example, the probe may include a peptide, a peptide mimetic, a small molecule, or a combination thereof.

Herein, a small molecule that can be synthesized by general DNA-encoded library technology.

For example, the small molecule may include a hetero aromatic ring moiety including at least one nitrogen atom, and may be for example, a substituted or unsubstituted pyrrole moiety, a substituted or unsubstituted imidazole moiety, a substituted or unsubstituted pyrazole moiety, a substituted or unsubstituted triazole moiety, a substituted or unsubstituted pyridine moiety, a substituted or unsubstituted pyrimidine moiety, a substituted or unsubstituted pyridazine moiety, a substituted or unsubstituted pyrazine moiety, a substituted or unsubstituted indole moiety, a substituted or unsubstituted quinoline moiety, a substituted or unsubstituted isoquinoline moiety, a substituted or unsubstituted carbazole moiety, a substituted or unsubstituted indazole moiety, a substituted or unsubstituted benzimidazole moiety, a substituted or unsubstituted purine moiety, or a combination thereof. For example, the small molecule may be an alpha-helix analogue.

For example, the probe may be a D-peptide, an L-peptide, a cyclic peptide, a stapled peptide, a peptoid, a cyclic peptoid, a foldamer, a small molecule including a triazine moiety, a small molecule including a pyrrolopyrimidine moiety, a small molecule including a benzimidazole moiety, or a combination thereof. For example, the small molecule including the triazine moiety may be an alpha-helix analogue having a triazine-piperazine-triazine backbone. For example, the stapled peptide may be a peptide analogue, and amino acids of the same phase (e.g., I and i+4; or I and i+7) may be covalently linked to form a stable alpha-helix structure.

The D-peptide, L-peptide, and stapled peptide may be formed by polymerizing one or more of the aforementioned amino acids, or analogues thereof. The stapled peptide may have superior binding ability, cell permeability, and proteolytic stability compared with natural peptide.

The peptoid may be a peptide analogue, specifically, may be a linear peptoid, a cyclic peptoid, or a bicyclic peptoid. The peptoid may be formed by polymerizing one or more of the aforementioned N-alkylated glycine. The peptoid may have improved cell permeability, stability against proteolytic enzymes, and the like, compared with natural peptide.

The alpha-helix analogue having the triazine-piperazine-triazine backbone is a low molecular weight alpha-helix mimic that may mimic positions of i, i+3 (or 4), i+7 amino acid residues on the alpha-helix. The alpha-helix analogue having the triazine-piperazine-triazine backbone may be formed by reactions of the aforementioned substituted or unsubstituted amine, substituted or unsubstituted triazine, and substituted or unsubstituted piperazine. Specifically, the alpha-helix analogue having the triazine-piperazine-triazine backbone may be represented by Chemical Formula 3.

[Chemical Formula 3]

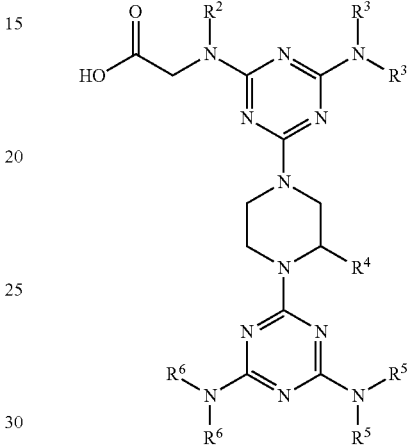

In Chemical Formula 3, $R^2$ may be a monovalent group derived from Group 2, $R^3$ and $R^5$ may independently be a monovalent group derived from Group 4, and $R^4$ may be a monovalent group derived from Group 5, and $R^6$ may be a monovalent group derived from Group 3.

For example, a plurality of second compounds may be bound to the surface of one nanoparticle. In conventional methods of screening with a library including a structure in which one probe and one DNA sequence encoding the probe are combined, the DNA sequence encoding the probe may not provide enough hit signals (or amplified numbers of DNAs) to be observed among background signals and thus the Hit-compound is not accurately analyzed. For example, when conventional screening with a DNA-encoding library including a structure in which one probe and one sequence encoding the probe are combined, even if tens of thousands to hundreds of thousands of Hit-structures are obtained, the number of the finally analyzed DNA encoding sequences may be only a few hundreds. On the other hand, since the nanostructures according to the embodiment include a plurality of second compounds bound to the surface of one nanoparticle, even if some of the second compounds are separated, the structure of the Hit-compound may be analyzed.

In addition, since there are a plurality of second compounds per one nanoparticle, the number of amplified DNA sequences is very large, so that the highest sequence having the highest number of DNA sequences is selected without complicated analysis and Hit-compounds to confirm resynthesis after screening and activity may be easily selected. As a result, the cost and time required for screening the selected Hit-compounds may be greatly saved, and the accuracy of the analysis may be maximized.

For example, the second compound may have at least two ends, one of which may be bound to the nanoparticles.

Accordingly, in the amplifying of the DNA sequence encoding the probe of the Hit-nanostructure that will be described later, a polymerase may be easily accessed, so that the DNA sequence may be uniformly amplified and the structure of the Hit-compound may more accurately be analyzed.

The DNA sequence encoding the probe may be formed by polymerization of a second building block, and may be desirably formed by polymerization in a solid phase. The second building block may be a double strand DNA (dsDNA) fragment, and one type of the second building block may encode only one type of the first building block described above. Accordingly, when screening for a biological material, by analyzing the type, number, and order of the second building block constituting the DNA sequence encoding the probe of the Hit-nanostructure interacted with the biological material, the type, number, and order of the first building block constituting the Hit-compound are confirmed so that the structure of the Hit-compound may be derived.

The second building block may be polymerized by an enzyme to synthesize a DNA sequence encoding the aforementioned probe. The second building block may be a dsDNA fragment having sticky ends at both ends. The dsDNA fragment may have 3 to 15, for example 4 to 13, 5 to 11, or 6 to 10 base pairs. The length of the sticky end may be 2 to 5, for example, three, or four base pairs. Conventionally, compared with a method of synthesizing nucleotides one by one using an organic synthetic method to form a DNA sequence encoding the probe, in the case of synthesizing a dsDNA fragment of the range using an enzyme to form a DNA sequence encoding the probe, a repeated reaction, purification, and separation steps are reduced, and thus yields and purity may be increased and large libraries may be built.

The dsDNA fragment may include a plurality of deoxynucleoside triphosphates (dNTP), for example, deoxyadenine triphosphate (ATP), deoxyguanine triphosphate (GTP), deoxycytosine triphosphate (CTP), or deoxythymidine triphosphate (TTP).

The second compound may include primers at both ends of the DNA sequence encoding the probe. Among the primers at both ends, the second compound may further include a headpiece at the end of the primer located at the end of the side linked with the nanoparticles. The headpiece may include a reactive functional group capable of binding to nanoparticles, and the headpiece may further include an initiating oligonucleotide.

Accordingly, the DNA sequence encoding the probe of the second compound may be amplified by a polymerase chain reaction (PCR), and the amplified DNA sequence is analyzed to determine type, number, and order of the second building block constituting the second compound. That is, new drug candidates may be selected by checking the structure of the first compound based on the type, number, and order of the first building blocks encoded by each second building block.

The number of moles ($n^1$) of the first compound may be greater than the number of moles ($n^2$) of the second compound, such that the biological material that will be described later is not bound to a second compound (e.g., a DNA sequence encoding the probe), thereby reducing false positive interactions. For example, the ratio ($n^1$:$n^2$) of the number of moles ($n^1$) of the first compound and the number of moles ($n^2$) of the second compound may be about 1.5:1 to about 1,000:1, for example, about 1.6:1 to about 500:1, about 1.6:1 to about 300:1, about 1.7:1 to about 200:1, about 1.7:1 to about 150:1, about 1.8:1 to about 100:1, about 1.8:1 to about 70:1, about 1.9:1 to about 50:1, about 1.9:1 to about 30:1, about 2:1 to about 20:1, about 2:1 to about 10:1, about 2:1 to about 5:1, or about 2:1 to about 4:1.

When the nanostructures include a substituted or unsubstituted polyalkylene glycol, or when the nanostructures do not include the polyalkylene glycol, a ratio (($n^1$+$n^2$)/w) of the sum of the number of moles ($n^1$) of the first compound and the number of the moles ($n^2$) of the second compound relative to the weight (w) of the nanostructures may be less than or equal to about 85 μmol/g, for example, less than or equal to about 70 μmol/g, less than or equal to about 60 μmol/g, less than or equal to about 50 μmol/g, or less than or equal to about 45 μmol/g on average.

A lower limit of the ratio (($n^1$+$n^2$)/w) of the sum of the number of moles ($n^1$) of the first compound and the number of the moles ($n^2$) of the second compound relative to the weight (w) of the nanostructures is not limited and may be, for example, greater than or equal to about 1.2 nmol/g, for example, greater than or equal to about 10 nmol/g, greater than or equal to about 50 nmol/g, greater than or equal to about 100 nmol/g, greater than or equal to about 500 nmol/g, greater than or equal to about 1 μmol/g, greater than or equal to about 5 μmol/g, greater than or equal to about 10 μmol/g, or greater than or equal to about 15 μmol/g on average.

When the nanostructures include the substituted or unsubstituted polyalkylene glycol, the substituted or unsubstituted polyalkylene glycol may increase physical distance between nanostructures, thereby increasing stability of the nanostructures. On the other hand, when the nanostructures do not include a substituted or unsubstituted polyalkylene glycol bound to the surface of the nanoparticles, the ratio (($n^1$+$n^2$)/w) of the sum of the number of moles ($n^1$) of the first compound and the number of the moles ($n^2$) of the second compound relative to the weight (w) of the nanostructures falls in the above range and thus an attractive force between the nanostructures may be reduced and stability of the nanostructures may be increased. Accordingly, the aforementioned nanostructures may be well dispersed in a solvent while having a nano-level size, without irreversible and permanent aggregation phenomenon, and may increase reliability of analytical results by reducing false positive interactions at screening.

A weight average molecular weight of the substituted or unsubstituted polyalkylene glycol may be, for example, about 1,000 Da to about 10,000 Da, about 3,000 Da to about 7,000 Da, about 4,000 Da to about 6,000 Da, or about 4,500 Da to about 5,500 Da. When the weight average molecular weight is within the above range, synthesis of the first compound and the second compound and new drug candidate selection using the nanostructures may be facilitated while aggregation between the nanostructures may be suppressed.

For example, the substituted or unsubstituted polyalkylene glycol may have at least two ends, wherein one end of which may be bound to the nanoparticle, for example, the substituted or unsubstituted polyalkylene glycol may be represented by Chemical Formula 4.

[Chemical Formula 4]

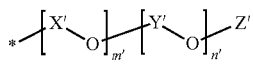

In Chemical Formula 4, X' and Y' are independently a substituted or unsubstituted C1 to C15 alkylene group, a substituted or unsubstituted C6 to C30 arylene group, or a combination thereof, Z' is hydrogen, a C1 to C15 alkyl group, a C6 to C30 aryl group, or a combination thereof, m' and n' are independently an integer of 0 to 5, m'+n' satisfies a range of 2≤m'+n'8, and

* is a point connected to the nanoparticles.

For example, X' and Y' may independently be a substituted or unsubstituted methylene group, a substituted or unsubstituted ethylene group, a substituted or unsubstituted propylene group, a substituted or unsubstituted butylene group, a substituted or unsubstituted pentylene group, a substituted or unsubstituted hexylene group, or a combination thereof, and specifically, X' and Y' may independently be a substituted or unsubstituted methylene group, a substituted or unsubstituted ethylene group, a substituted or unsubstituted n-propylene group, a substituted or unsubstituted n-butylene group, a substituted or unsubstituted n-pentylene group or a substituted or unsubstituted n-hexylene group, but are not limited thereto.

For example, Z' may be a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted hexyl group, or a combination thereof, and more specifically, Z' may be a substituted or unsubstituted methyl group, a substituted or unsubstituted ethyl group, a substituted or unsubstituted n-propyl group, a substituted or unsubstituted n-butyl group, a substituted or unsubstituted n-pentyl group, or a substituted or unsubstituted n-hexyl group.

For example, X' and Y' may be the same or different, and m' and n' may be the same or different.

For example, m' and n' may independently be an integer of 0 to 3, for example, may be an integer of 0 to 2. For example, m' may be 2 and n' may be 0.

For example, at least one of m' and n' may be zero.

For example, X' and Y' may independently be a substituted or unsubstituted ethylene group and Z' may be a substituted or unsubstituted methyl group.

For example, the substituted or unsubstituted polyalkylene glycol may be substituted or unsubstituted polyethylene glycol, but is not limited thereto.

When the nanostructures include the substituted or unsubstituted polyalkylene glycol bound to the surface of the nanoparticles, a ratio $(n^3/(n^1+n^2+n^3))$ of the number of moles $(n^3)$ of the substituted or unsubstituted polyalkylene glycol relative to the sum $(n^1+n^2+n^3)$ of the number of moles of the first compound, the second compound, and the substituted or unsubstituted polyalkylene glycol on the surface of the nanoparticles may be greater than or equal to about 0.3, for example, greater than or equal to about 0.4 or greater than or equal to about 0.5.

For example, a ratio $(n^3/w)$ of the number of the moles $(n^3)$ of the substituted or unsubstituted polyalkylene glycol relative to the weight (w) of the nanostructures may be greater than or equal to about 100 µmol/g on average, greater than or equal to about 150 µmol/g on average, greater than or equal to about 200 µmol/g on average, greater than or equal to about 250 µmol/g on average, greater than or equal to about 300 µmol/g on average, or greater than or equal to about 350 µmol/g on average.

An upper limit of the ratio $(n^3/w)$ of the number of the moles $(n^3)$ of the substituted or unsubstituted polyalkylene glycol relative to the weight (w) of the nanostructures is not limited, but may be for example, less than or equal to about 1,000 µmol/g on average, less than or equal to about 900 µmol/g on average, less than or equal to about 800 µmol/g on average, less than or equal to about 700 µmol/g on average, or less than or equal to about 600 µmol/g on average.

For example, when the nanostructures do not include the substituted or unsubstituted polyalkylene glycol, the ratio $(n^1/w)$ of the number of the moles $(n^1)$ of the first compound relative to the weight (w) of the nanostructures may be less than or equal to about 60 µmol/g, for example, less than or equal to about 55 µmol/g, less than or equal to about 50 µmol/g, about 1 to about 60 µmol/g, about 5 to about 55 µmol/g, or about 10 to about 50 µmol/g.

Another embodiment of the present disclosure provides a biosensor including the nanostructures. The biosensor may be a affinity-based device using a compound capable of specifically being bound to a biological material, for example, a affinity-based screening library, a biochip capable of analyzing the presence of a biological material, or the like, or a kit including the same.

In addition, the biosensor may further include a substrate supporting the biosensor. The substrate may be transparent or opaque, and may be made of an inorganic material or an organic material. As the transparent substrate, an inorganic substrate such as glass, indium tin oxide (ITO), quartz, alumina, silicon, a carbon material, or an organic substrate made of a transparent polymer may be used. As the opaque substrate, a paper or a substrate made of opaque glass or polymer may be used. The substrate may be used as long as it may support the biosensor without causing a special chemical reaction with the materials constituting the nanostructures supported thereon, and is not limited to those exemplified above.

In addition, the substrate may be made of a magnetic material, or a magnetic material may be included inside or under the substrate. When the substrate includes a magnetic material, the substrate and the nanostructures may be bonded through the magnetism.

When the biosensor is composed of the nanostructures alone, the biosensor may be present in a form of a powder or a solution including the nanostructures. When the biosensor further includes the substrate, the biosensor may exist on the substrate in a form in which the nanostructures are supported in various ways.

Another embodiment of the present disclosure provides a method of screening a biological material using the biosensor.

The biological material may be enzymes, antigens, antibodies, proteins, peptides, carbohydrates, DNA, RNA, and/or portions thereof. The biological material may be, for example, a biomarker of a disease, and is not limited to the materials described above. Since the biological material may be combined with a specific compound to change its biological activity, the compound that is bound to the biological material may be a new drug candidate. Therefore, it is important to develop a drug that is bound to the biological material.

The biological material may be labeled with a labeling material (label), and the labeling material may be an adhesive labeling material. As the biological material is labeled with a labeling material, at affinity-based screening for the biological material, the Hit-nanostructure may be selected through the labeling material. For example, the Hit-nanostructure combined with the biological material labeled with the labeling material may be adhered to the container, and thus the Hit-nanostructure may be selected therefrom. Herein, the container, etc. may be coated with a material that may adhere to the labeling material, a shape of the container is not limited as long as the nanostructures, such as substrates, tubes, or chambers may be applied and/or supported.

Specifically, the labeling material is biotin, histag, Ni-NTA, N-hydroxysuccinmide, amine, thiol, histidine, phosphine, aldehyde tag, hydrazide tag, halide, alkyne, azide, halotag, benzylguanine, sanp tag, benzylcytosine, clip-tag, flag-tag, maleimide, or a combination thereof, but it is not limited thereto.

FIG. 1 is a flowchart schematically illustrating a method of screening a biological material using a biosensor including nanostructures according to an embodiment of the present disclosure.

Referring to FIG. 1, a screening method according to an embodiment includes contacting a biological material with the biosensor. The nanostructures may or may not interact with the biological material. When the nanostructures and the biological material interact, the nanostructures and the biological material may be bound to each other. The interaction site interacted with the biological material in the nanostructures may be a probe.

Thereafter, the screening method may further include selecting nanostructures (Hit-nanostructure) interacted with the biological material in the biosensor. For example, the selecting of the nanostructures (Hit-nanostructure) interacted with the biological material may be detecting the labeling material labeled on the biological material, and selecting the Hit-nanostructure.

When the labeling material is an adhesive labeling material, the selecting of the nanostructures interacted with the biological material may include
preparing a container coated with a material that is bound to the biological material, and
attaching the nanostructures interacted with the biological material to the container. For example, when the labeling material is biotin, the container may be coated with streptavidin.

Accordingly, the Hit-nanostructure alone among the nanostructures is fixed to the surface of the container, so that the Hit-nanostructure may be quickly selected with high efficiency. Therefore, a mass analysis may be possible, and thus the optimal Hit-compound may be selected based on the accumulated results, thereby increasing accuracy and success probability of new drug candidate screening.

Referring to FIG. 1, the screening method may further include identifying a compound (Hit-compound) interacted with the biological material from nanostructures (Hit-nanostructure) interacted with the selected biological material.

The identifying of the compound interacted with the biological material from the nanostructures (Hit-nanostructure) interacted with the biological material may include analyzing a DNA sequence encoding a probe of the second compound. Accordingly, the type, number, and order of the second building blocks constituting the DNA sequence encoding the probe are analyzed to confirm the type, number, and order of the first building blocks encoded by each second building block. Thus, the structure of the compound (Hit-compound) interacted with the biological material may be confirmed.

For example, the identifying of the compound interacted with the biological material from the nanostructures interacted with the selected biological material is
amplifying a DNA sequence of the second compound of the selected nanostructures interacted with the biological material, and
analyzing the amplified DNA sequence.

The amplifying of the DNA sequence of the second compound of the selected nanostructures interacted with the biological material may be performed by a general polymerase chain reaction. For example, a double strand of the DNA coding sequence is denatured into single strands at about 95° C.; by lowering a temperature, a primer having a nucleotide sequence complementary to the DNA single strand or the primer at the end of the DNA single strand is annealed; and by increasing the temperature again, DNA polymerase polymerizes dNTP complementary to the DNA single strand from the 3'-OH end of the primer bound to the DNA single strand to synthesize a DNA double helix. The DNA repeats the cycle of denaturation-annealing-polymerization a certain number of times, and the synthesized DNA double helix may be used as a substrate for the next cycle to amplify the DNA.

The analyzing of the amplified DNA sequence may be performed by Sanger sequencing, next generation sequencing (NGS, etc.), and desirably in next generation sequencing (NGS). Accordingly, by analyzing the type, number, and order of the second building blocks constituting the amplified DNA, and confirming the type, number, and order of the first building blocks encoded by each second building block, the structure of the Hit-compound may be derived. That is, by confirming the structure of the probe that is bound to the biological material, the probe bound to the biological material may be used as a new drug candidate.

Hereinafter, specific embodiments of the present disclosure are described. However, the embodiments described below are merely for illustrating or explaining the present disclosure in detail, and thus the present disclosure should not be limited.

Preparation of Nanostructures

Preparation Example 1: Preparation of Nanostructure 1

Nanostructure 1 may be prepared from Reaction Scheme 1.

Referring to Reaction Scheme 1, Fmoc-AEEP-OH, Boc-γAbu-OH, and MeO-PEG (5,000 Da)-OH as linkers in each amount of 0.60 mg, 0.10 mg, and 15 mg in a mole ratio of 3:1:6 are added to 0.3 mg of a nanoparticle precursor (Tamagawa Seiki Co., Ltd., FG beads, size: 200 nm) having an amino group introduced into the surface, and then reacted therewith. A TFA/DCM mixed solution in a volume ratio of 1:1 is added thereto (a Boc deprotection step), and headpiece DNA to which an amino acid is attached is linked thereto (a second compound linking step). Then, after adding piperidine dissolved in 20 volume % in dimethylformamide (Fmoc deprotection step), leucine-phenylalanine-tryptophan-Ac is added thereto to linked them (first compound linking step), preparing Nanostructure 1.

(wherein, Fmoc: Fluorenylmethyloxycarbonyl, AEEP: [(Amino)ethoxy]ethoxy propionic Acid, γAbu: 4-amino butyric acid, Boc: t-Butyloxycarbonyl, Abu: aminooxyacetic acid, NHS: N-hydroxysuccinimide ester, Ac: acetyl, TFA: trifluoroacetic acid, DCM: dichloromethane)

Figure 2:
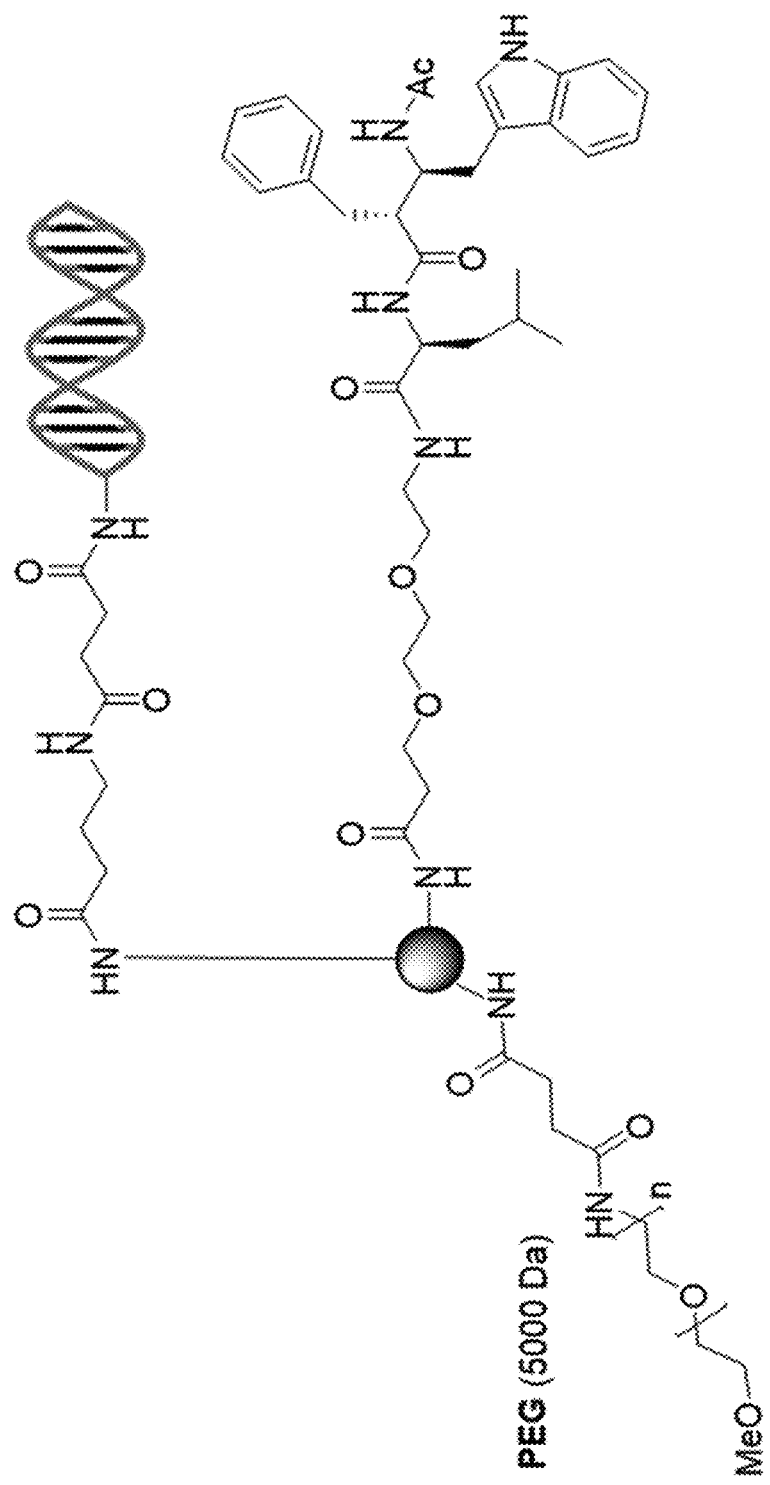
FIG. 2 representatively shows Nanostructure 1 prepared in Preparation Example 1.
Figure 3:
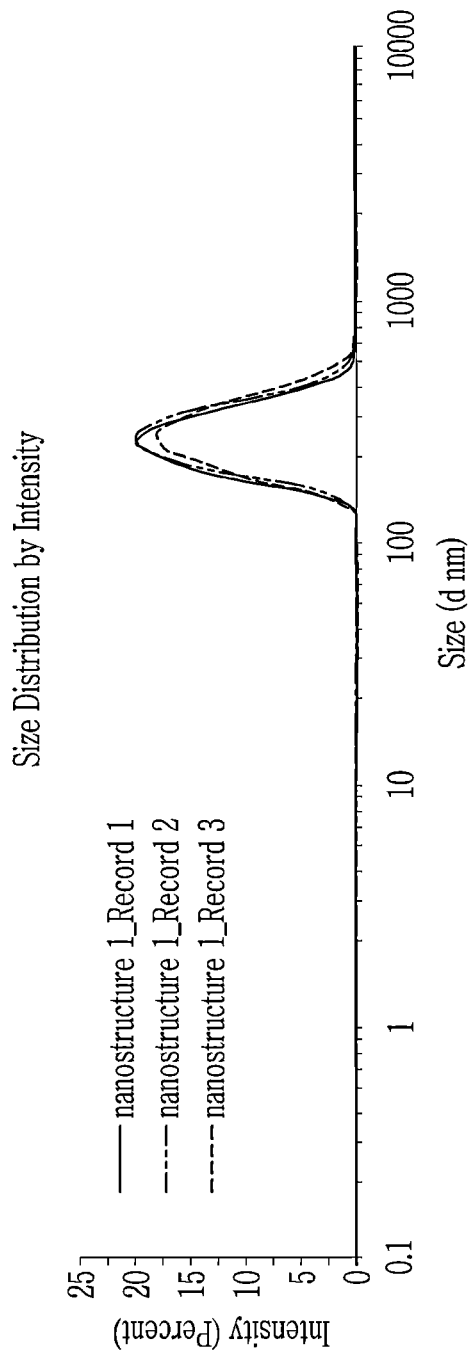
FIGS. 3 to 6 are graphs showing size distributions of Nanostructures 1 to 3 and Comparative Nanostructure 1 prepared in Preparation Examples 1 to 3 and Comparative Preparation Example 1, measured three times by a dynamic light scattering method, respectively.
Figure 4:
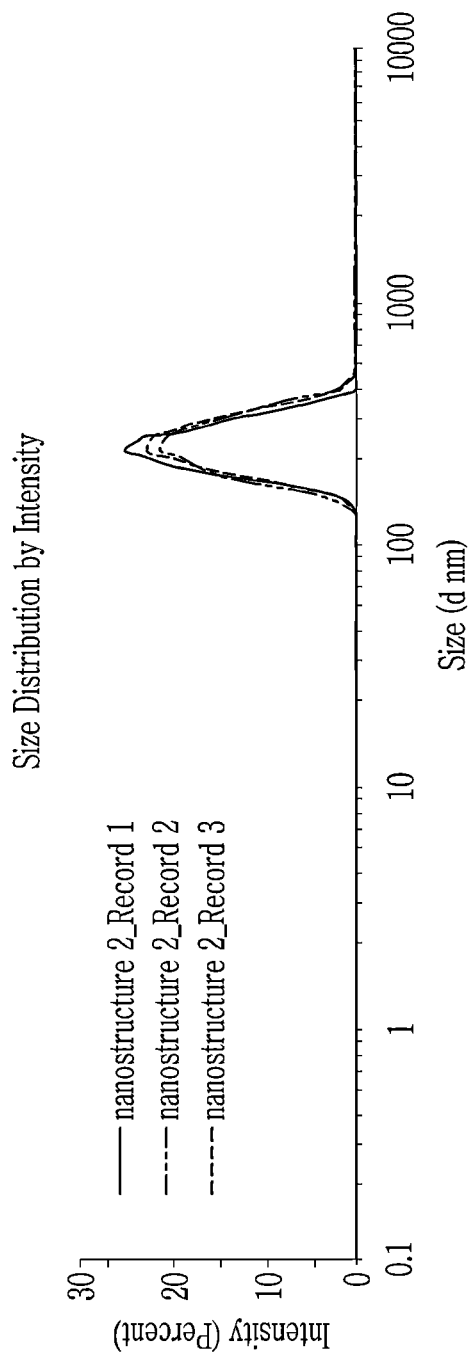
Figure 5:
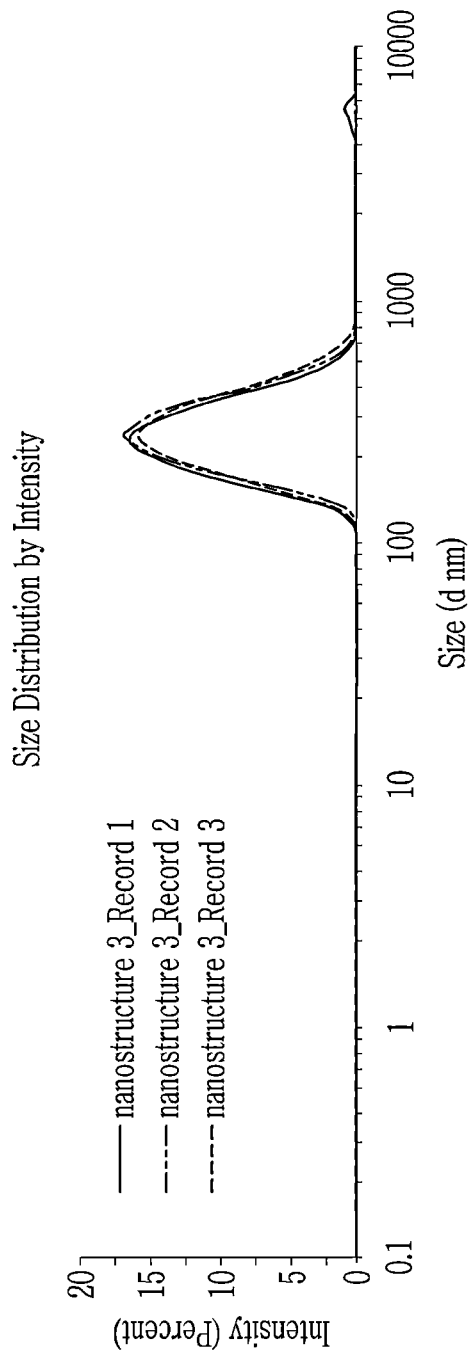
Figure 6:
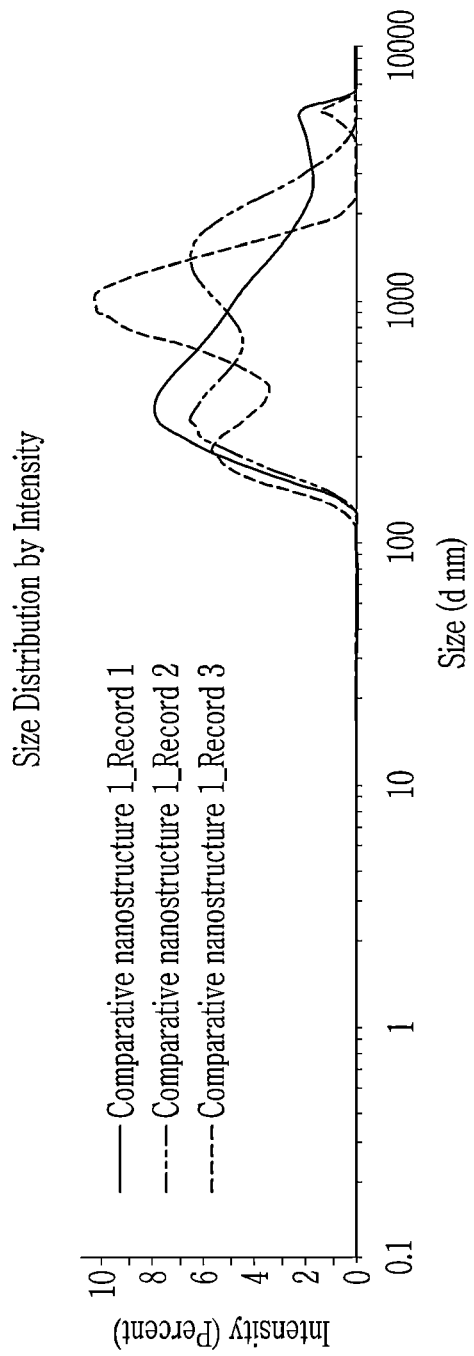

FIG. 2 representatively shows Nanostructure 1 prepared in Preparation Example 1.

[Reaction Scheme 1]
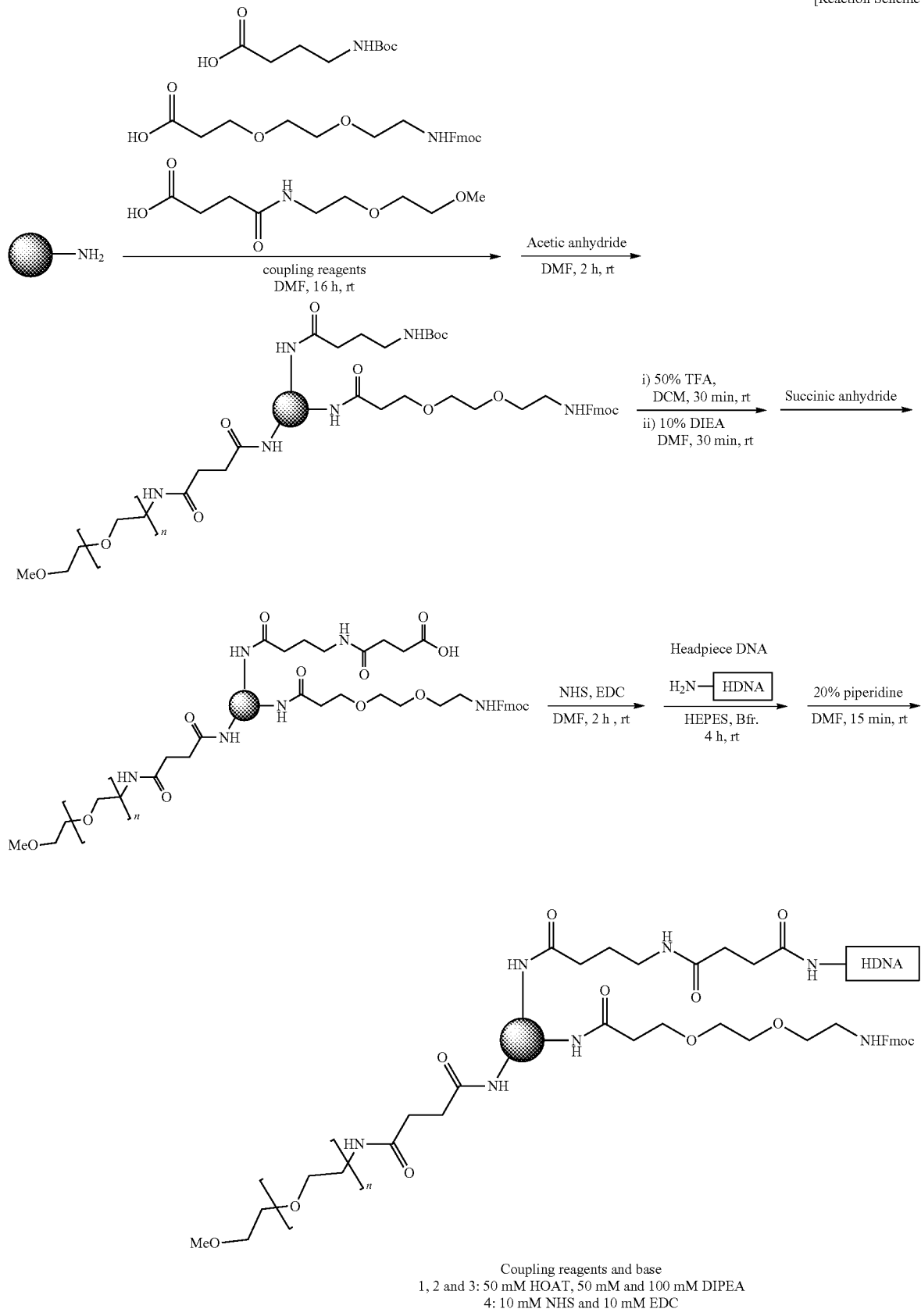

Preparation Example 2: Preparation of Nanostructure 2

Nanostructure 2 is prepared according to the same method as Preparation Example 1 except that Fmoc-Abu-OH, Boc-Abu-OH, and MeO-PEG (5,000 Da)-OH as linkers in each amount of 0.15 mg, 0.025 mg, and 22.5 mg in a mole ratio of 7.5:2.5:90 instead of Fmoc-AEEP-OH, Boc-γ Abu-OH, and MeO-PEG (5,000 Da)-OH as linkers in each amount of 0.60 mg, 0.10 mg, and 15 mg in a mole ratio of 3:1:6.

Preparation Example 3: Preparation of Nanostructure 3

Nanostructure 3 is prepared according to the same method as Preparation Example 1 except that Fmoc-Abu-OH and Boc-Abu-OH as linkers in each amount of 0.30 mg and 0.051 mg in a mole ratio of 75:25 are added instead of Fmoc-AEEP-OH, Boc-γ Abu-OH, and MeO-PEG (5,000 Da)-OH as linkers in each amount of 0.60 mg, 0.10 mg, and 15 mg in a mole ratio of 3:1:6.

Comparative Preparation Example 1: Preparation of Comparative Nanostructure 1

Comparative Nanostructure 1 is prepared according to the same method as Preparation Example 1 except that Fmoc-Abu-OH and Boc-Abu-OH as linkers in each amount of 1.5 mg and 0.25 mg in a mole ratio of 75:25 are added instead of Fmoc-AEEP-OH, Boc-γ Abu-OH, and MeO-PEG (5,000 Da)-OH as linkers in each amount of 0.60 mg, 0.10 mg, and 15 mg in a mole ratio of 3:1:6.

Evaluation 1: Evaluation of Dispersibility of Nanostructures

Dispersibility of the nanostructures is evaluated depending on presence or absence of substituted or unsubstituted polyalkylene glycol bound to the surface of the nanoparticles and surface density of the first and second compounds bound to the surfaces of the nanoparticles.

Evaluation 1-1: First Compound Density on Surface of Nanoparticle

In a method of manufacturing Nanostructures 1 to 3 and Comparative Nanostructure 1 according to Preparation Examples 1 to 3 and Comparative Preparation Example 1, dibenzofulvenepiperidine generated after the Fmoc deprotection step is quantified at 273 nm with a spectrophotometer. The number of moles of the dibenzofulvenepiperidine is the same as the number of moles of the first compound on the surface of the nanostructures, a ratio ($n^1$/w) of the number of moles ($n^1$) of the first compound relative to each weight (w) of Nanostructure 1 to 3 and Comparative Nanostructure 1, a ratio (($n^1+n^2$)/w) of a sum ($n^1+n^2$) of the number of moles ($n^1$) of the first compound and the mol number ($n^2$) of the second compound relative to each weight (w) of the nanostructures, which is calculated therefrom, and a ratio ($n^3$/w) of the mol number ($n^3$) of substituted or unsubstituted polyalkylene relative to each weight (w) of the nanostructures are shown in Table 1.

TABLE 1

|  | Nano-structure 1 | Nano-structure 2 | Nano-structure 3 | Comparative Nano-structure 1 |
| --- | --- | --- | --- | --- |
| Mole ratio of linkers | 3:1:6 | 7.5:2.5:90 | 75:25:0 | 75:25:0 |
| $n^1$/w | 50.2 µmol/g | 30.3 µmol/g | 14.5 µmol/g | 64.2 µmol/g |

TABLE 1-continued

|  | Nano-structure 1 | Nano-structure 2 | Nano-structure 3 | Comparative Nano-structure 1 |
| --- | --- | --- | --- | --- |
| ($n^1+n^2$)/w | 66.9 µmol/g | 40.4 µmol/g | 19.3 µmol/g | 85.6 µmol/g |
| $n^3$/w | 100.6 µmol/g | 363.6 µmol/g | — | — |

Referring to Table 1, Nanostructures 1 and 2 include the substituted or unsubstituted polyalkylene, but Nanostructure 3 includes no substituted or unsubstituted polyalkylene bound to the surface of nanoparticles, and they exhibit low ratios of the sum of the number of moles the first and second compounds relative to the weight of the nanostructures. However, Comparative Nanostructure 1 includes no substituted or unsubstituted polyalkylene bound to the surface of the nanoparticles and exhibits a high ratio of the sum of the number of moles of the first and second compounds relative to the weight of the nanostructures.

Evaluation 1-2: Size Distribution of Nanostructures

Nanostructures 1 to 3 and Comparative Nanostructure 1 according to Preparation Examples 1 to 3 and Comparative Preparation Example 1 are dispersed in 600 µL of TBST buffer saline in each amount of 0.15 mg. Then, sizes of Nanostructures 1 to 3 and Comparative Nanostructure 1 are measured using a dynamic light scattering meter (Malvern zetasizer Z, Malvern Panalytical), and size distributions are shown in FIGS. 3 to 6 and Table 2.

FIGS. 3 to 6 are graphs showing size distributions of Nanostructures 1 to 3 and Comparative Nanostructure 1 measured three times by a dynamic light scattering method, respectively.

TABLE 2

|  | Nano-structure 1 | Nano-structure 2 | Nano-structure 3 | Comparative Nano-structure 1 | Control |
| --- | --- | --- | --- | --- | --- |
| DLS (nm) | 235.5 ± 4.4 | 229.1 ± 3.0 | 246.7 ± 2.6 | 508.2 ± 23.1 | 239.4 ± 1.6 |

Herein, Control is a nanoparticle precursor (Tamagawa Seiki Co., Ltd.), FG beads) used to synthesize Nanostructure 1 to 3 and Comparative Nanostructure 1.

Referring to Table 2, compared with Comparison Nanostructure 1, Nanostructures 1 to 3 have a smaller size and a more uniform size distribution.

Evaluation 1-3: Dispersibility of Nanostructures

Nanostructure 1 to 3 and Comparative Nanostructure 1 according to Preparation Examples 1 to 3 and Comparative Preparation Example 1 are respectively dispersed in Tris-HCl buffer saline, and a size distribution change of the nanostructures after 0 hour, 6 hours, and 16 hours and whether or not the nanostructures are aggregated are examined.

Figure 7:
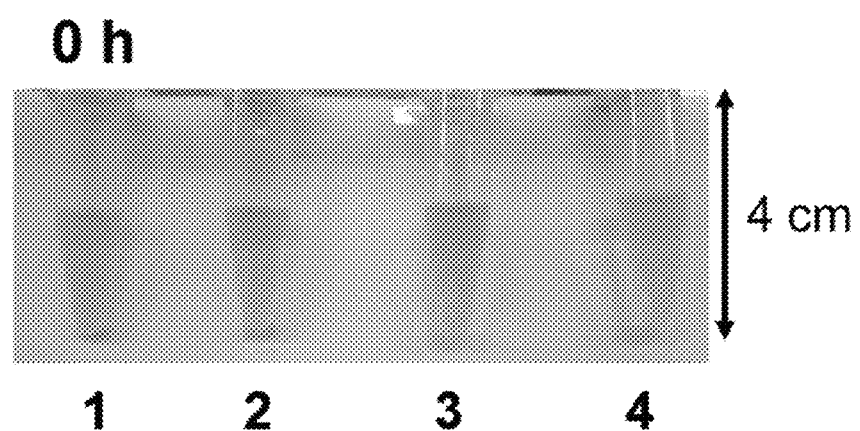
FIGS. 7 to 9 are photographs showing aggregation after 0 hours, 6 hours, and 16 hours of Nanostructures 1 to 3 and Comparative Nanostructure 1 prepared in Preparation Examples 1 to 3 and Comparative Preparation Example 1, respectively.
Figure 8:
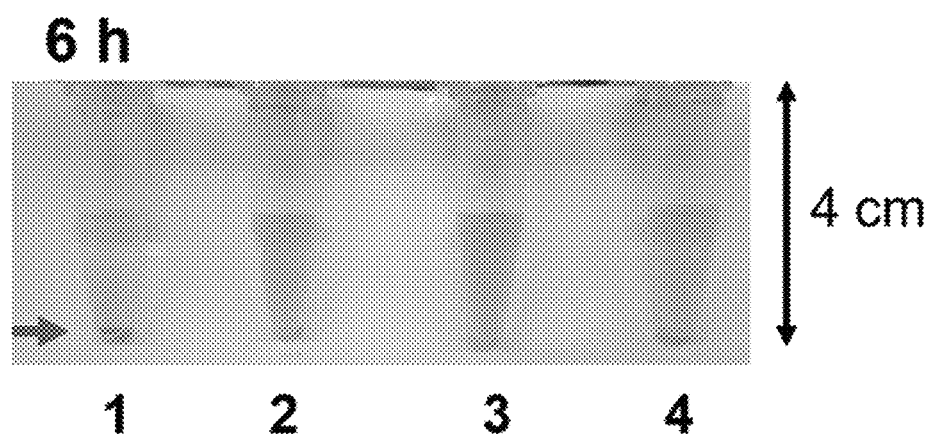
Figure 9:
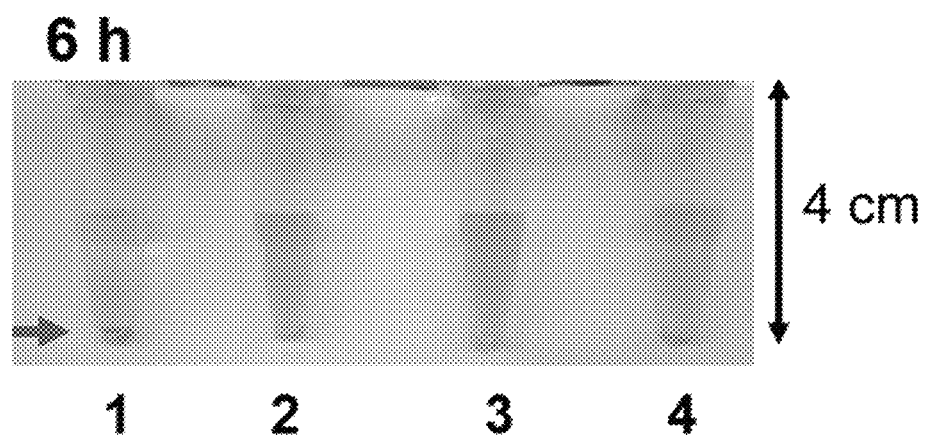

FIGS. 7 to 9 are photographs showing aggregation after 0 hours, 6 hours, and 16 hours of Nanostructures 1 to 3 and Comparative Nanostructure 1.

In FIGS. 7 to 9, 1 are independently photographs showing aggregation of Comparative Nanostructures 1, 2 are independently photographs showing aggregation of Nanostructures 1, 3 are independently photographs showing aggregation of Nanostructures 2, 4 are independently photographs showing aggregation of Nanostructures 3.

Referring to FIGS. 7 to 9, Nanostructures 1 to 3 are not aggregated after these hours, but Comparative Nanostructure 1 is aggregated after 6 hours and 16 hours and thus precipitated.

In summary, Nanostructures 1 and 2 including the substituted or unsubstituted polyalkylene glycol bound to the surface of the nanoparticles according to Preparation Example 1 and Nanostructure 3 including no substituted or unsubstituted polyalkylene glycol bound to the surface of the nanoparticles but having low contents of the first and second compounds bound to the surface of the nanoparticles relative to the nanostructure weight exhibit a small average size and a uniform size distribution and are not aggregated even though time goes.

On the other hand, Nanostructure 3 including no substituted or unsubstituted polyalkylene glycol bound to the surface of the nanoparticles and having high contents of first and second compounds bound to the surface of the nanoparticles exhibits a large average size and a nonuniform size distribution and is aggregated one another as time goes and thus precipitated.

Example 1: Construction of Stapled Peptide Library

By the method of Reaction Scheme 2, a stapled peptide library is constructed based on the alpha-helix structure having a LXXLL motif.

ing the amino acid are alternately synthesized on the surface of the nanoparticles in a split-and-pool method, nanostructures including a first compound including the probe (i.e., peptide) and a second compound including the DNA sequence encoding the probe are synthesized. Lastly, through a copper(I)-catalyzed alkyne-azide cycloaddition (CuAAC), a stapled peptide library is synthesized. The ratio $((n^1+n^2)/w)$ of the sum of the number of moles $(n^1)$ of the first compound and the number of the moles $(n^2)$ of the second compound relative to the weight (w) of the nanostructures is 42.7 µmol/g.

Specifically, the probe is synthesized by using 20 wt % of piperidine dissolved in dimethyl formamide (the Fmoc deprotection step), adding 5-ethynyl-2'-deoxycytidine (EDC) and 1-hydroxy-7-azabenzotriazole (HOAT) thereto, and then, selecting any one of amino acids corresponding to each order in Table 3 and sequentially introducing it in order of the 1$^{st}$ to the 7$^{th}$.

[Reaction Scheme 2]

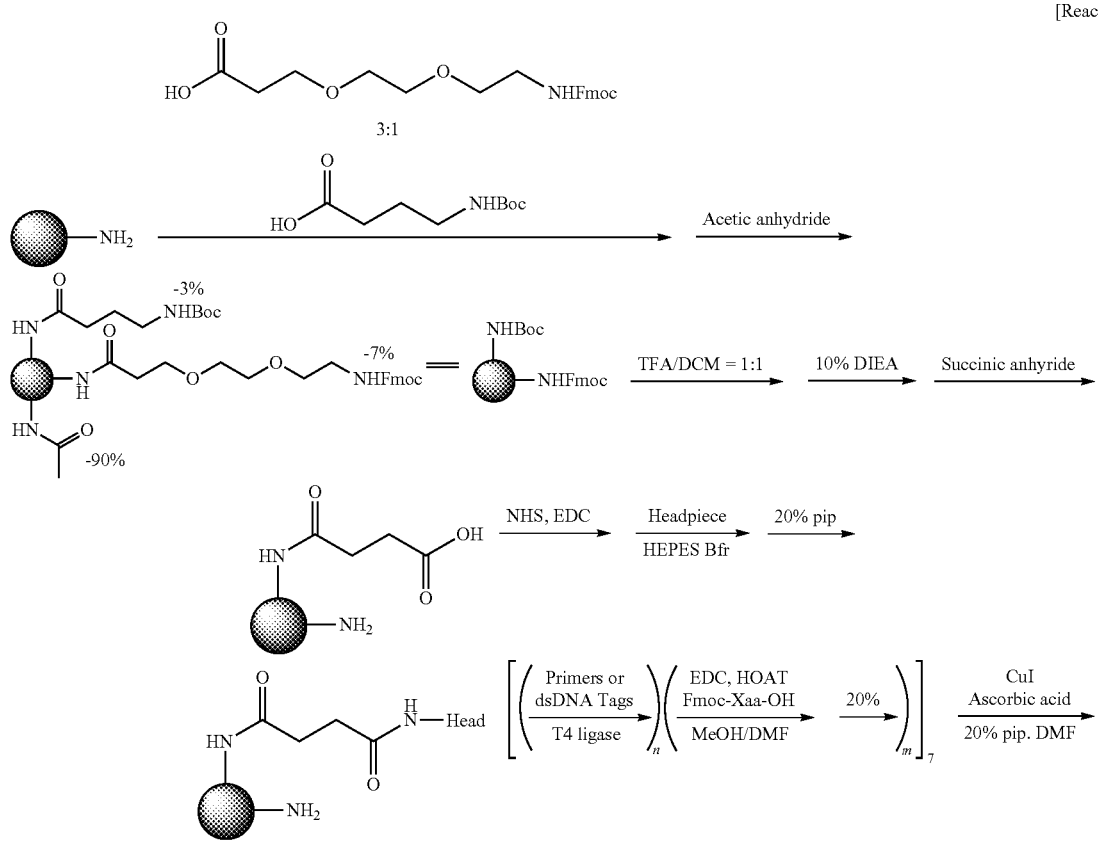

Referring to Reaction Scheme 2, Fmoc-AEEP-OH and Boc-γAbu-OH as linkers in each amount of 3.0 mg and 0.51 mg are respectively added to 5 mg of a nanoparticle precursor (Tamagawa Seiki Co., Ltd., FG beads, size: 200 nm) having an amino group introduced into the surface through an amide linking reaction and then, reacted therewith (a mole ratio of Fmoc-AEEP-OH and Boc-γ Abu-OH: 3:1). Subsequently, while amino acid and a DNA sequence encod-

TABLE 3

| Order | Amino acid |
|---|---|
| 1$^{st}$ | Ala, Leu, Ile, Phe, Ser, Thr, Gln, Tyr, Trp, Arg, Nle, Cha, Nap, $^h$Arg, Phe$^{Cl}$, Aib |
| 2$^{nd}$ | Val, Leu, Ile, Phe, Nle, Cha, Phe$^F$, Phe$^{Cl}$, NaP, Tyr, Trp, $^h$Phe |
| 3$^{rd}$ | Phe, Tyr, Trp, Phe$^F$, Phe$^{Cl}$, Phe$^{NO2}$, $^h$Phe, Arg, $^h$Arg, NaP |

TABLE 3-continued

| Order | Amino acid |
|---|---|
| 4th | Val, Leu, Ile, Phe, Nle, Cha, Phe$^F$, Phe$^{Cl}$, NaP, Tyr, Trp, $^h$Phe |
| 5th | Gly, Ala, Leu, Ile, Phe, Ser, Thr, Gln, Tyr, Trp, Arg, Nle, Cha, Nap, $^h$Arg, Aib |
| 6th | Ala, Leu, Ile, Phe, Ser, Thr, Gln, Tyr, Trp, Arg, Nle, Cha, Nap, $^h$Arg, Phe$^{Cl}$, Aib |
| 7th | DNA sequence of 8ds encoding stapling position |

In Table 3, the 8ds DNA sequence encoding the stapling position may be appropriately selected by those skilled in the art, and is not particularly limited.

The DNA sequence encoding the probe is synthesized by using a TFA/DCM mixed solution in a volume ratio of 1:1 to deprotect Boc, introducing a carboxyl group thereinto and then, dsDNA (i.e., a headpiece) into which an amino group is introduced, and then, introducing a forward primer, the DNA sequence encoding the amino acid, and a reverse primer as a T4-linking enzyme. Herein, the DNA sequence encoding the amino acid has a double helix structure and includes a sticky end having three bases at 3' and 5' terminal ends, and seven base pairs respectively encode the amino acid.

Figure 10:
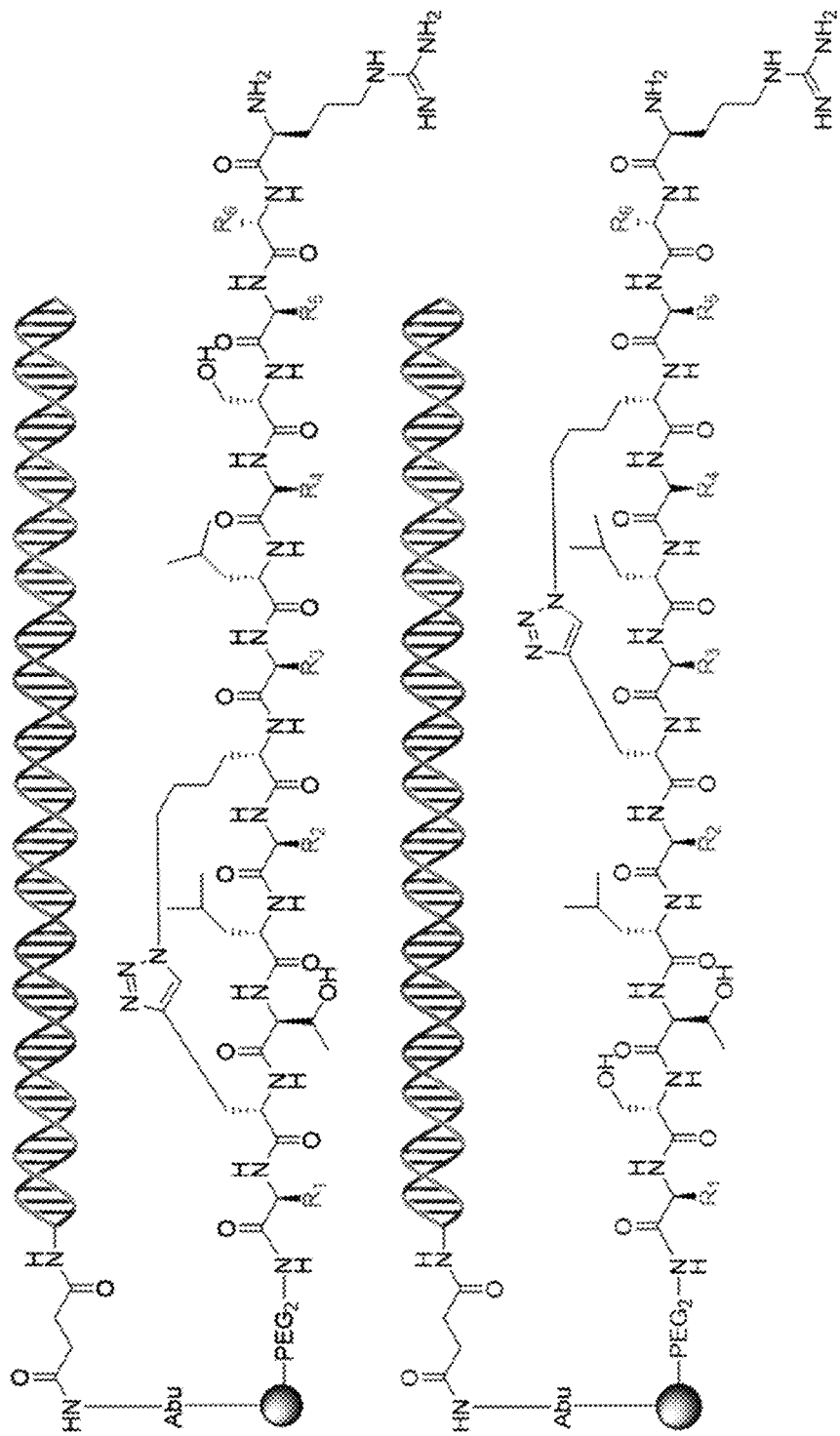
FIG. 10 schematically shows a structure of the nanostructure of the stapled peptide library according to Example 1.

FIG. 10 schematically shows a structure of the nanostructure of the stapled peptide library, and in FIG. 10, $R_n$ is a monovalent group derived from one of amino acids described in order, n of Table 3.

Figure 11:
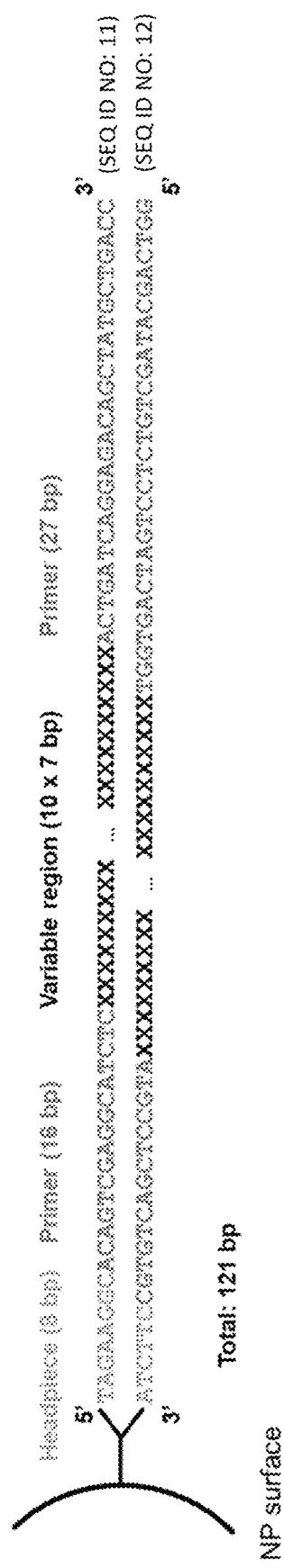
FIG. 11 schematically shows a second compound of nanostructures of the stapled peptide library according to Example 1.

FIG. 11 schematically illustrates a second compound including a DNA sequence encoding the probe.

Accordingly, the stapled peptide library manufactured according to Example 1 includes 16×12×10×12×16×16×2=11,796,480 (about 12,000,000) stapled peptides which are different one another.

Evaluation 2-1: Gel Electrophoresis of Stapled Peptide Library

The DNA sequence encoding the probe of the nanostructures of the stapled peptide library according to Example 1 is amplified through a polymerase chain reaction and then, electrophoresed in acrylamide gel, and the results are examined.

Specifically, the polymerase chain reaction is performed by mixing 1 μL of nanostructures, 0.4 μM forward primer (TAGAAGGCACAGTCGAGGCATCTC (SEQ ID NO: 155)), and 0.4 μM reverse primer (GGTCAGCATAGCTGTCTCCTGATCAG (SEQ ID NO: 156)) which are dispersed in 0.05% Tween-20 (Georgiachem Co., Ltd.) aqueous solution at each concentration of 25, 2.5 and 0.25 μg/mL with 50 μL of premixed PCR solution (HelixAmp™ Ready-2x-Go, Nanohelix). The cycle of the polymerase chain reaction proceeded with [95° C. 10 s, 60° C. 10 s, 72° C. 10 s]×35, and 72° C. 5 min.

Specifically, the electrophoresis is performed on an 8% acrylamide gel, and development with size marker (Tech & Innovation, 50 bp ladder) on TBE (Tris-borate-EDTA) buffered saline at 130 V is performed.

Figure 12:
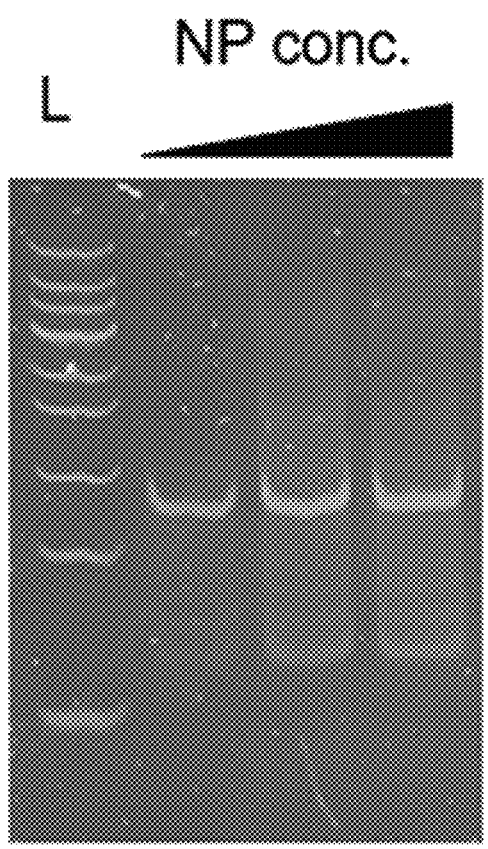
FIG. 12 is a photograph showing results of amplification by PCR of DNA sequences encoding probes of the nanostructures of the stapled peptide library according to Example 1 and electrophoresis on an acrylamide gel.

FIG. 12 is a photograph showing results of amplification by PCR of DNA sequences encoding probes of the nanostructures of the stapled peptide library according to Example 1 and electrophoresis thereof in an acrylamide gel.

Referring to FIG. 12, in the nanostructures in the stapled peptide library according to Example 1, the DNA sequence encoding the probe has a uniform size.

Evaluation 2-2: Dispersibility of Nanostructures of Stapled Peptide Library

Dispersibility of the nanostructures of the stapled peptide library is evaluated by using a transmission electron microscope (TEM, JEOL JEM-2100 Electron Microscope), and their sizes and size distributions are measured in a dynamic light scattering method and evaluated.

First, the nanostructures of the stapled peptide library according to Example 1 are dispersed in a methanol/water (1:1) solution, and the results are confirmed by TEM.

Figure 13:
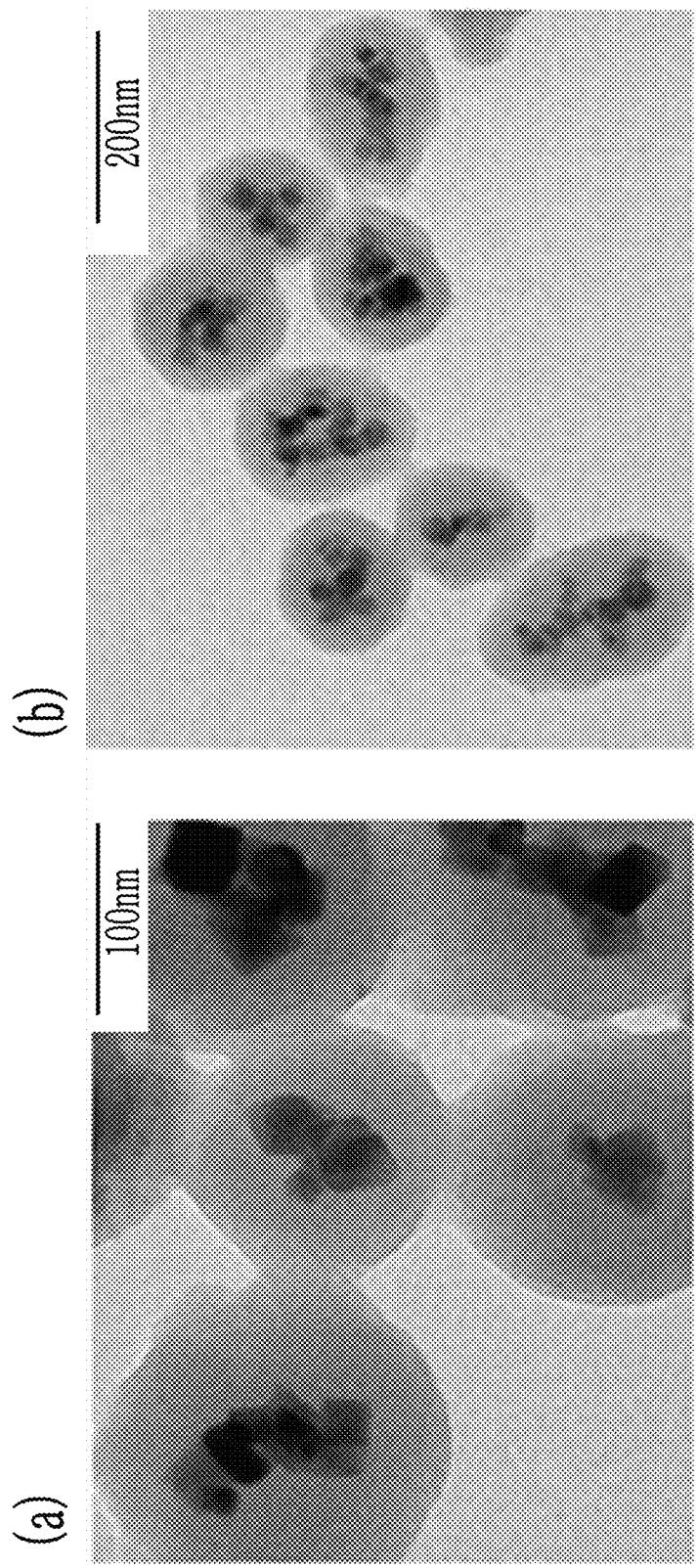
FIGS. 13 (a) and (b) are photographs of the nanostructures of the stapled peptide library according to Example 1 dispersed in a methanol/water (1:1) solution by TEM.

FIGS. 13 (a) and (b) are photographs of the nanostructures of the stapled peptide library according to Example 1 dispersed in methanol/water (1:1) by TEM.

In addition, 0.5 mg of the nanostructures of the stapled peptide library according to Example 1 is dispersed in 0.05% Tween-20 (Georgiachem Co., Ltd., Tween-20) solution, and dimethylformamide (DMF), respectively, and a dynamic light scattering meter (Malvern zetasizer Z, Malvern Panalytical) to measure sizes. The size distributions are shown in Table 4 and FIG. 14.

TABLE 4

| Solvent | 0.05% Tween-20 | DMF |
|---|---|---|
| DLS (nm) | 404.8 ± 4.4 | 310.2 ± 0.9 |

Figure 14:
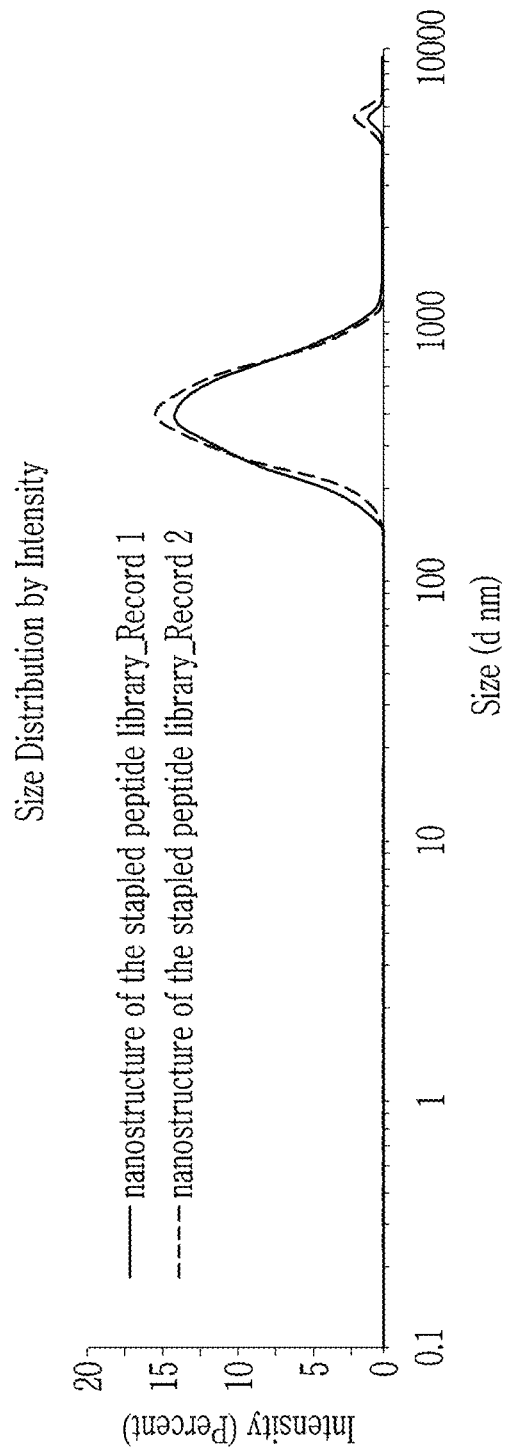
FIG. 14 is a graph showing size distributions in 0.05% Tween-20 solution, and dimethylformamide (DMF) of the nanostructures of the stapled peptide library according to Example 1, measured two times by a dynamic light scattering method, respectively.

FIG. 14 is a graph showing the size distributions of the nanostructures of the stapled peptide library according to Example 1 in the 0.05% Tween-20 solution and dimethylformamide (DMF), measured two times by a dynamic light scattering method, respectively.

Referring to FIGS. 13 and 14 and Table 4, the nanostructures of the stapled peptide library according to Example 1 are not aggregated in methanol/water (1:1), 0.05% Tween-20 (Georgiachem Co., Ltd.) solution, and the dimethyl formamide (DMF) and exhibit uniform size distributions.

In summary, the nanostructures of the stapled peptide library according to Example 1 have a DNA sequence encoding a uniform sized probe. In addition, the nanostructures of the stapled peptide library according to Example 1 have a uniform size and are not aggregated to one another. On the other hand, an alpha-helix structure having a LXXLL motif is known to be overexpressed in various cancers such as a breast cancer, a pancreatic cancer, and the like and thus bonded with a liver receptor homolog-1 (LRH-1). Accordingly, the stapled peptide library based on the alpha-helix structure having the LXXLL motive according to Example 1 may be used to find a new drug candidate bonded with LRH-1 with high accuracy.

Example 2: Preparation of Peptoid Library

By the following method of Reaction Scheme 3, a peptoid library is constructed.

[Reaction Scheme 3]

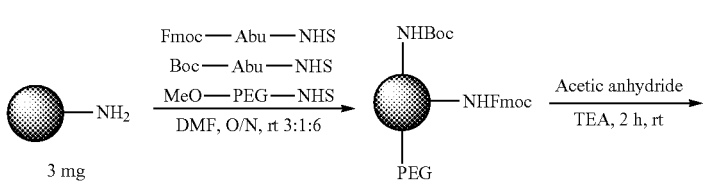

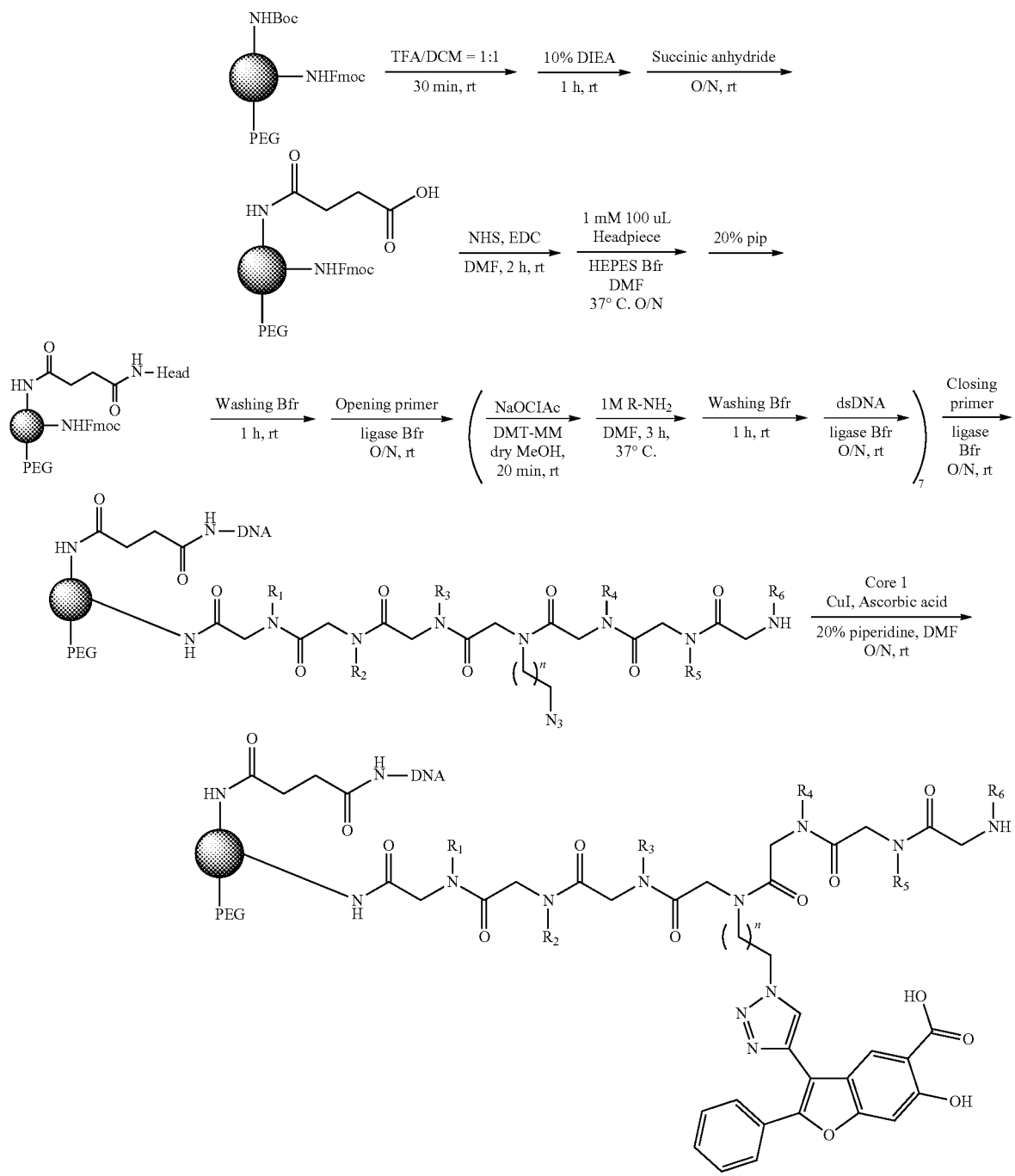

Referring to Reaction Scheme 3, Fmoc-γ Abu-OH, Boc-γ Abu-OH, and polyethylene glycol (PEG, 5,000 Da) in each amount of 0.59 mg, 0.12 mg and 18 mg are respectively added to 3 mg of a nanoparticle precursor (Tamagawa Seiki Co., Ltd., FG beads, size: 200 nm) having an amino group introduced into the surface through an amide linking reaction and then, reacted therewith (a mole ratio of Fmoc-γ Abu-OH, Boc-γ Abu-OH, and PEG=3:1:6). Subsequently, while N-alkylated glycine and a DNA sequence encoding the N-alkylated glycine are alternately synthesized on the surface of nanoparticles in a split-and-pool method, nanostructures including the first compound including the probe (i.e., peptoid), the second compound including the DNA sequence encoding the probe, and PEG are synthesized. Lastly, the peptoid library is synthesized by introducing a compound represented by Chemical Formula 5 (Core 1) into 4th N-alkylated glycine having an azide group through a copper (I)-catalyzed alkyne-azide cycloaddition (CuAAC).

[Chemical Formula 5]

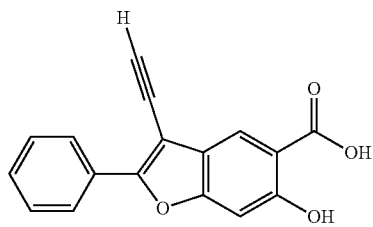

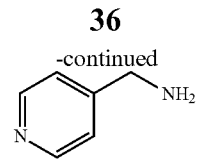

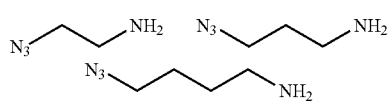

Specifically, the probe is synthesized by seven times repeating a Sub-monomer synthesis step of removing a Fmoc protecting group, adding sodium chloroacetate and 4-(4,6-dimethoxy-1,3,5-triazine-2-yl) 4-methoxymorpholinium chloride (DMT-MM) to chloroacetylate the amino group, adding one primary amine compound corresponding to each order of Table 5 to synthesize N-alkylated glycine in order of the $1^{st}$ to the $7^{th}$.

TABLE 5

| Order | Primary amine compound |
|---|---|
| $1^{th}$ to $3^{rd}$ and $5^{th}$ to $7^{th}$ | Group 1-1 |
| $4^{th}$ | Group 1-2 |

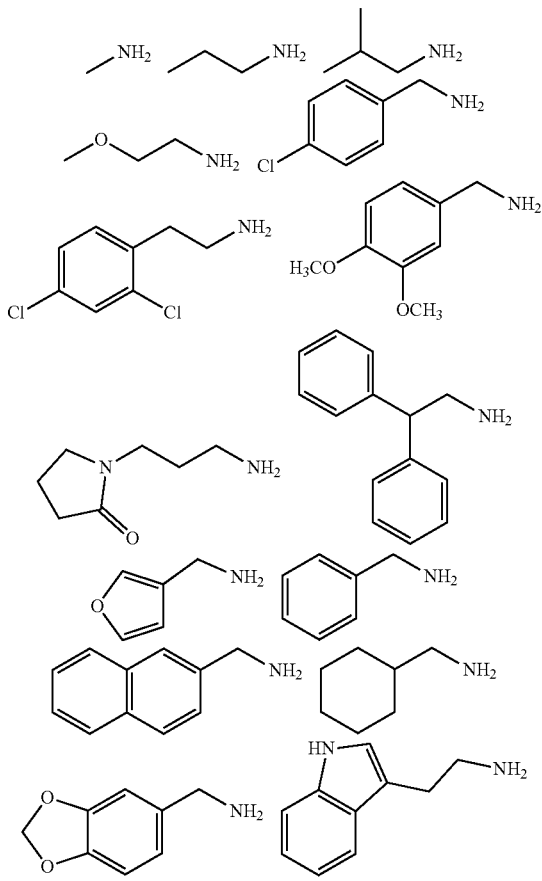

A specific synthesis process of the DNA sequence encoding the probe and a structure of the second compound including the DNA sequence encoding the probe are the same as Example 1.

Figure 15:
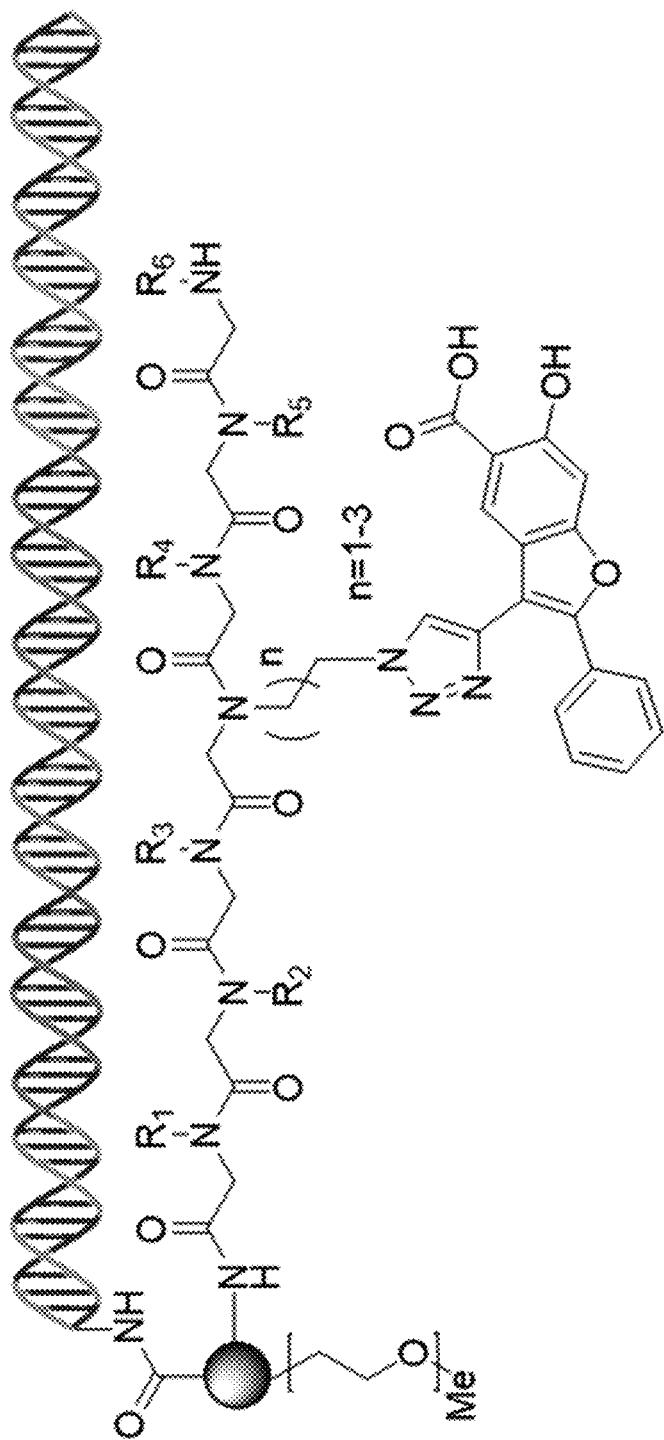
FIG. 15 schematically shows a structure of the nanostructure of the peptoid library according to Example 2.

FIG. 15 schematically shows a structure of the nanostructure of the synthesized peptoid library, and in FIG. 15, $R_n$ is a monovalent group derived from one of primary amine compounds described in order n of Table 5.

Accordingly, the peptoid library according to Example 2 includes $3 \times 16^6 = 50,331,648$ peptoids which are all different one another.

Evaluation 3-1: Gel Electrophoresis of Peptoid Library

The DNA sequence encoding the probe of the nanostructure of the peptoid library according to Example 2 is amplified through a polymerase chain reaction and electrophoresed in an acrylamide gel, and the result is examined.

Specifically, the polymerase chain reaction is performed by mixing 1 μL of nanostructures, 0.4 μM forward primer (TAGAAGGCACAGTCGAGGCATCTC (SEQ ID NO: 157)), and 0.4 μM reverse primer (GGTCAGCATAGCTGTCTCCTGATCAG (SEQ ID NO: 158)) which are dispersed in 0.05% Tween-20 (Georgiachem Co., Ltd.) aqueous solution at each concentration of 20, 2.0, and 0.20 μg/mL with 50 μL of premixed PCR solution (HelixAmp™ Ready-2x-Go, Nanohelix). The cycle of the polymerase chain reaction proceeded with [95° C. 10 s, 60° C. 10 s, 72° C. 10 s]×35, and 72° C. 5 min.

Specifically, the electrophoresis is performed on an 8% acrylamide gel, and development with size marker (Thermo Fisher Scientific, GeneRuler 1 kb Plus DNA Ladder) buffered saline at 130 V is performed.

Figure 16:
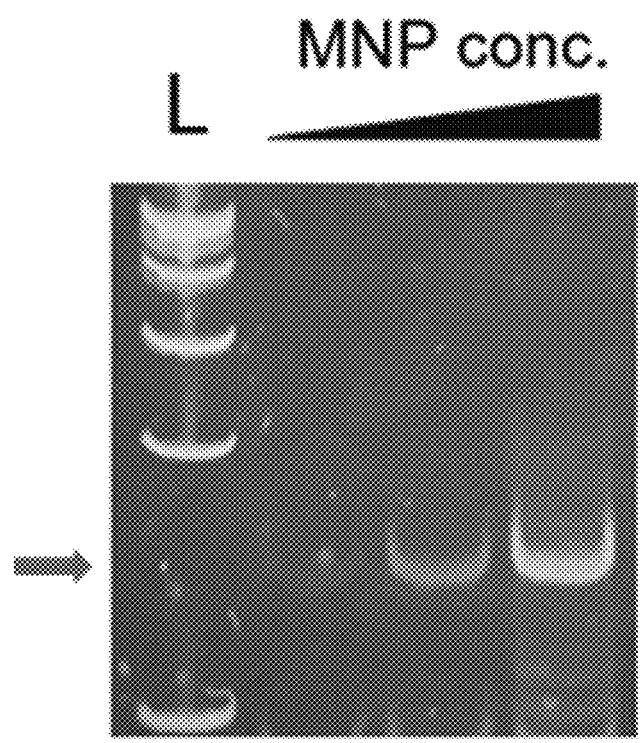
FIG. 16 is a photograph showing the results of amplification by PCR of a DNA sequence encoding a probe of the peptoid library nanostructure according to Example 2 and electrophoresis on an acrylamide gel.

FIG. 16 is a photograph showing the results of amplification of a DNA sequence encoding a probe of the peptoid library nanostructure according to Example 2 by PCR and electrophoresis thereof on an acrylamide gel.

Referring to FIG. 16, the DNA sequence encoding the probe in the nanostructures of the peptoid library according to Example 2 has a uniform size.

Evaluation 3-2: Dispersibility of Nanostructures of Peptoid Library

The dispersibility of the nanostructures of the peptoid library is evaluated by using a photographing with a transmission electron microscope (TEM, JEOL JEM-2100 Electron Microscope), and a dynamic light scattering method is used to measure their sizes and evaluate the size distributions.

First, the nanostructures of the peptoid library according to Example 2 are dispersed in a methanol/water (1:1) solution and a result thereof is examined with TEM.

Figure 17:
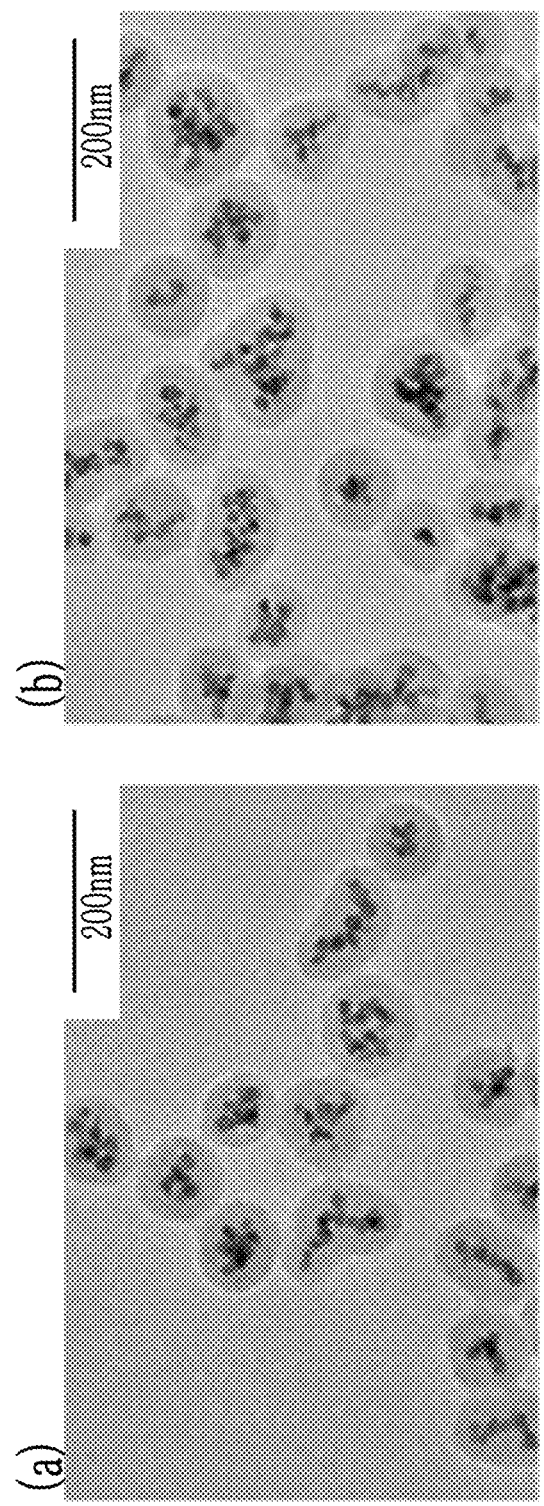
FIGS. 17 (a) and (b) are TEM photographs of the nanostructures of the peptoid library according to Example 2 dispersed in a methanol/water (1:1) solution.

FIGS. 17 (a) and (b) are TEM photographs of the nanostructures of the peptoid library dispersed in a methanol/water (1:1) solution.

In addition, 0.15 mg of the nanostructures of the peptoid library according to Example 2 is dispersed in 700 μL of TBST buffered saline, and the sizes are measured using a dynamic light scattering meter (Malvern zetasizer Z, Malvern Panalytical). The size distributions are shown in Table 6 and FIG. 18.

TABLE 6

| Solvent | TBST |
|---------|------|
| DLS (nm) | 315.9 ± 6.1 |

Figure 18:
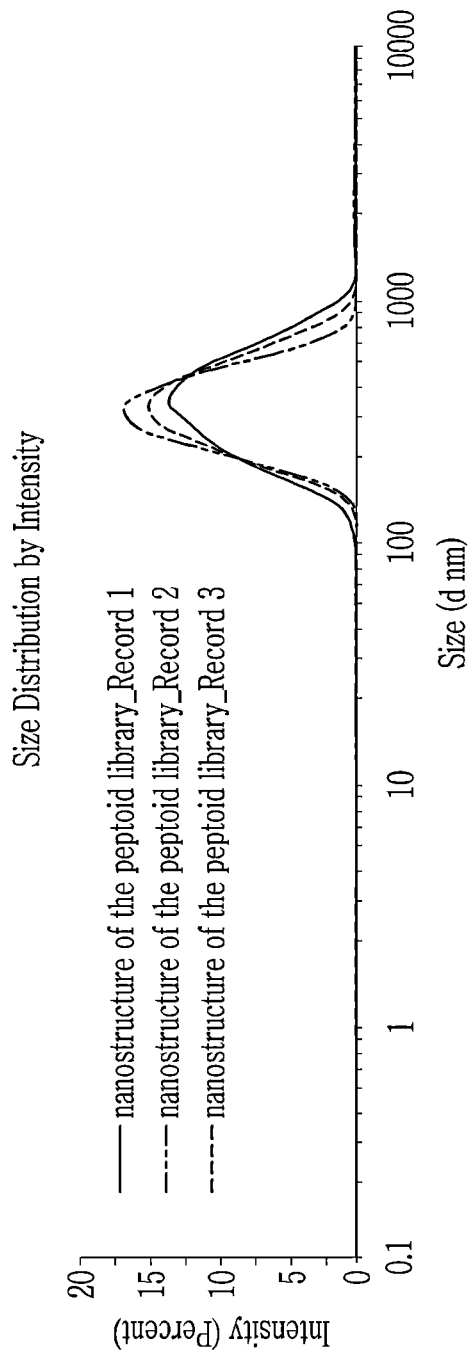
FIG. 18 is a graph showing size distributions in Tris-HCl buffer saline of the nanostructures of the peptoid library according to Example 2, measured three times by a dynamic light scattering method, respectively.

FIG. 18 is a graph showing the size distribution in tris-HCl buffer saline of the nanostructures of the peptoid library according to Example 2, measured three times by a dynamic light scattering method, respectively.

Referring to FIGS. 17 and 18 and Table 6, the nanostructures of the peptoid library according to Example 2 are not aggregated in Tris-HCl buffered saline and exhibit a uniform size distribution.

In summary, the nanostructures of the peptoid library according to Example 2 have a DNA sequence encoding the uniformly sized probe. In addition, the nanostructures of the peptoid library according to Example 2 have a uniform size and are not aggregated to one another.

On the other hand, the compound represented by Chemical Formula 5 (Core 1) is known to weakly stick to an active site of a protein tyrosine phosphatase (PTP). In addition, the peptoid has higher cell permeability and higher stability against a proteolytic enzyme than peptide and the like. Accordingly, by using the peptoid library according to Example 2 based on a peptoid having a moiety derived from Core 1, new drug candidates having high cell permeability, high stability against proteolytic enzymes, and the like, while bound to PTP can be found with high accuracy.

Example 3: Construction of Alpha-Helix Analogue Library Having Triazine-Piperazine-Triazine Backbone By the method of Reaction Scheme 4, an alpha-helix analogue library having a triazine-piperazine-triazine backbone is constructed.

[Reaction Scheme 4]

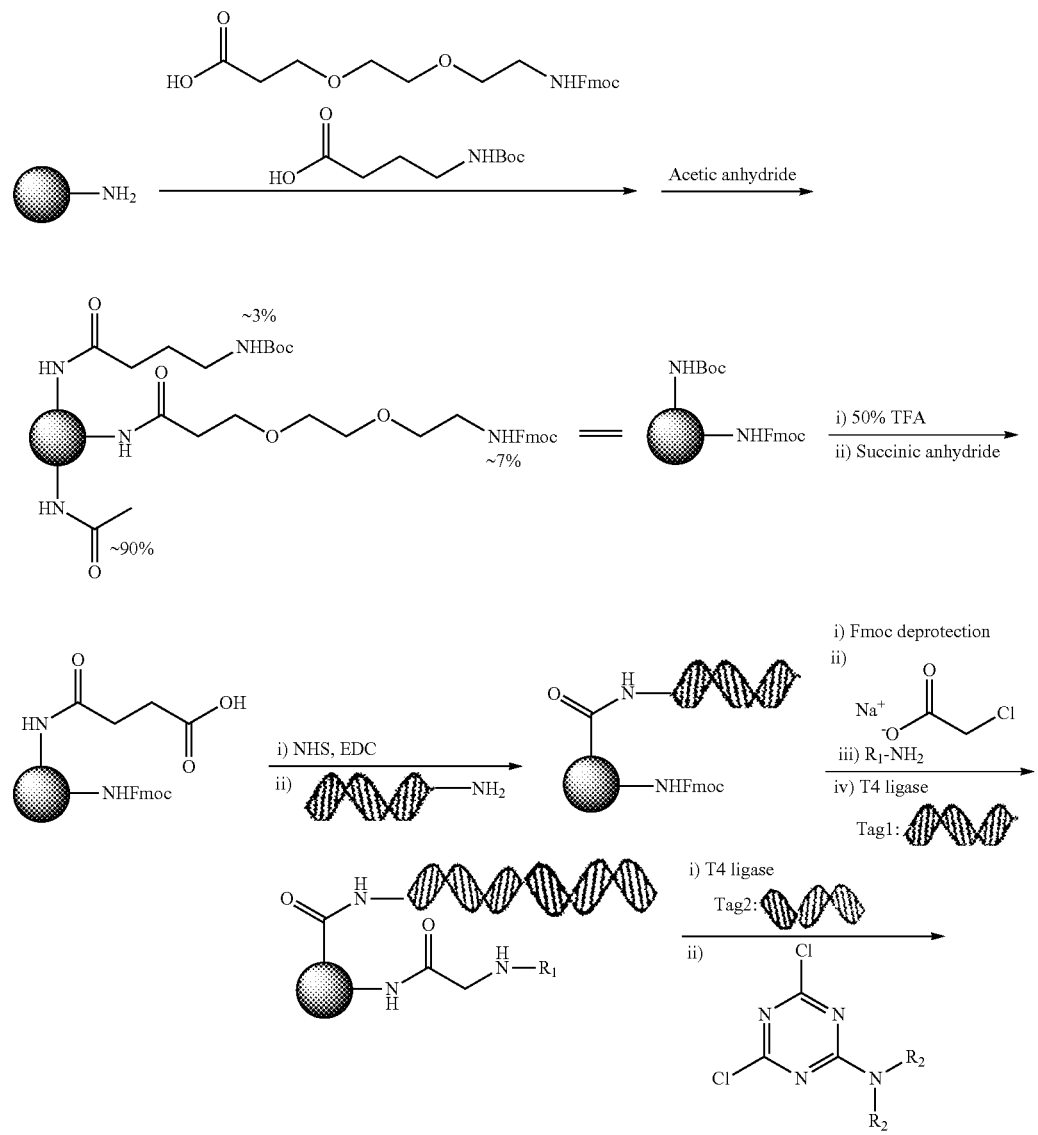

-continued
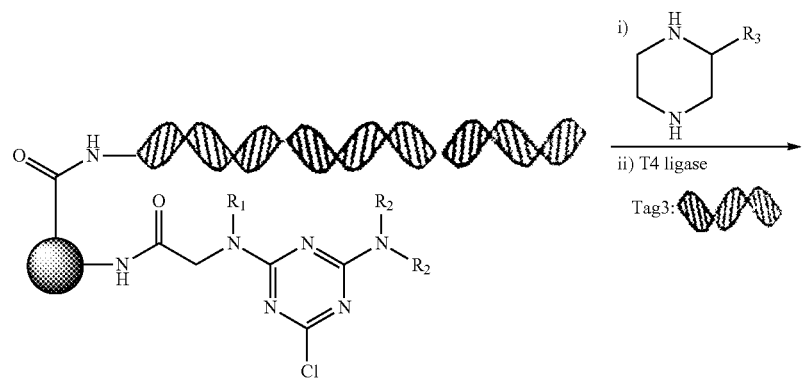
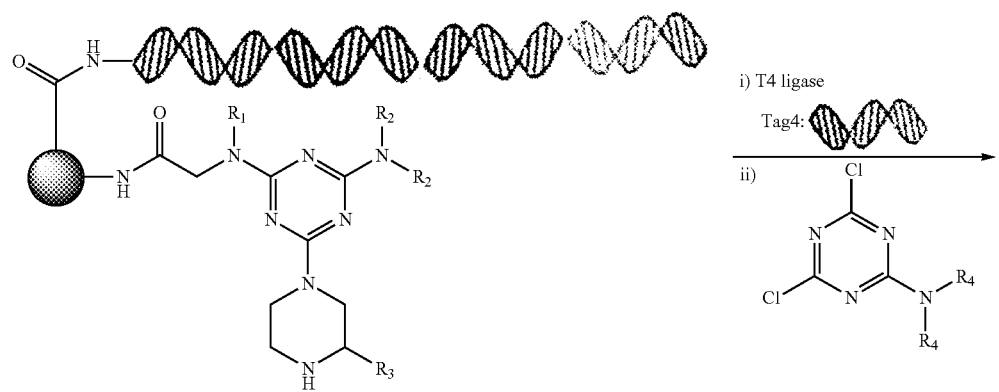
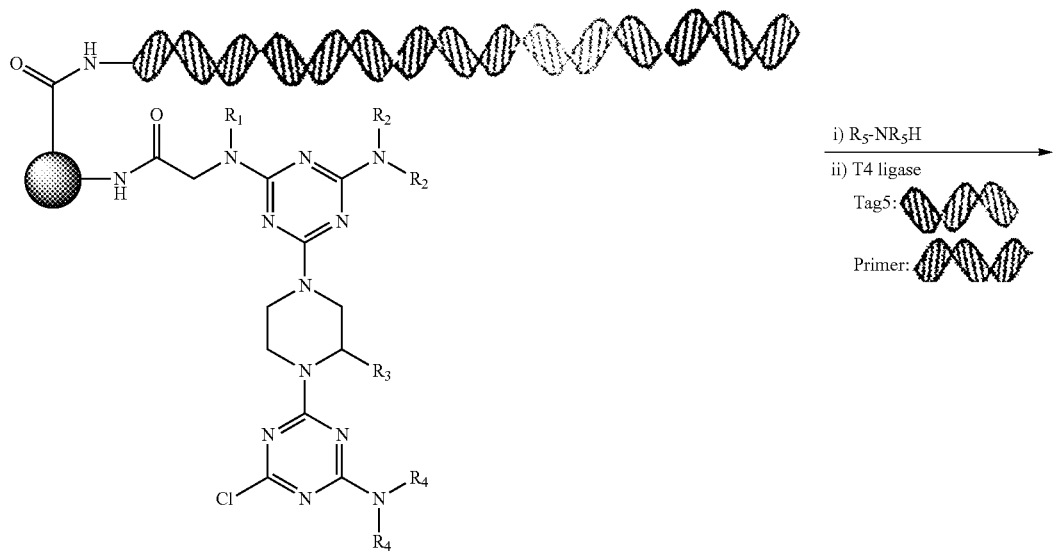

-continued

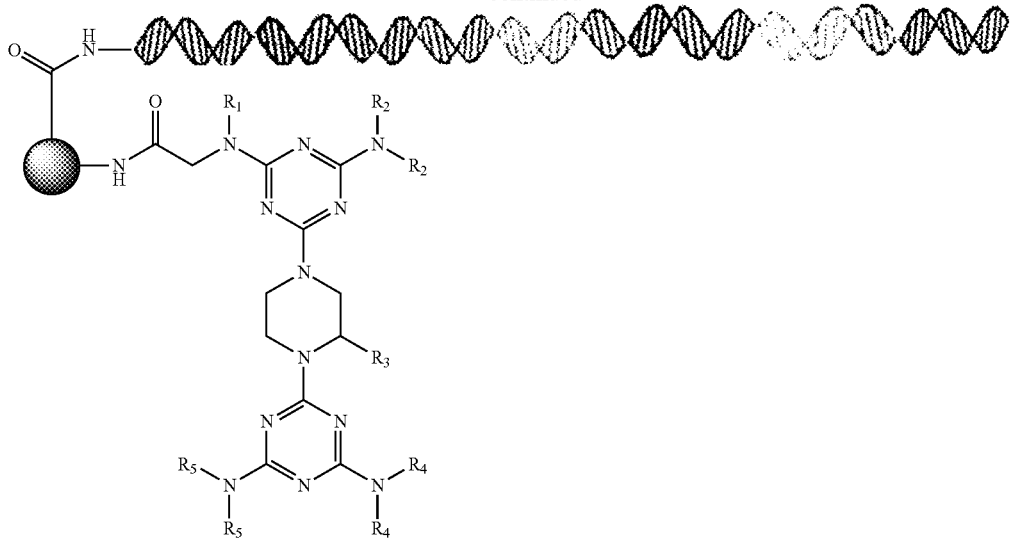

Referring to Reaction Scheme 4, Fmoc-Abu-NHS and Boc-Abu-NHS linkers in each amount of 0.090 mg and 0.015 mg are respectively added to 2.1 mg of a nanoparticle precursor (Tamagawa Seiki Co., Ltd., FG beads, size: 200 nm) having an amino group introduced into the surface through an amide linking reaction and then, reacted therewith (a mole ratio of Fmoc-Abu-NHS and Boc-Abu-NHS: 3:1). Subsequently, while a substituted or unsubstituted amine, a substituted or unsubstituted triazine, and a substituted or unsubstituted piperazine; and a DNA sequence encoding them are alternately synthesized in a split-and-pool method, nanostructures including the first compound including the probe (i.e., an alpha-helix analogue having a triazine-piperazine-triazine backbone) and the second compound including the DNA sequence encoding the probe are synthesized. The ratio $((n^1+n^2)/w)$ of the sum of the number of moles $(n^1)$ of the first compound and the number of the moles $(n^2)$ of the second compound relative to the weight (w) of the nanostructure is 31.9 μmol/g.

First, a sequence encoding the probe is synthesized by deprotecting Boc, introducing a carboxyl group thereinto, then, introducing dsDNA into which an amino group is introduced (a headpiece), and introducing a forward primer; a DNA sequence encoding the substituted or unsubstituted amine, the substituted or unsubstituted triazine, and the substituted or unsubstituted piperazine; and a reverse primer by T4 ligase. Herein, the DNA sequence encoding the substituted or unsubstituted amine, the substituted or unsubstituted triazine, and the substituted or unsubstituted piperazine has a double helix structure and includes a sticky end consisting of three bases at each 3' and 5' terminal end, and seven base pairs encode each substituted or unsubstituted amine, substituted or unsubstituted triazine, and substituted or unsubstituted piperazine.

The probe is synthesized by selecting one corresponding to each order in Table 7 after deprotecting Fmoc and then, sequentially introducing it in order of the $1^{st}$ to the $5^{th}$.

TABLE 7

| Order | Substituted or unsubstituted amine/ substituted or unsubstituted triazine/ substituted or unsubstituted piperazine |
|---|---|
| $1^{st}$ | Group 2 |
| $2^{nd}$ | Group 4 |
| $3^{rd}$ | Group 5 |
| $4^{th}$ | Group 4 |
| $5^{th}$ | Group 3 |

[Group 2]

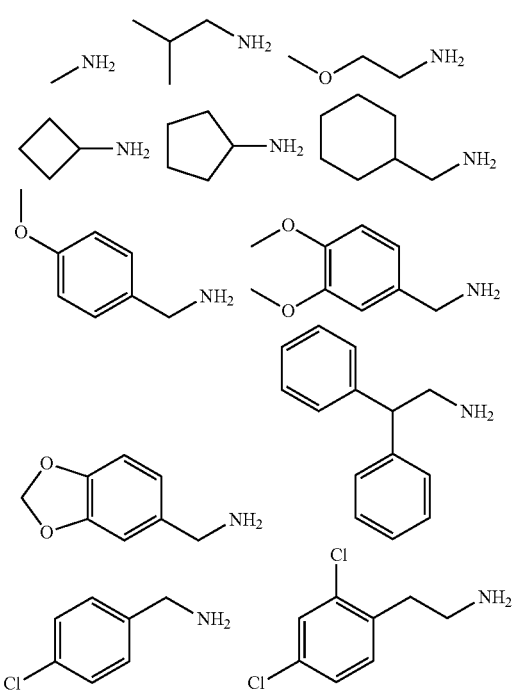

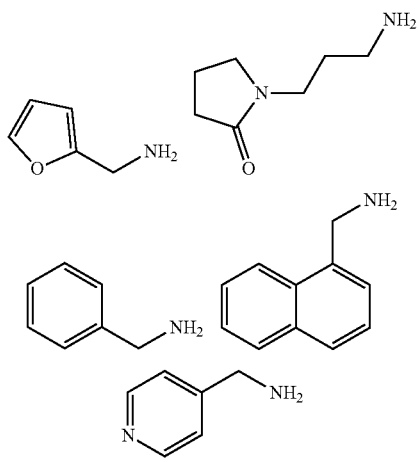
[Group 3]
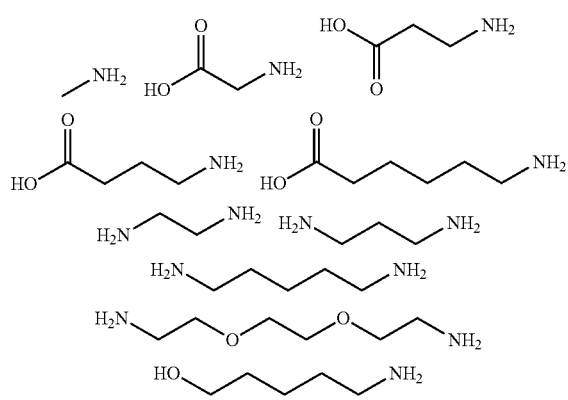
[Group 4]
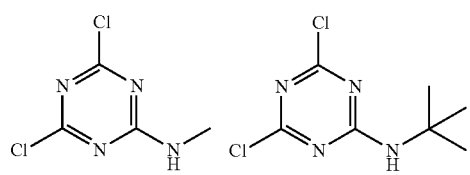
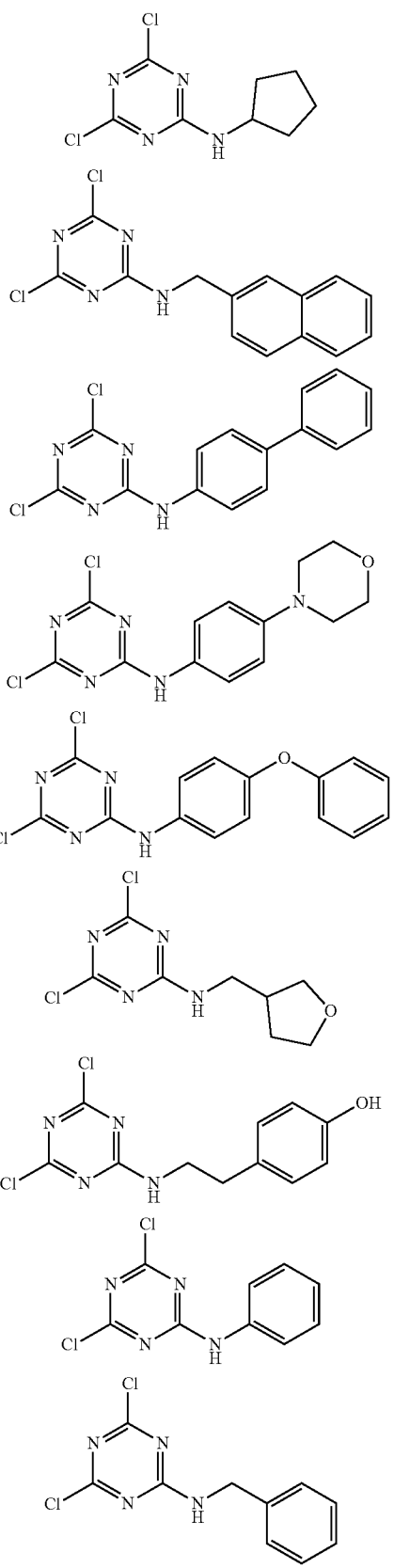

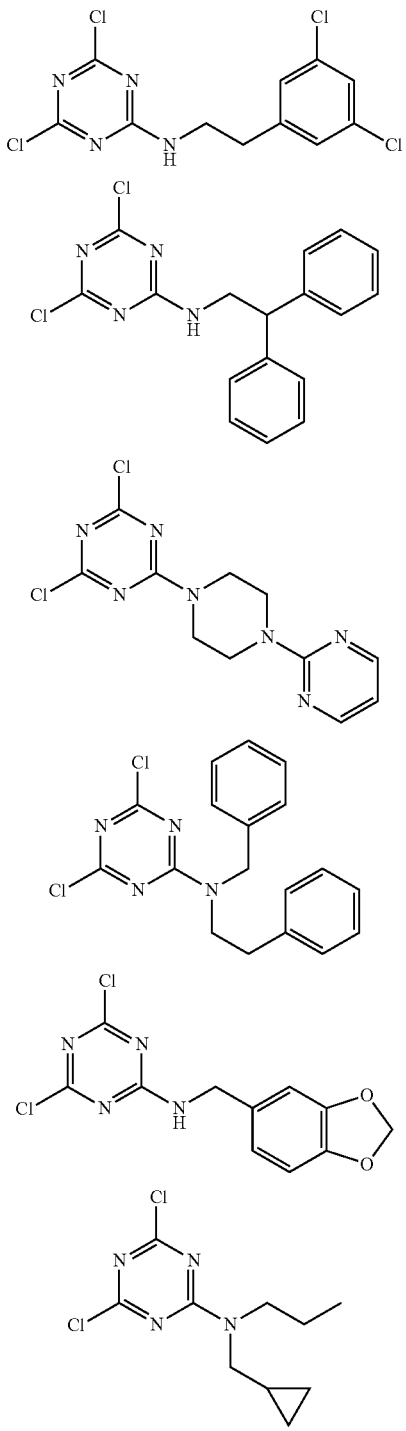

[Group 5]

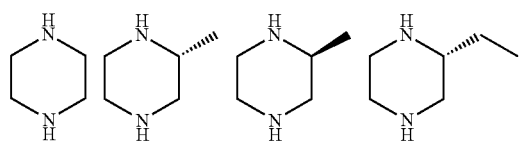

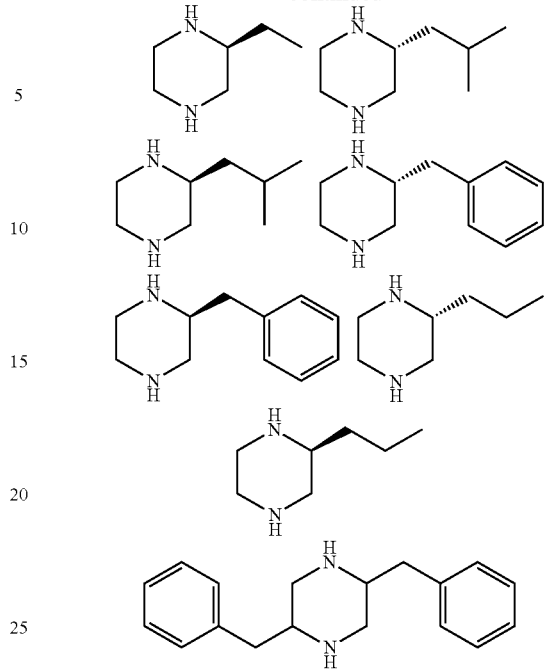

Figure 19:
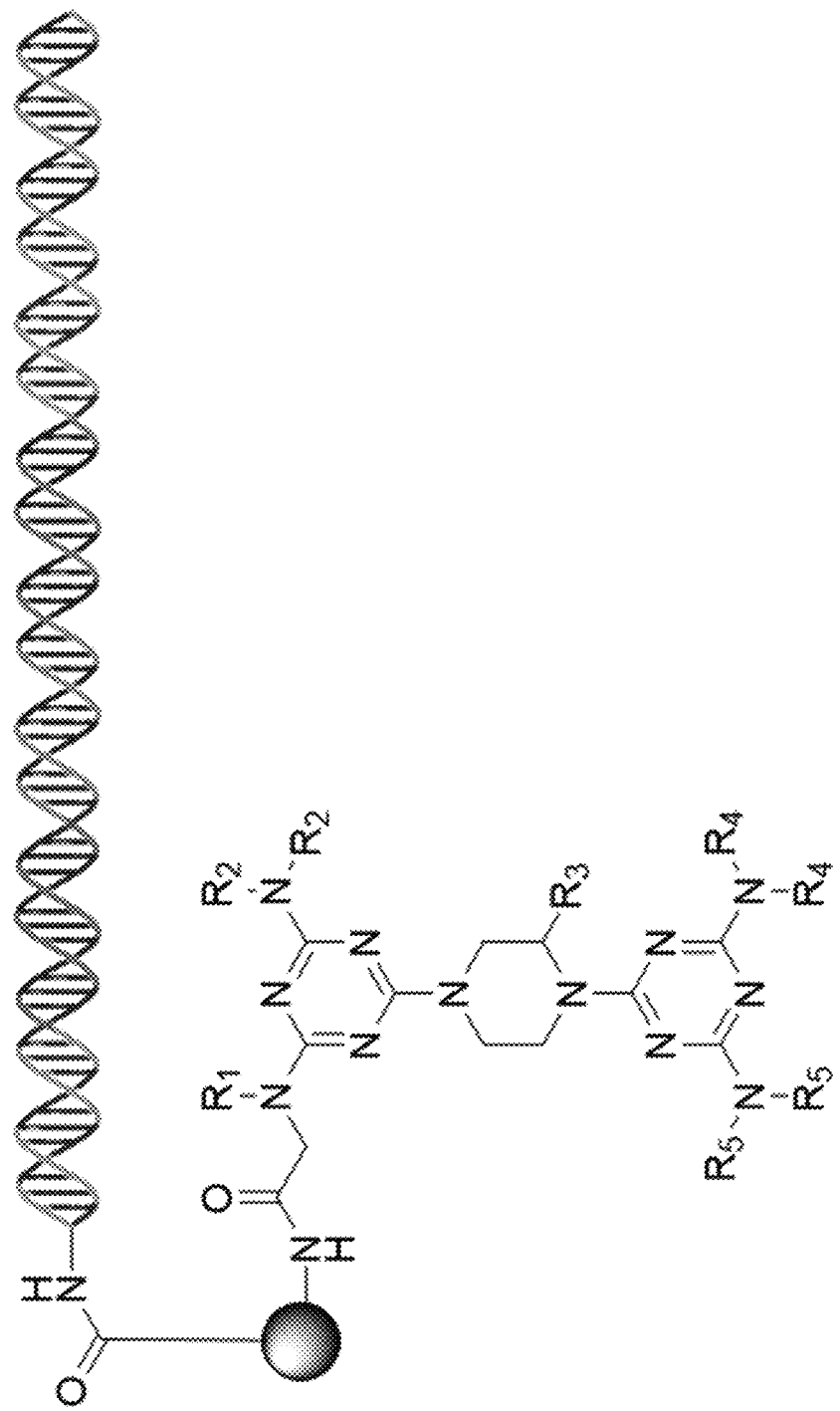
FIG. 19 schematically shows a structure of a nanostructure of an alpha-helix analogue library having a triazine-piperazine-triazine backbone according to Example 3.

FIG. 19 schematically shows a structure of a nanostructure of an alpha-helix analogue library having a triazine-piperazine-triazine backbone according to Example 3 and in FIG. 19, $R_n$ is a monovalent group derived from one of the first building blocks described in order, n of Table 3.

Figure 20:
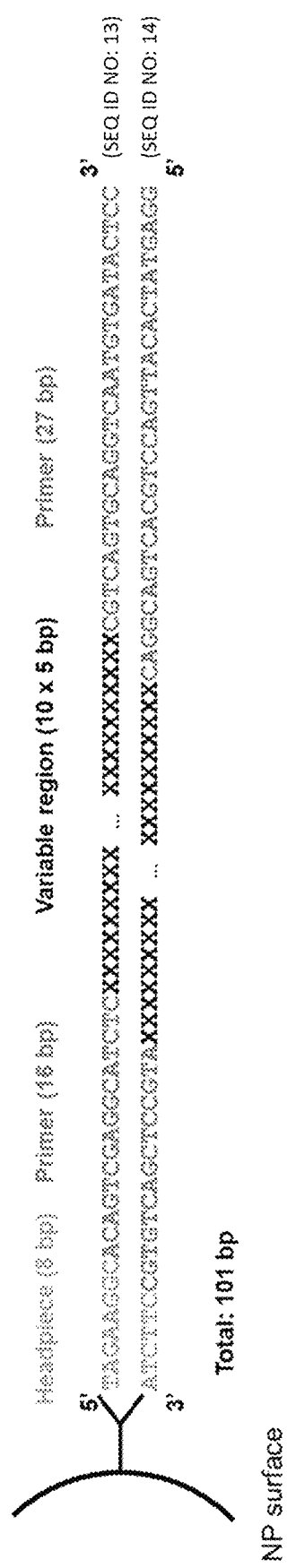
FIG. 20 schematically illustrates a second compound of nanostructures of an alpha-helix analogue library having a triazine-piperazine-triazine backbone according to Example 3.

FIG. 20 representatively shows a second compound including a DNA sequence encoding the probe.

Accordingly, the alpha-helix analogue library having a triazine-piperazine-triazine backbone according to Example 3 includes an alpha-helix analogue having 17×17×12×17×17=1,002,252 (about 1,000,000) triazine-piperazine-triazine backbones which are different one another.

Evaluation 4-1: Gel Electrophoresis of Alpha-Helix Analog Library Having Triazine-Piperazine-Triazine Backbone The DNA sequence encoding the probe of the nanostructures of the alpha-helix analogue library having a triazine-piperazine-triazine backbone according to Example 3 is amplified through a polymerase chain reaction and electrophoresed in an acrylamide gel, and the result is examined.

Specifically, the polymerase chain reaction is performed by mixing 1 μL of nanostructures, 0.4 μM forward primer (TAGAAGGCACAGTCGAGGCATCTC (SEQ ID NO: 159)), and 0.4 μM reverse primer (CAGGCAGTCACGTCCAGTTACACTATGAGG ((SEQ ID NO: 160)) which are dispersed in 0.05% Tween-20 (Georgiachem Co., Ltd.) aqueous solution at each concentration of 63, 6.3, and 0.63 ng/mL with 50 μL of premixed PCR solution (HelixAmp™ Ready-2x-Go, Nanohelix). The cycle of the polymerase chain reaction proceeded with [95° C. 10 s, 60° C. 10 s, 72° C. 10 s]×35, and 72° C. 5 min.

Specifically, the electrophoresis is performed on an 8% acrylamide gel, and development with size marker (Tech & Innovation, 50 bp ladder) on TBE (Tris-borate-EDTA) buffered saline at 130 V is performed.

Figure 21:
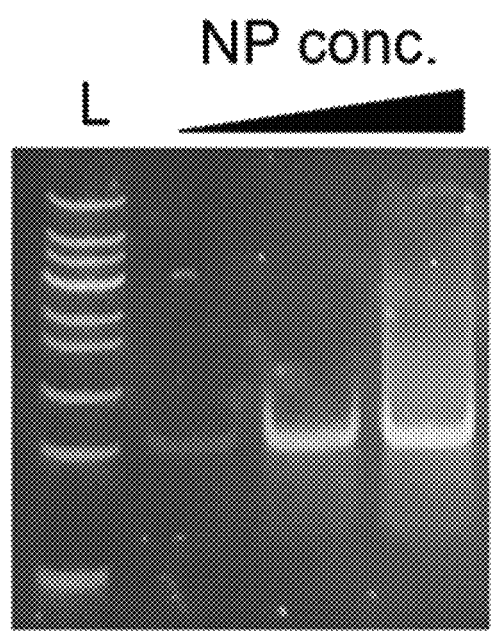
FIG. 21 shows results of amplification by PCR of DNA sequences encoding probes of the nanostructures of the alpha-helix analogue library having a triazine-piperazine-triazine backbone according to Example 3, and electrophoresis on an acrylamide gel.

FIG. 21 shows results of amplification by PCR of DNA sequences encoding probes of the nanostructures of the alpha-helix analogue library having a triazine-piperazine-triazine backbone according to Example 3, and electrophoresis thereof in an acrylamide gel.

Referring to FIG. 21, in the nanostructures of the alpha-helix analogue library having a triazine-piperazine-triazine backbone according to Example 3, the DNA sequence encoding the probe has a uniform size.

Evaluation 4-2: Dispersibility of Nanostructures of Alpha-Helix Analogue Library Having Triazine-Piperazine-Triazine Backbone The dispersibility of the nanostructures of the alpha-helix analogue library having the triazine-piperazine-triazine backbone is evaluated by using a photograph with a transmission electron microscope (TEM, JEOL JEM-2100 Electron Microscope), and a dynamic light scattering method is used to measure their sizes and the size distribution.

First, the nanostructures of the alpha-helix analogue library having a triazine-piperazine-triazine backbone according to Example 3 are dispersed in a methanol/water (1:1) solution, and the result is examined with TEM.

Figure 22:
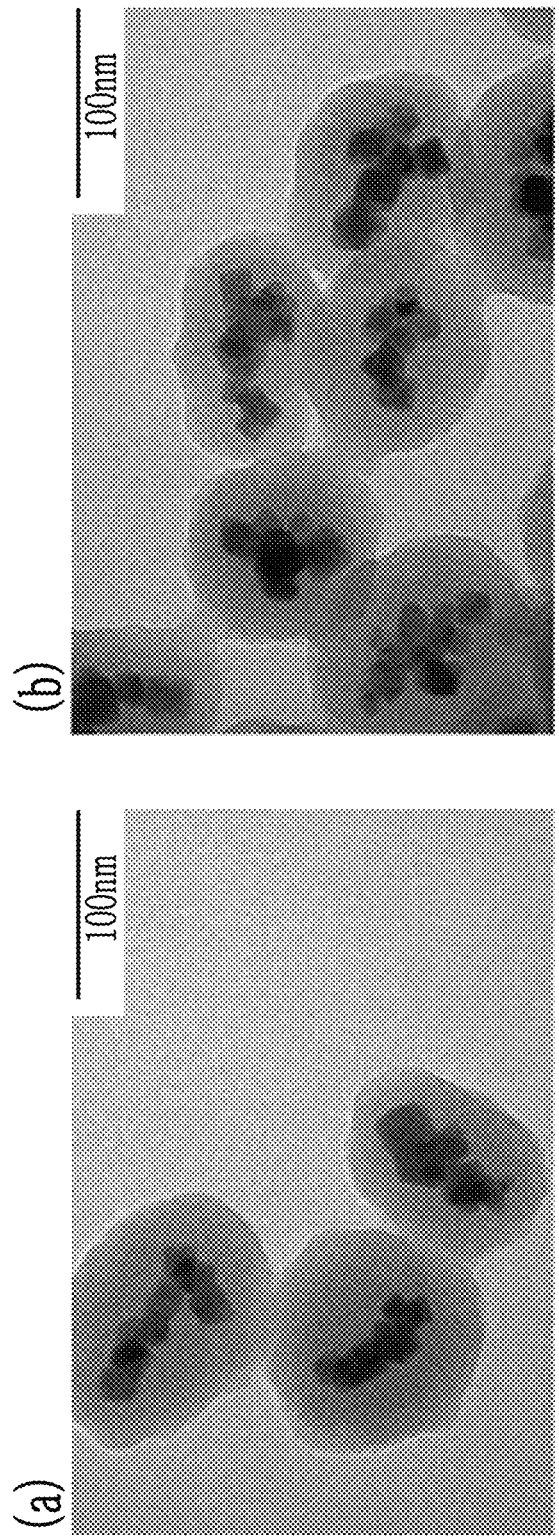
FIGS. 22 (a) and (b) are TEM photographs of nanostructures of the alpha-helix analogue library having a triazine-piperazine-triazine backbone according to Example 3 dispersed in a methanol/water (1:1) solution.

FIGS. 22 (a) and (b) are TEM photographs of nanostructures of the alpha-helix analogue library having a triazine-piperazine-triazine backbone according to Example 3 dispersed in methanol/water (1:1).

In addition, 0.11 mg of the nanostructure of the alpha-helix analogue library having the triazine-piperazine-triazine backbone according to Example 3 is added to 550 µL of a 0.05% Tween-20 aqueous solution (Georgiachem Co., Ltd.), and dimethylformamide (DMF) and dispersed therein, and sizes are measured the size using a dynamic light scattering meter (Malvern panalytical, Malvern zetasizer Z). Size distributions are shown in Table 8 and FIG. 23.

TABLE 8

| Solvent | 0.05% Tween-20 | DMF |
|---|---|---|
| DLS (nm) | 269.4 ± 7.1 | 220.4 ± 0.3 |

Figure 23:
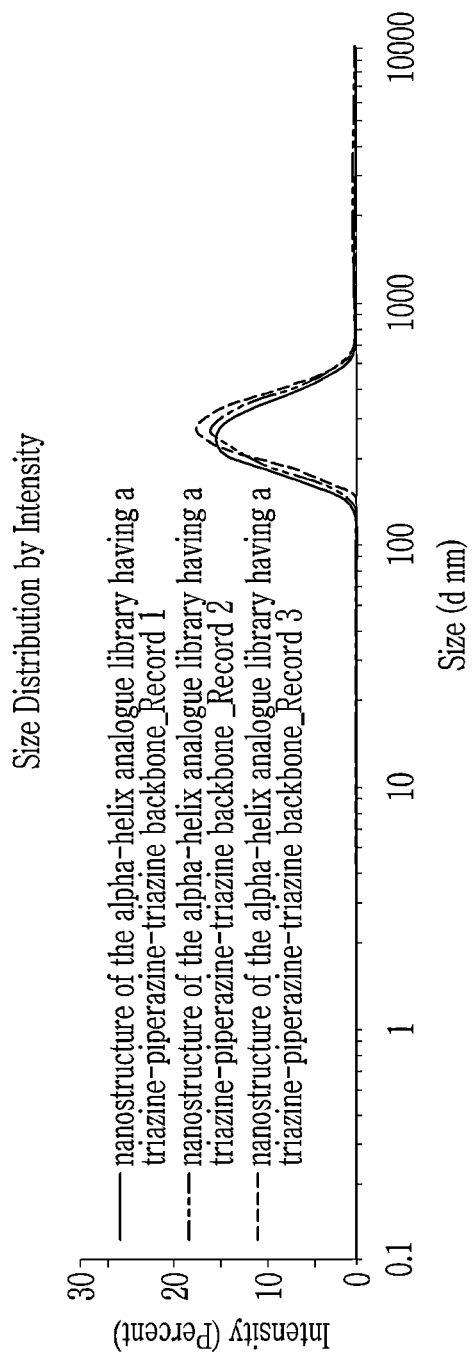
FIG. 23 is a graph showing size distributions in 0.05% Tween-20 solution, and dimethylformamide (DMF) of the nanostructures of the alpha-helix analogue library having a triazine-piperazine-triazine backbone according to Example 3, measured three times by a dynamic light scattering method, respectively.

FIG. 23 is a graph showing the size distributions of the nanostructures of the alpha-helix analogue library having a triazine-piperazine-triazine backbone according to Example 3 in the 0.05% Tween-20 solution, and dimethylformamide (DMF), measured three times by a dynamic light scattering method, respectively.

Referring to FIGS. 22 and 23 and Table 8, the nanostructures of the alpha-helix analogue library having a triazine-piperazine-triazine backbone according to Example 3 are not aggregated in methanol/water (1:1), the 0.05% Tween-20 solution, and the dimethyl formamide (DMF), and the size distributions are uniform.

In summary, the nanostructures of the alpha-helix analogue library having a triazine-piperazine-triazine backbone according to Example 3 have a DNA sequence encoding a uniformly-sized probe. In addition, the nanostructures of the alpha-helix analogue library having a triazine-piperazine-triazine backbone according to Example 3 have a uniform size and are not aggregated one another.

On the other hand, an alpha-helix analogue having a triazine-piperazine-triazine backbone is a low molecular weight material and may imitate a position of i, i+3(4), i+7 amino acid residual groups on the alpha-helix. Accordingly, this promising small molecule as well as peptide and/or peptoid may be applied to construct the library, and a new drug candidate may be found with high accuracy.

Affinity-Based Protein Screening

Evaluation 5-1: Screening of Liver Receptor Homolog 1 (LRH-1)

(1) The nanostructures of the stapled peptide library obtained in Example 1 are placed in a tube coated with streptavidin and incubated. Then, after removing nanostructures bonded with streptavidin and stuck to a tube wall and thus being falsely positive, nanostructures not stuck to the tube wall are used (a pre-screening step).

A screening buffer solution (TBS Start Block (Thermo Scientific), 0.05% Tween-20, 1 mg/mL sheared salmon sperm DNA (Invitrogen)) including 200 nM biotin-labeled LRH-1 is added to a half of the pre-screened nanostructures to prepare Mixed Solution 1 and is added to the other half of the biotin-labeled screening buffer solution without LRH-1 to prepare Mixed Solution 2, and then the two solutions are respectively incubated at 4° C. for 3 hours. Subsequently, Mixed Solutions 1 and 2 are respectively placed in two streptavidin-coated tubes (4 in total) and are incubated at 4° C. for 1 hour. In each tube, leaving the nanostructures attached to the tube walls, the remaining non-attached nanostructures are removed by washing 5 times with a screening buffer solution excluding sheared salmon sperm DNA.

In each tube containing Mixed Solutions 1 and 2, the nanostructures stuck to the tube wall are PCR-treated to amplify and purify the DNA sequence encoding the probe. Subsequently, DNA sequences encoding the probe synthesized from duplicate samples are analyzed through NGS analysis (Illumina platform).

Among the analyzed DNA sequences in the tube including Mixed Solution 1, 30 (60 in total) DNA sequences from the top in order of the largest number are selected except for the DNA sequences also analyzed in the tube including Mixed Solution 2. The sequence of a peptide (Hit-stapled peptide) which is bound to LRH-1 protein is decoded from the selected DNA sequence.

Figure 24A:
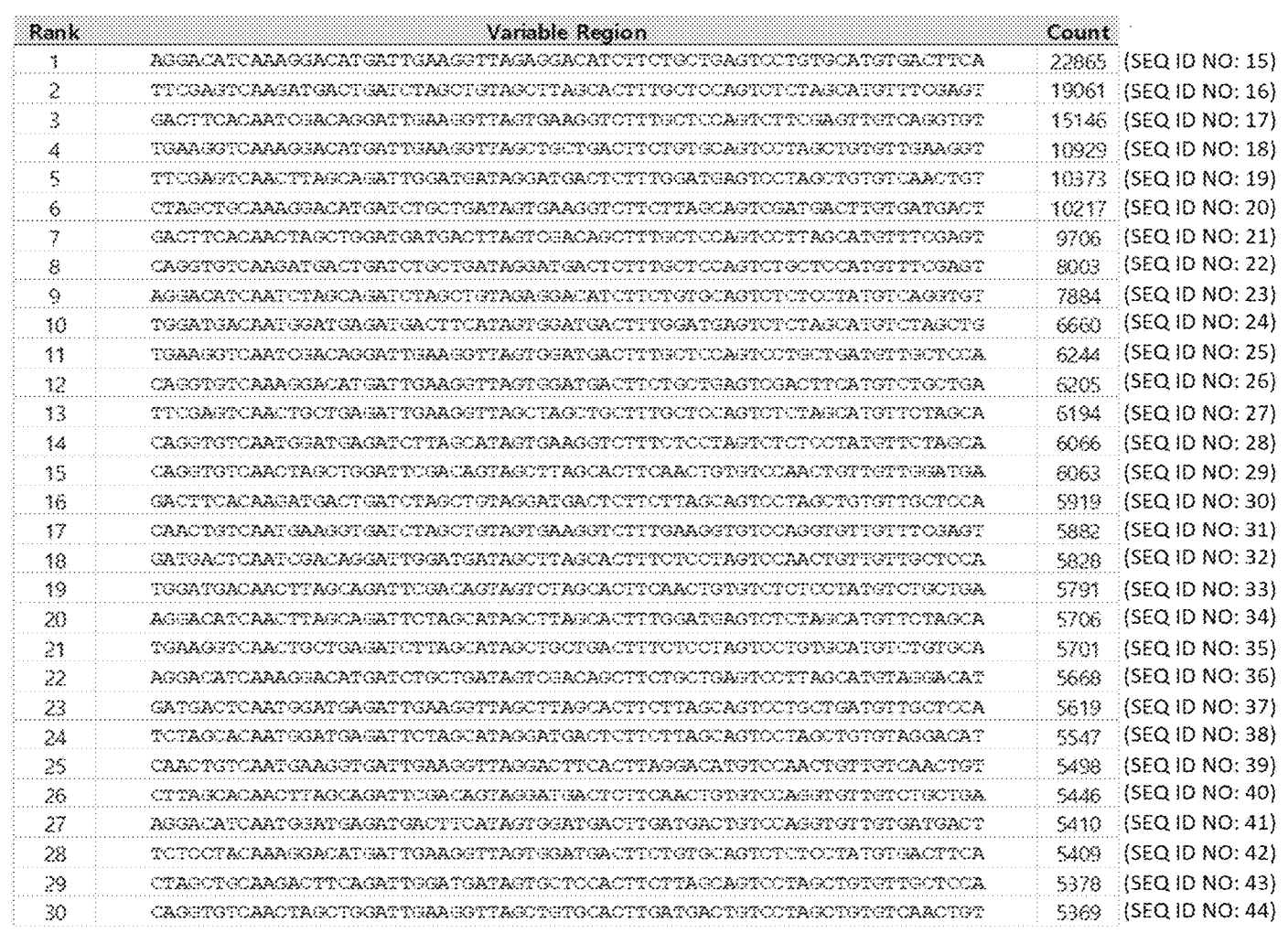
Figure 24B:
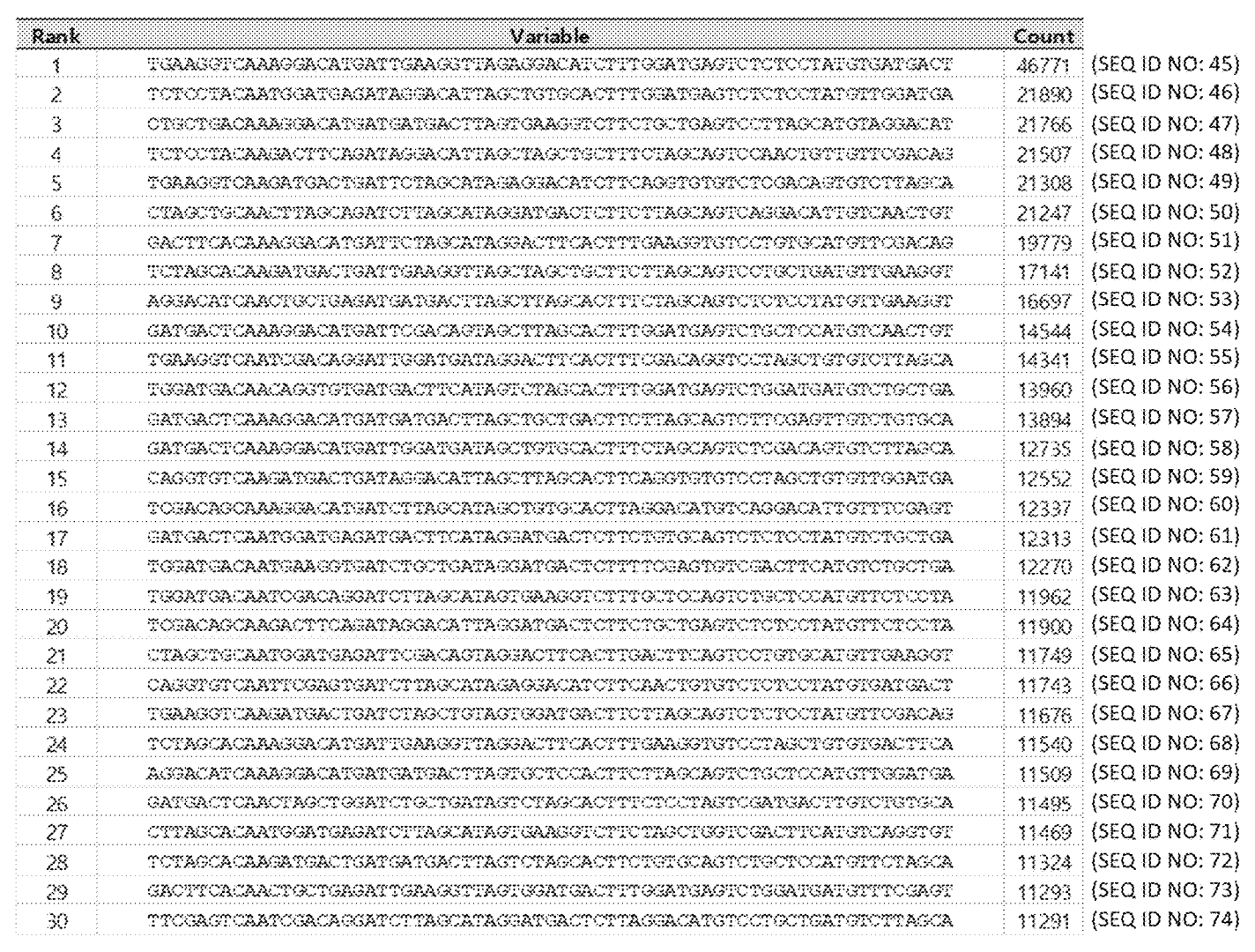

FIG. 24A and FIG. 24B illustrate the top 30 DNA sequences selected, and

FIG. 24C and FIG. 24D illustrate decoded sequences of the peptide (Hit-stapled peptide) bound to the LRH-1 protein from the selected DNA sequence.

(2) 8 sequences, including the largest number of sequences in FIG. 24C and FIG. 24D, are selected arbitrarily, and after synthesis of the stapled peptides of Hit 1 to 8 therefrom, respectively, a competitive fluorescence polarization assay (FP) is performed to examine whether or not the synthesized Hit 1 to 8 stapled peptides inhibit the interaction of LRH-1.

Specifically, the competitive fluorescence polarization assay is performed by binding 20 mM fluorescein-labeled DAX-1 box 3 peptide (FL-PRQGSILYSLLTSSK (SEQ ID NO: 161)) and 500 nM LRH-1-LBD (ligand binding domain) to a binding buffer (20 mM HEPES, pH 7.4, 150 mM NaCl, 0.01% Tween-20), and then stapled peptides of Hit 1 to 8 are incubated at various concentrations for 2 hours. Fluorescence polarization values are measured using a Tecan F200 Microplate Reader (Tecan) under excitation wavelength of 485 nm and emission wavelength of 535 nm.

Figure 25:
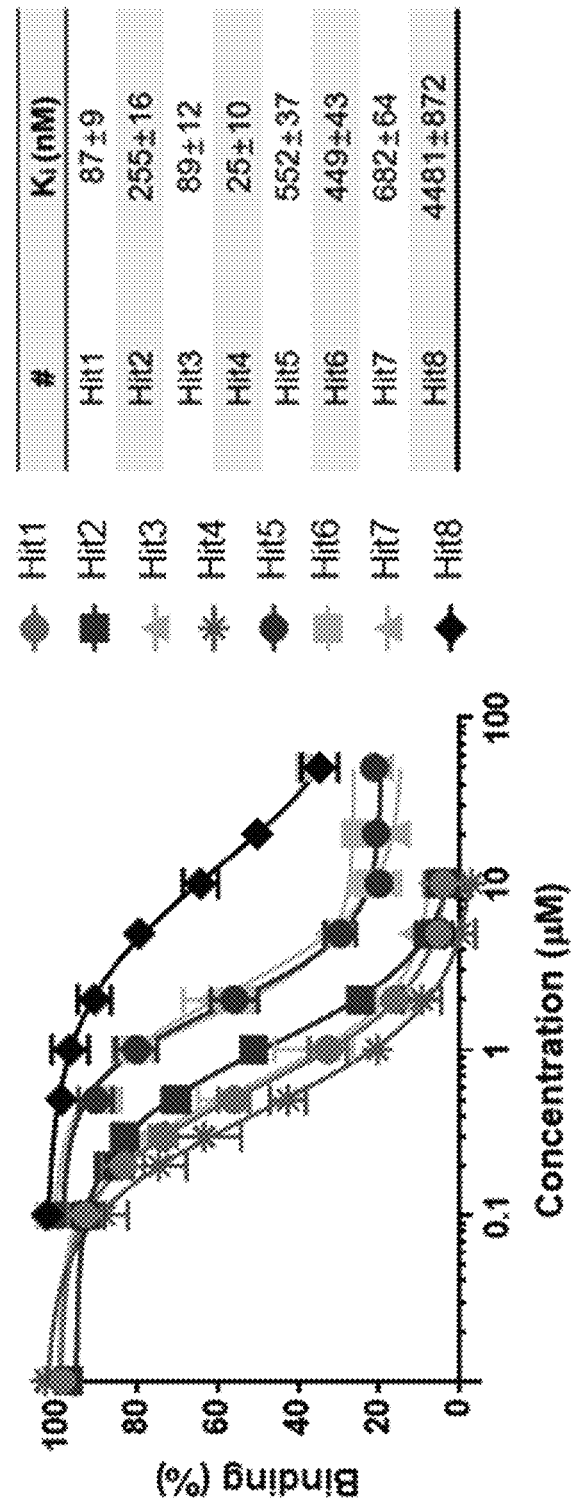
FIG. 25 is a graph showing changes in ratios of the binding of LRH-1 and stapled peptides depending on concentrations of the stapled peptide.

FIG. 25 is a graph showing changes in ratios of the binding of LRH-1 and stapled peptides depending on concentrations of the stapled peptides of Hit 1 to 8.

Referring to FIG. 25, the Hit 1 to 8 stapled peptides found through the stapled peptide library according to Example 1 have K of greater than or equal to 25 nM with respect to LRH-1 and a bonding force of an antibody level. Accordingly, the Hit 1 to 8 stapled peptides are bonded with LRH-1 and may work as an inhibitor of suppressing overexpression of LRH-1.

Evaluation 5-2: Screening of Protein Tyrosine Phosphatase 1B (PTP1B)

PTP1B is screened to select the top 10 (20 in total) DNA sequences in order of the largest number according to the same method as Evaluation 5-1 except that the nanostructures of the peptoid library according to Example 2 instead of the nanostructures of the stapled peptide library according to Example 1 PTP1B instead of LRH-1 are used.

FIG. 26 illustrates the top 10 selected DNA sequences.

Since PTP1B is a type of PTP family and one protein known to be closely related to second type diabetes and obesity, the peptoid library according to Example 2 is used to decode the DNA sequence by screening PTP1B and thus identify peptoid bonded with PTP1B, which may be used as a new drug candidate.

Evaluation 5-3: Screening of B-Cell Lymphoma-Extra Large (Bcl-xL)a Protein

Bcl-xL is screened to select the top 10 DNA sequences in order of the largest number in the same method as in Evaluation 5-1, except that the nanostructures of the alpha-helix analog library having the triazine-piperazine-triazine backbone obtained in Example 3 are used instead of the nanostructures of the stapled peptide library obtained in Example 1 and Bcl-xL is used instead of LRH-1.

FIG. 27A illustrates the top 10 selected DNA sequences, and

Figure 27B:
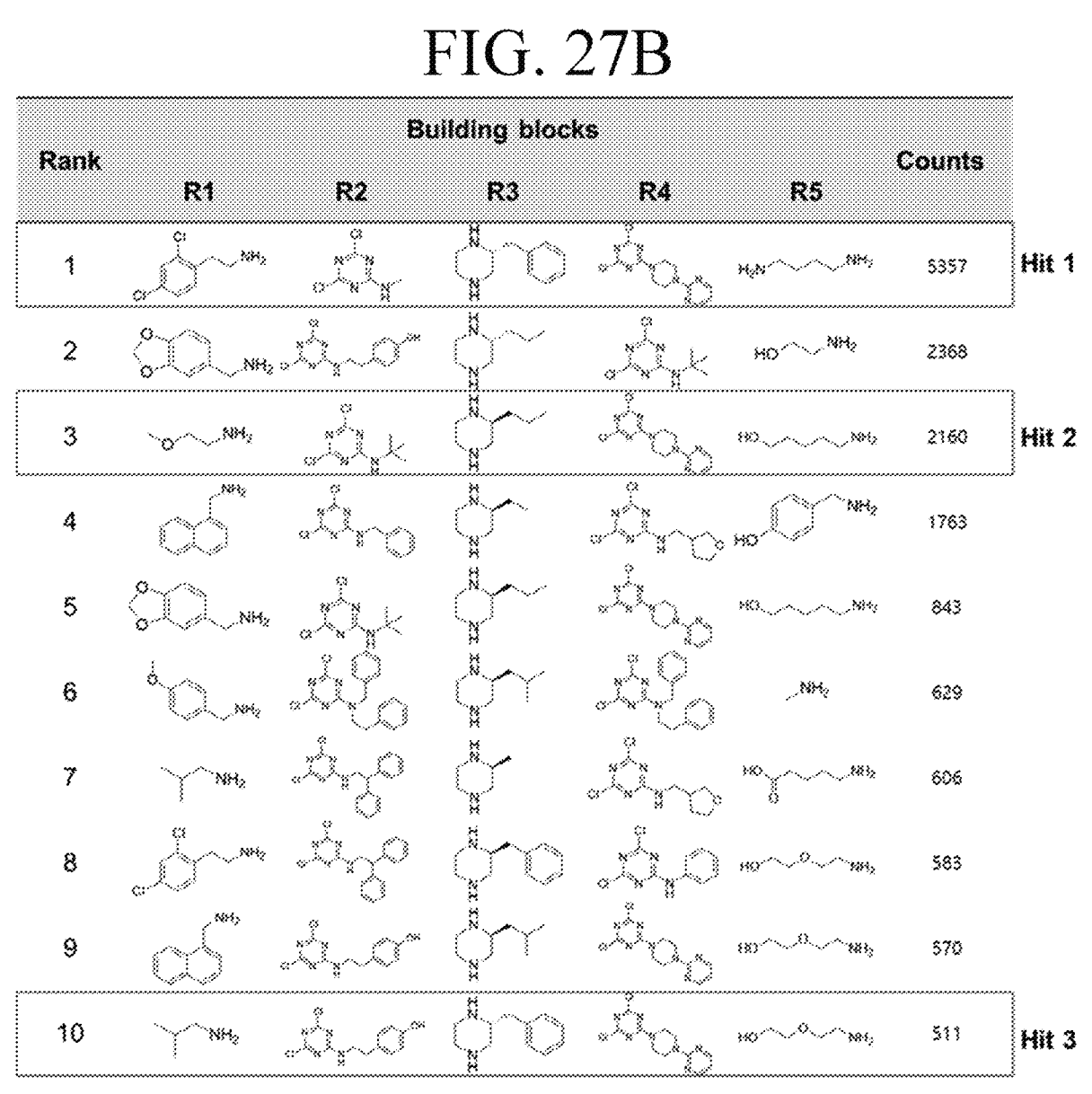

FIG. 27B illustrates decoded sequences of an alpha-helix analogue having a triazine-piperazine-triazine backbone (Hit-triazine-piperazine-triazine backbone) that is bound to the Bcl-xL protein, from the selected DNA sequences.

3 sequences, including the largest number of sequences in FIG. 27B are selected arbitrarily, from these, alpha-helix analogues each having a triazine-piperazine-triazine backbone of Hit 1 to 3 are synthesized in a fluorescently labeled form, and a fluorescence polarization assay (FP) is performed to examine whether or not the small molecules of the synthesized Hit 1 to 3 are bound to Bcl-xL.

Specifically, alpha-helix analogues having a triazine-piperazine-triazine backbone of Hit 1 to 3 labeled with 100 nM of fluorescein are respectively added to binding buffers (50 mM Tris-CI, pH 8.0, 150 mM NaCl, 0.01% Tween-20), then various concentrations of Bcl-xL protein are added, and the resultant is incubated for 1 hour. Fluorescence polarization values are measured using a Tecan F200 Microplate Reader (Tecan) under excitation wavelength of 485 nm and emission wavelength of 535 nm.

Figure 28:
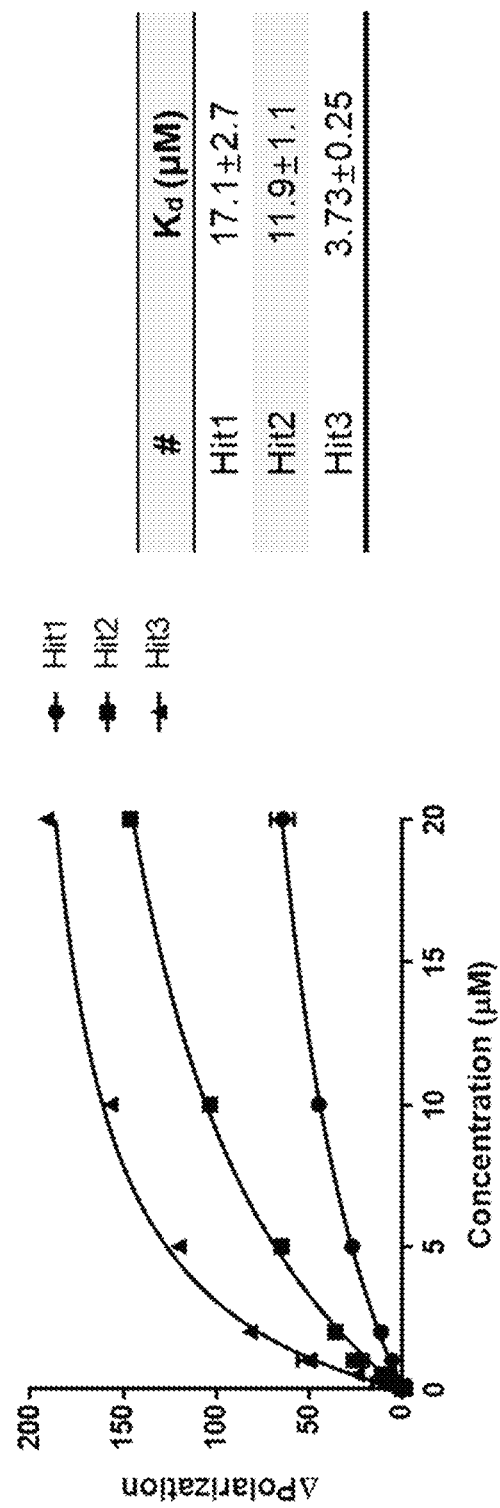
FIG. 28 is a graph showing changes in fluorescence polarization values of fluorescein labeled in an alpha-helix analogue having a triazine-piperazine-triazine backbone of Hit 1 to 3 depending on concentrations of Bcl-xL.

FIG. 28 is a graph showing changes in fluorescence polarization values of fluorescein labeled in an alpha-helix analogue having a triazine-piperazine-triazine backbone of Hit 1 to 3 depending on concentrations of Bcl-xL.

Bcl-xL is a protein that inhibits apoptosis and is one of proteins known to be overexpressed in various cancer cells. The DNA sequences obtained by screening Bcl-xL using an alpha-helix analogue library having a triazine-piperazine-triazine backbone according to Example 3 xL are encoded to find a small molecule which binds to Bcl-xL and may be used as a new drug candidate.

While this invention has been described in connection with what is presently considered to be practical example embodiments, it is to be understood that the invention is not limited to the disclosed embodiments. On the contrary, it is intended to cover various modifications and equivalent arrangements included within the spirit and scope of the appended claims.

What is claimed is:

1. A nanostructure comprising
a nanoparticle,
a first compound comprising a probe and bound to the surface of the nanoparticle,
a second compound comprising a DNA sequence encoding the probe and bound to the surface of the nanoparticle, and
optionally, a substituted or unsubstituted polyalkylene glycol bound to the surface of the nanoparticle,
wherein, when the nanostructure does not comprise the substituted or unsubstituted polyalkylene glycol, a ratio $((n^1+n^2)/w)$ of the sum of the number of moles $(n^1)$ of the first compound and the number of moles $(n^2)$ of the second compound relative to the weight (w) of the nanostructure is about 1.2 nmol/g to about 85 μmol/g on average, and
wherein the nanoparticle has a core-shell structure,
the core comprises substituted or unsubstituted polystyrene optionally comprising ferrite, substituted or unsubstituted polyglycidyl methacrylate optionally comprising ferrite, a substituted or unsubstituted polystyrene-polyglycidol methacrylate copolymer optionally comprising ferrite, or a combination thereof, and
the shell is a substituted or unsubstituted polyglycidylmethacrylate.

2. The nanostructure of claim 1, wherein the nanoparticle has a size of about 10 nm to about 1,000 nm.

3. The nanostructure of claim 1, wherein the second compound has at least two ends, wherein one end of which is bound to the nanoparticle, and the other end of which is a sticky end.

4. The nanostructure of claim 1, wherein the probe comprises a peptide, a peptide mimetic, a small molecule, or a combination thereof.

5. The nanostructure of claim 1, wherein the probe comprises a D-peptide, an L-peptide, a cyclic peptide, a stapled peptide, a peptoid, a cyclic peptoid, a foldamer, a small molecule comprising a triazine moiety, a small molecule comprising a pyrrolopyrimidine moiety, a small molecule comprising a benzimidazole moiety, or a combination thereof.

6. The nanostructure of claim 1, wherein the second compound comprises a primer at both ends of the DNA sequence encoding the probe.

7. The nanostructure of claim 1, wherein the nanostructure comprises the substituted or unsubstituted polyalkylene glycol bound to the surface of the nanoparticle, and wherein a weight average molecular weight of the substituted or unsubstituted polyalkylene glycol is about 1,000 Da to about 10,000 Da.

8. The nanostructure of claim 1, wherein the nanostructure comprises the substituted or unsubstituted polyalkylene glycol bound to the surface of the nanoparticle, and wherein the substituted or unsubstituted polyalkylene glycol is a substituted or unsubstituted polyethylene glycol.

9. The nanostructure of claim 1, wherein a ratio ($n^1$:$n^2$) of the number of moles ($n^1$) of the first compound and the number of moles ($n^2$) of the second compound is about 1.5:1 to about 1,000:1.

10. The nanostructure of claim 1, wherein
the nanostructure comprises the substituted or unsubstituted polyalkylene glycol, and
wherein a ratio ($n^3$/w) of the number of moles ($n^3$) of the substituted or unsubstituted polyalkylene glycol relative to the weight (w) of the nanostructure is greater than or equal to 100 μmol/g on average.

11. The nanostructure of claim 1, wherein
the nanostructure does not comprise the substituted or unsubstituted polyalkylene glycol, and
wherein a ratio ($n^1$/w) of the number of moles ($n^1$) of the first compound relative to the weight (w) of the nanostructure is less than or equal to about 60 μmol/g.

12. A biosensor comprising the nanostructure of claim 1.

* * * * *

SEQUENCE LISTING

```
<160> NUMBER OF SEQ ID NOS: 160

<210> SEQ ID NO 1
<211> LENGTH: 74
<212> TYPE: DNA
<213> ORGANISM: Artificial Sequence
<220> FEATURE:
<223> OTHER INFORMATION: a second compound including a DNA sequence
      encoding a probe

<400> SEQUENCE: 1
tctcctgctg gcaactgctg agatctgctg atagtgaagg tcttctagct ggtcctgctg      60
atgtctgtgc aacc                                                        74

<210> SEQ ID NO 2
<211> LENGTH: 74
<212> TYPE: DNA
<213> ORGANISM: Artificial Sequence
<220> FEATURE:
<223> OTHER INFORMATION: a second compound including a DNA sequence
      encoding a probe

<400> SEQUENCE: 2
tctctggatg acaatgctcc agatgatgac ttagcaactg tcttctgctg agtcctgtgc      60
atgtctgtgc aacc                                                        74

<210> SEQ ID NO 3
<211> LENGTH: 74
<212> TYPE: DNA
<213> ORGANISM: Artificial Sequence
<220> FEATURE:
```

```
<223> OTHER INFORMATION: a second compound including a DNA sequence
      encoding a probe

<400> SEQUENCE: 3
tctctcgaca gcaatggatg agatttcgag ttagctgctg acttaggaca tgtctctagc    60
atgtgatgac tacc                                                     74

<210> SEQ ID NO 4
<211> LENGTH: 74
<212> TYPE: DNA
<213> ORGANISM: Artificial Sequence
<220> FEATURE:
<223> OTHER INFORMATION: a second compound including a DNA sequence
      encoding a probe

<400> SEQUENCE: 4
tctcctagct gcaaaggaca tgattctagc atagctagct gcttcaactg tgtcgacttc    60
atgtctgtgc aacc                                                     74

<210> SEQ ID NO 5
<211> LENGTH: 74
<212> TYPE: DNA
<213> ORGANISM: Artificial Sequence
<220> FEATURE:
<223> OTHER INFORMATION: a second compound including a DNA sequence
      encoding a probe

<400> SEQUENCE: 5
tctcctgctg acaactgctg agattctcct atagctgctg actttgaagg tgtcttcgag    60
ttgtcaggtg tacc                                                     74

<210> SEQ ID NO 6
<211> LENGTH: 74
<212> TYPE: DNA
<213> ORGANISM: Artificial Sequence
<220> FEATURE:
<223> OTHER INFORMATION: a second compound including a DNA sequence
      encoding a probe

<400> SEQUENCE: 6
tctctctcct acaattcgag tgatcttagc atagtgaagg tcttctagct ggtccaactg    60
ttgttctagc aacc                                                     74

<210> SEQ ID NO 7
<211> LENGTH: 74
<212> TYPE: DNA
<213> ORGANISM: Artificial Sequence
<220> FEATURE:
<223> OTHER INFORMATION: a second compound including a DNA sequence
      encoding a probe

<400> SEQUENCE: 7
tctccttagc acaattcgag tgataggaca ttagctgtgc actttgctcc agtccaactg    60
ttgtcttagc aacc                                                     74

<210> SEQ ID NO 8
<211> LENGTH: 74
<212> TYPE: DNA
<213> ORGANISM: Artificial Sequence
<220> FEATURE:
<223> OTHER INFORMATION: a second compound including a DNA sequence
      encoding a probe

<400> SEQUENCE: 8
```
tctctggatg acaatcgaca ggattctagc atagctagct gctttgaagg tgtctgaagg    60
ttgtctgtgc aacc    74

<210> SEQ ID NO 9
<211> LENGTH: 74
<212> TYPE: DNA
<213> ORGANISM: Artificial Sequence
<220> FEATURE:
<223> OTHER INFORMATION: a second compound including a DNA sequence
      encoding a probe

<400> SEQUENCE: 9
tctcaggaca tcaactagct ggatctgctg atagaggaca tcttctgtgc agtcgatgac    60
ttgtctgctg aacc    74

<210> SEQ ID NO 10
<211> LENGTH: 74
<212> TYPE: DNA
<213> ORGANISM: Artificial Sequence
<220> FEATURE:
<223> OTHER INFORMATION: a second compound including a DNA sequence
      encoding a probe

<400> SEQUENCE: 10
tctctgaagg tcaactgtgc agattgaagg ttagtggatg acttgatgac tgtcgatgac    60
ttgtctgtgc aacc    74

<210> SEQ ID NO 11
<211> LENGTH: 121
<212> TYPE: DNA
<213> ORGANISM: Artificial Sequence
<220> FEATURE:
<223> OTHER INFORMATION: a second compound including a DNA sequence
      encoding a probe
<220> FEATURE:
<221> NAME/KEY: STS
<222> LOCATION: (25)..(94)
<223> OTHER INFORMATION: n are independently a, c, g, or t

<400> SEQUENCE: 11
tagaaggcac agtcgaggca tctcnnnnnn nnnnnnnnnn nnnnnnnnnn nnnnnnnnnn    60
nnnnnnnnnn nnnnnnnnnn nnnnnnnnnn nnnnactgat caggagacag ctatgctgac   120
c    121

<210> SEQ ID NO 12
<211> LENGTH: 121
<212> TYPE: DNA
<213> ORGANISM: Artificial Sequence
<220> FEATURE:
<223> OTHER INFORMATION: a second compound including a DNA sequence
      encoding a probe
<220> FEATURE:
<221> NAME/KEY: STS
<222> LOCATION: (31)..(100)
<223> OTHER INFORMATION: n are independently a, c, g, or t

<400> SEQUENCE: 12
ggtcagcata gctgtctcct gatcagtggt nnnnnnnnnn nnnnnnnnnn nnnnnnnnnn    60
nnnnnnnnnn nnnnnnnnnn nnnnnnnnnn nnnnnnnnnn atgcctcgac tgtgccttct   120
a    121

<210> SEQ ID NO 13

```
<211> LENGTH: 101
<212> TYPE: DNA
<213> ORGANISM: Artificial Sequence
<220> FEATURE:
<223> OTHER INFORMATION: a second compound including a DNA sequence
      encoding a probe
<220> FEATURE:
<221> NAME/KEY: STS
<222> LOCATION: (25)..(74)
<223> OTHER INFORMATION: n are independently a, c, g, or t

<400> SEQUENCE: 13
tagaaggcac agtcgaggca tctcnnnnnn nnnnnnnnnn nnnnnnnnnn nnnnnnnnnn    60
nnnnnnnnnn nnnncgtcag tgcaggtcaa tgtgatactc c                       101

<210> SEQ ID NO 14
<211> LENGTH: 101
<212> TYPE: DNA
<213> ORGANISM: Artificial Sequence
<220> FEATURE:
<223> OTHER INFORMATION: a second compound including a DNA sequence
      encoding a probe
<220> FEATURE:
<221> NAME/KEY: STS
<222> LOCATION: (31)..(80)
<223> OTHER INFORMATION: n are independently a, c, g, or t

<400> SEQUENCE: 14
ggagtatcac attgacctgc actgacggac nnnnnnnnnn nnnnnnnnnn nnnnnnnnnn    60
nnnnnnnnnn nnnnnnnnnn atgcctcgac tgtgccttct a                       101

<210> SEQ ID NO 15
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 15
aggacatcaa aggacatgat tgaaggttag aggacatctt ctgctgagtc ctgtgcatgt    60
gacttca                                                             67

<210> SEQ ID NO 16
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 16
ttcgagtcaa gatgactgat ctagctgtag cttagcactt tgctccagtc tctagcatgt    60
ttcgagt                                                             67

<210> SEQ ID NO 17
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 17
gacttcacaa tcgacaggat tgaaggttag tgaaggtctt tgctccagtc ttcgagttgt    60
``` caggtgt                                                             67

<210> SEQ ID NO 18
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 18
tgaaggtcaa aggacatgat tgaaggttag ctgctgactt ctgtgcagtc ctagctgtgt    60
tgaaggt                                                             67

<210> SEQ ID NO 19
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 19
ttcgagtcaa cttagcagat tggatgatag gatgactctt tggatgagtc ctagctgtgt    60
caactgt                                                             67

<210> SEQ ID NO 20
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 20
ctagctgcaa aggacatgat ctgctgatag tgaaggtctt cttagcagtc gatgacttgt    60
gatgact                                                             67

<210> SEQ ID NO 21
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 21
gacttcacaa ctagctggat gatgacttag tcgacagctt tgctccagtc cttagcatgt    60
ttcgagt                                                             67

<210> SEQ ID NO 22
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 22
caggtgtcaa gatgactgat ctgctgatag gatgactctt tgctccagtc tgctccatgt    60
ttcgagt                                                             67

<210> SEQ ID NO 23

```
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 23
aggacatcaa tctagcagat ctagctgtag aggacatctt ctgtgcagtc tctcctatgt     60
caggtgt                                                              67

<210> SEQ ID NO 24
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 24
tggatgacaa tggatgagat gacttcatag tggatgactt tggatgagtc tctagcatgt     60
ctagctg                                                              67

<210> SEQ ID NO 25
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 25
tgaaggtcaa tcgacaggat tgaaggttag tggatgactt tgctccagtc ctgctgatgt     60
tgctcca                                                              67

<210> SEQ ID NO 26
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 26
caggtgtcaa aggacatgat tgaaggttag tggatgactt ctgctgagtc gacttcatgt     60
ctgctga                                                              67

<210> SEQ ID NO 27
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 27
ttcgagtcaa ctgctgagat tgaaggttag ctagctgctt tgctccagtc tctagcatgt     60
tctagca                                                              67

<210> SEQ ID NO 28
<211> LENGTH: 67
<212> TYPE: DNA
<213> ORGANISM: Artificial Sequence
<220> FEATURE:
```

```
<223> OTHER INFORMATION: DNA sequences selected by screening LRH-1 in
      the stapled peptide library according to Example 1

<400> SEQUENCE: 28
caggtgtcaa tggatgagat cttagcatag tgaaggtctt tctcctagtc tctcctatgt    60
tctagca                                                              67

<210> SEQ ID NO 29
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 29
caggtgtcaa ctagctggat tcgacagtag cttagcactt caactgtgtc caactgttgt    60
tggatga                                                              67

<210> SEQ ID NO 30
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 30
gacttcacaa gatgactgat ctagctgtag gatgactctt cttagcagtc ctagctgtgt    60
tgctcca                                                              67

<210> SEQ ID NO 31
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 31
caactgtcaa tgaaggtgat ctagctgtag tgaaggtctt tgaaggtgtc caggtgttgt    60
ttcgagt                                                              67

<210> SEQ ID NO 32
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 32
gatgactcaa tcgacaggat tggatgatag cttagcactt tctcctagtc caactgttgt    60
tgctcca                                                              67

<210> SEQ ID NO 33
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 33
```
tggatgacaa cttagcagat tcgacagtag tctagcactt caactgtgtc tctcctatgt    60
ctgctga                                                              67

<210> SEQ ID NO 34
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 34
aggacatcaa cttagcagat tctagcatag cttagcactt tggatgagtc tctagcatgt    60
tctagca                                                              67

<210> SEQ ID NO 35
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 35
tgaaggtcaa ctgctgagat cttagcatag ctgctgactt tctcctagtc ctgtgcatgt    60
ctgtgca                                                              67

<210> SEQ ID NO 36
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 36
aggacatcaa aggacatgat ctgctgatag tcgacagctt ctgctgagtc cttagcatgt    60
aggacat                                                              67

<210> SEQ ID NO 37
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 37
gatgactcaa tggatgagat tgaaggttag cttagcactt cttagcagtc ctgctgatgt    60
tgctcca                                                              67

<210> SEQ ID NO 38
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 38
tctagcacaa tggatgagat tctagcatag gatgactctt cttagcagtc ctagctgtgt    60
aggacat                                                              67

<210> SEQ ID NO 39
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 39
caactgtcaa tgaaggtgat tgaaggttag gacttcactt aggacatgtc caactgttgt    60
caactgt                                                              67

<210> SEQ ID NO 40
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 40
cttagcacaa cttagcagat tcgacagtag gatgactctt caactgtgtc caggtgttgt    60
ctgctga                                                              67

<210> SEQ ID NO 41
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 41
aggacatcaa tggatgagat gacttcatag tggatgactt gatgactgtc caggtgttgt    60
gatgact                                                              67

<210> SEQ ID NO 42
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 42
tctcctacaa aggacatgat tgaaggttag tggatgactt ctgtgcagtc tctcctatgt    60
gacttca                                                              67

<210> SEQ ID NO 43
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 43
ctagctgcaa gacttcagat tggatgatag tgctccactt cttagcagtc ctagctgtgt    60
tgctcca                                                              67

<210> SEQ ID NO 44
<211> LENGTH: 67

```
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 44
caggtgtcaa ctagctggat tgaaggttag ctgtgcactt gatgactgtc ctagctgtgt     60
caactgt                                                                67

<210> SEQ ID NO 45
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 45
tgaaggtcaa aggacatgat tgaaggttag aggacatctt tggatgagtc tctcctatgt     60
gatgact                                                                67

<210> SEQ ID NO 46
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 46
tctcctacaa tggatgagat aggacattag ctgtgcactt tggatgagtc tctcctatgt     60
tggatga                                                                67

<210> SEQ ID NO 47
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 47
ctgctgacaa aggacatgat gatgacttag tgaaggtctt ctgctgagtc cttagcatgt     60
aggacat                                                                67

<210> SEQ ID NO 48
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 48
tctcctacaa gacttcagat aggacattag ctagctgctt tctagcagtc caactgttgt     60
tcgacag                                                                67

<210> SEQ ID NO 49
<211> LENGTH: 67
<212> TYPE: DNA
<213> ORGANISM: Artificial Sequence
<220> FEATURE:
<223> OTHER INFORMATION: DNA sequences selected by screening LRH-1 in
``` the stapled peptide library according to Example 1

<400> SEQUENCE: 49
tgaaggtcaa gatgactgat tctagcatag aggacatctt caggtgtgtc tcgacagtgt    60
cttagca                                                              67

<210> SEQ ID NO 50
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 50
ctagctgcaa cttagcagat cttagcatag gatgactctt cttagcagtc aggacattgt    60
caactgt                                                              67

<210> SEQ ID NO 51
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 51
gacttcacaa aggacatgat tctagcatag gacttcactt tgaaggtgtc ctgtgcatgt    60
tcgacag                                                              67

<210> SEQ ID NO 52
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 52
tctagcacaa gatgactgat tgaaggttag ctagctgctt cttagcagtc ctgctgatgt    60
tgaaggt                                                              67

<210> SEQ ID NO 53
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 53
aggacatcaa ctgctgagat gatgacttag cttagcactt tctagcagtc tctcctatgt    60
tgaaggt                                                              67

<210> SEQ ID NO 54
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 54

```
gatgactcaa aggacatgat tcgacagtag cttagcactt tggatgagtc tgctccatgt    60
caactgt                                                               67
```

<210> SEQ ID NO 55
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 55

```
tgaaggtcaa tcgacaggat tggatgatag gacttcactt tcgacaggtc ctagctgtgt    60
cttagca                                                               67
```

<210> SEQ ID NO 56
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 56

```
tggatgacaa caggtgtgat gacttcatag tctagcactt tggatgagtc tggatgatgt    60
ctgctga                                                               67
```

<210> SEQ ID NO 57
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 57

```
gatgactcaa aggacatgat gatgacttag ctgctgactt cttagcagtc ttcgagttgt    60
ctgtgca                                                               67
```

<210> SEQ ID NO 58
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 58

```
gatgactcaa aggacatgat tggatgatag ctgtgcactt tctagcagtc tcgacagtgt    60
cttagca                                                               67
```

<210> SEQ ID NO 59
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 59

```
caggtgtcaa gatgactgat aggacattag cttagcactt caggtgtgtc ctagctgtgt    60
tggatga                                                               67
```

<210> SEQ ID NO 60
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 60
tcgacagcaa aggacatgat cttagcatag ctgtgcactt aggacatgtc aggacattgt    60
ttcgagt                                                              67

<210> SEQ ID NO 61
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 61
gatgactcaa tggatgagat gacttcatag gatgactctt ctgtgcagtc tctcctatgt    60
ctgctga                                                              67

<210> SEQ ID NO 62
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 62
tggatgacaa tgaaggtgat ctgctgatag gatgactctt ttcgagtgtc gacttcatgt    60
ctgctga                                                              67

<210> SEQ ID NO 63
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 63
tggatgacaa tcgacaggat cttagcatag tgaaggtctt tgctccagtc tgctccatgt    60
tctccta                                                              67

<210> SEQ ID NO 64
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 64
tcgacagcaa gacttcagat aggacattag gatgactctt ctgctgagtc tctcctatgt    60
tctccta                                                              67

<210> SEQ ID NO 65
<211> LENGTH: 67
<212> TYPE: DNA

<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 65
ctagctgcaa tggatgagat tcgacagtag gacttcactt gacttcagtc ctgtgcatgt    60
tgaaggt                                                              67

<210> SEQ ID NO 66
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 66
caggtgtcaa ttcgagtgat cttagcatag aggacatctt caactgtgtc tctcctatgt    60
gatgact                                                              67

<210> SEQ ID NO 67
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 67
tgaaggtcaa gatgactgat ctagctgtag tggatgactt cttagcagtc tctcctatgt    60
tcgacag                                                              67

<210> SEQ ID NO 68
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 68
tctagcacaa aggacatgat tgaaggttag gacttcactt tgaaggtgtc ctagctgtgt    60
gacttca                                                              67

<210> SEQ ID NO 69
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 69
aggacatcaa aggacatgat gatgacttag tgctccactt cttagcagtc tgctccatgt    60
tggatga                                                              67

<210> SEQ ID NO 70
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 70
gatgactcaa ctagctggat ctgctgatag tctagcactt tctcctagtc gatgacttgt     60
ctgtgca                                                               67

<210> SEQ ID NO 71
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 71
cttagcacaa tggatgagat cttagcatag tgaaggtctt ctagctggtc gacttcatgt     60
caggtgt                                                               67

<210> SEQ ID NO 72
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 72
tctagcacaa gatgactgat gatgacttag tctagcactt ctgtgcagtc tgctccatgt     60
tctagca                                                               67

<210> SEQ ID NO 73
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 73
gacttcacaa ctgctgagat tgaaggttag tggatgactt tggatgagtc tggatgatgt     60
ttcgagt                                                               67

<210> SEQ ID NO 74
<211> LENGTH: 67
<212> TYPE: DNA
<213> ORGANISM: Artificial Sequence
<220> FEATURE:
<223> OTHER INFORMATION: DNA sequences selected by screening LRH-1 in
      the stapled peptide library according to Example 1

<400> SEQUENCE: 74
ttcgagtcaa tcgacaggat cttagcatag gatgactctt aggacatgtc ctgctgatgt     60
cttagca                                                               67

<210> SEQ ID NO 75
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nle.

```
<220> FEATURE:
<221> NAME/KEY: SITE
<222> LOCATION: (4)
<223> OTHER INFORMATION: The Xaa at position 4 can be Nle.
<220> FEATURE:
<221> NAME/KEY: SITE
<222> LOCATION: (6)
<223> OTHER INFORMATION: The Xaa at position 6 can be Phe-Cl, wherein
      the Phe-Cl can be 4-Chloro-phenylalanine.

<400> SEQUENCE: 75

Ser Xaa Arg Xaa Ser Xaa
1               5

<210> SEQ ID NO 76
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (1)
<223> OTHER INFORMATION: The Xaa at position 1 can be Nap, wherein the
      Nap can be 1-Naphthylalanine.
<220> FEATURE:
<221> NAME/KEY: SITE
<222> LOCATION: (3)
<223> OTHER INFORMATION: The Xaa at position 3 can be hArg, wherein the
      hArg can be Homoarginine.

<400> SEQUENCE: 76

Xaa Ile Xaa Leu Arg Phe
1               5

<210> SEQ ID NO 77
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (4)
<223> OTHER INFORMATION: The Xaa at position 4 can be Phe-Cl, wherein
      the Phe-Cl can be 4-Chloro-phenylalanine.
<220> FEATURE:
<221> NAME/KEY: SITE
<222> LOCATION: (6)
<223> OTHER INFORMATION: The Xaa at position 6 can be Nap, wherein the
      Nap can be 1-Naphthylalanine.

<400> SEQUENCE: 77

Gln Val Arg Xaa Arg Xaa
1               5

<210> SEQ ID NO 78
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nle.
<220> FEATURE:
<221> NAME/KEY: SITE
<222> LOCATION: (4)
<223> OTHER INFORMATION: The Xaa at position 4 can be Cha, wherein the
```

```
      Cha can be Cyclohexylalanine.
<220> FEATURE:
<221> NAME/KEY: SITE
<222> LOCATION: (5)
<223> OTHER INFORMATION: The Xaa at position 5 can be hArg, wherein the
      hArg can be Homoarginine.

<400> SEQUENCE: 78

Tyr Xaa Arg Xaa Xaa Trp
1               5

<210> SEQ ID NO 79
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (1)
<223> OTHER INFORMATION: The Xaa at position 1 can be Nap, wherein the
      Nap can be 1-Naphthylalanine.
<220> FEATURE:
<221> NAME/KEY: SITE
<222> LOCATION: (3)
<223> OTHER INFORMATION: The Xaa at position 3 can be Nap, wherein the
      Nap can be 1-Naphthylalanine.

<400> SEQUENCE: 79

Xaa Leu Xaa Ile Trp Trp
1               5

<210> SEQ ID NO 80
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nle.
<220> FEATURE:
<221> NAME/KEY: SITE
<222> LOCATION: (3)
<223> OTHER INFORMATION: The Xaa at position 3 can be Phe-NO2,wherein
      the Phe-NO2 can be 4-Nitro-phenylalanine.
<220> FEATURE:
<221> NAME/KEY: SITE
<222> LOCATION: (4)
<223> OTHER INFORMATION: The Xaa at position 4 can be Phe-Cl,wherein the
      Phe-Cl can be 4-Chloro-phenyalani

<400> SEQUENCE: 80

Trp Xaa Xaa Xaa Ala Ile
1               5

<210> SEQ ID NO 81
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nap, wherein the
      Nap can be 1-Naphthylalanine.

<400> SEQUENCE: 81
```

```
Gln Xaa Trp Val Arg Leu
1               5
```

<210> SEQ ID NO 82
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (1)
<223> OTHER INFORMATION: The Xaa at position 1 can be Aib.
<220> FEATURE:
<221> NAME/KEY: SITE
<222> LOCATION: (3)
<223> OTHER INFORMATION: The Xaa at position 3 can be Phe-NO2, wherein
      the Phe-NO2 can be 4-Nitro-phenylalanine.
<220> FEATURE:
<221> NAME/KEY: SITE
<222> LOCATION: (6)
<223> OTHER INFORMATION: The Xaa at position 6 can be Nle.

<400> SEQUENCE: 82

```
Xaa Ile Xaa Ile Arg Xaa
1               5
```

<210> SEQ ID NO 83
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (3)
<223> OTHER INFORMATION: The Xaa at position 3 can be hArg, wherein the
      hArg can be Homoarginine.
<220> FEATURE:
<221> NAME/KEY: SITE
<222> LOCATION: (4)
<223> OTHER INFORMATION: The Xaa at position 4 can be Nle.
<220> FEATURE:
<221> NAME/KEY: SITE
<222> LOCATION: (5)
<223> OTHER INFORMATION: The Xaa at position 5 can be hArg, wherein the
      hArg can be Homoarginine.
<220> FEATURE:
<221> NAME/KEY: SITE
<222> LOCATION: (6)
<223> OTHER INFORMATION: The Xaa at position 6 can be hArg, wherein the
      hArg can be Homoarginine.

<400> SEQUENCE: 83

```
Ser Phe Xaa Xaa Xaa Xaa
1               5
```

<210> SEQ ID NO 84
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (3)
<223> OTHER INFORMATION: The Xaa at position 3 can be hPhe, wherein the
      hPhe can be Homophenylalanine.

<400> SEQUENCE: 84

```
Arg Tyr Xaa Tyr Trp Phe
1               5

<210> SEQ ID NO 85
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.

<400> SEQUENCE: 85

Tyr Val Arg Tyr Arg Thr
1               5

<210> SEQ ID NO 86
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (1)
<223> OTHER INFORMATION: The Xaa at position 1 can be Aib.
<220> FEATURE:
<221> NAME/KEY: SITE
<222> LOCATION: (2)
<223> OTHER INFORMATION: The Xaa at position 2 can be Nle.

<400> SEQUENCE: 86

Xaa Xaa Arg Tyr Ser Gln
1               5

<210> SEQ ID NO 87
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (1)
<223> OTHER INFORMATION: The Xaa at position 1 can be Nap, wherein the
      Nap can be 1-Naphthylalanine.
<220> FEATURE:
<221> NAME/KEY: SITE
<222> LOCATION: (2)
<223> OTHER INFORMATION: The Xaa at position 2 can be Cha, wherein the
      Cha can be Cyclohexylalanine.
<220> FEATURE:
<221> NAME/KEY: SITE
<222> LOCATION: (4)
<223> OTHER INFORMATION: The Xaa at position 4 can be Nap, wherein the
      Nap can be 1-Naphthylalanine.

<400> SEQUENCE: 87

Xaa Xaa Arg Xaa Arg Phe
1               5

<210> SEQ ID NO 88
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
```

```
<222> LOCATION: (1)
<223> OTHER INFORMATION: The Xaa at position 1 can be Aib.
<220> FEATURE:
<221> NAME/KEY: SITE
<222> LOCATION: (4)
<223> OTHER INFORMATION: The Xaa at position 4 can be Phe-Cl, wherein
      Phe-Cl can be 4-Chloro-phenylalanine.
<220> FEATURE:
<221> NAME/KEY: SITE
<222> LOCATION: (5)
<223> OTHER INFORMATION: The Xaa at position 5 can be Nap, wherein the
      Nap can be 1-Naphthylalanine.
<220> FEATURE:
<221> NAME/KEY: SITE
<222> LOCATION: (6)
<223> OTHER INFORMATION: The Xaa at position 6 can be hArg, wherein the
      hArg can be Homoarginine.

<400> SEQUENCE: 88

Xaa Tyr Tyr Xaa Xaa Xaa
1               5

<210> SEQ ID NO 89
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (1)
<223> OTHER INFORMATION: The Xaa at position 1 can be Aib.
<220> FEATURE:
<221> NAME/KEY: SITE
<222> LOCATION: (2)
<223> OTHER INFORMATION: The Xaa at position 2 can be Nap, wherein the
      Nap can be 1-Naphthylalanine.
<220> FEATURE:
<221> NAME/KEY: SITE
<222> LOCATION: (5)
<223> OTHER INFORMATION: The Xaa at position 5 can be Nle.
<220> FEATURE:
<221> NAME/KEY: SITE
<222> LOCATION: (6)
<223> OTHER INFORMATION: The Xaa at position 6 can be Cha, wherein the
      Cha can be Cyclohexylalanine.

<400> SEQUENCE: 89

Xaa Xaa Phe Leu Xaa Xaa
1               5

<210> SEQ ID NO 90
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (3)
<223> OTHER INFORMATION: The Xaa at position 3 can be hArg, wherein the
      hArg can be Homoarginine.

<400> SEQUENCE: 90

Gln Ile Xaa Ile Ala Trp
1               5

<210> SEQ ID NO 91
<211> LENGTH: 6
<212> TYPE: PRT
<213> ORGANISM: Artificial Sequence
```

```
<220> FEATURE:
<223> OTHER INFORMATION: Decoded sequences of the peptide bound to the
      LRH-1 protein.
<220> FEATURE:
<221> NAME/KEY: SITE
<222> LOCATION: (1)
<223> OTHER INFORMATION: The Xaa at position 1 can be Cha, wherein the
      Cha can be Cyclohexylalanine.
<220> FEATURE:
<221> NAME/KEY: SITE
<222> LOCATION: (2)
<223> OTHER INFORMATION: The Xaa at position 2 can be Phe-Cl, wherein
      the Phe-Cl can be 4-Chloro-phenylalanine.
<220> FEATURE:
<221> NAME/KEY: SITE
<222> LOCATION: (3)
<223> OTHER INFORMATION: The Xaa at position 3 can be hArg, wherein hArg
      can be Homoarginine.
<220> FEATURE:
<221> NAME/KEY: SITE
<222> LOCATION: (4)
<223> OTHER INFORMATION: The Xaa at position 4 can be Phe-Cl, wherein
      the Phe-Cl can be 4-Chloro-phenylalanine.
<220> FEATURE:
<221> NAME/KEY: SITE
<222> LOCATION: (6)
<223> OTHER INFORMATION: The Xaa at position 6 can be Aib

<400> SEQUENCE: 91

Xaa Xaa Xaa Xaa Gln Xaa
1               5

<210> SEQ ID NO 92
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (3)
<223> OTHER INFORMATION: The Xaa at position 3 can be Nap, wherein the
      Nap can be 1-Naphthylalanine.
<220> FEATURE:
<221> NAME/KEY: SITE
<222> LOCATION: (5)
<223> OTHER INFORMATION: The Xaa at position 5 can be Nap, wherein the
      Nap can be 1-Naphthylalanine.
<220> FEATURE:
<221> NAME/KEY: SITE
<222> LOCATION: (6)
<223> OTHER INFORMATION: The Xaa at position 6 can be Cha, wherein the
      Cha can be Cyclohexylalanine.

<400> SEQUENCE: 92

Ile Val Xaa Leu Xaa Xaa
1               5

<210> SEQ ID NO 93
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (5)
<223> OTHER INFORMATION: The Xaa at position 5 can be Nle.
<220> FEATURE:
<221> NAME/KEY: SITE
<222> LOCATION: (6)
<223> OTHER INFORMATION: The Xaa at position 6 can be hArg, wherein the
      hArg can be Homoarginine.
```

<400> SEQUENCE: 93

Arg Leu Phe Phe Xaa Xaa
1               5

<210> SEQ ID NO 94
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (3)
<223> OTHER INFORMATION: The Xaa at position 3 can be Phe-F, wherein the
      Phe-F can be 4-Fluoro-phenylalanine.

<400> SEQUENCE: 94

Ser Leu Xaa Leu Trp Phe
1               5

<210> SEQ ID NO 95
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Cha, wherein the
      Cha can be Cyclohexylalanine.
<220> FEATURE:
<221> NAME/KEY: SITE
<222> LOCATION: (4)
<223> OTHER INFORMATION: The Xaa at position 4 can be Cha, wherein the
      Cha can be Cyclohexylalanine.
<220> FEATURE:
<221> NAME/KEY: SITE
<222> LOCATION: (5)
<223> OTHER INFORMATION: The Xaa at position 5 can be Nap, wherein the
      Nap can be 1-Naphthylalanine.
<220> FEATURE:
<221> NAME/KEY: SITE
<222> LOCATION: (6)
<223> OTHER INFORMATION: The Xaa at position 6 can be Phe-Cl, wherein
      the Phe-Cl can be 4-Chloro-phenylalanine.

<400> SEQUENCE: 95

Tyr Xaa Tyr Xaa Xaa Xaa
1               5

<210> SEQ ID NO 96
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nle.
<220> FEATURE:
<221> NAME/KEY: SITE
<222> LOCATION: (3)
<223> OTHER INFORMATION: The Xaa at position 3 can be Phe-NO2, wherein
      the Phe-NO2 can be 4-Nitro-phenylalanine.

<400> SEQUENCE: 96

```
Ser Xaa Xaa Val Ser Leu
1               5
```

<210> SEQ ID NO 97
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.

<400> SEQUENCE: 97

```
Ile Tyr Arg Leu Ala Thr
1               5
```

<210> SEQ ID NO 98
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (3)
<223> OTHER INFORMATION: The Xaa at position 3 can be Phe-F, wherein the
      Phe-F can be 4-Fluoro-phenylalanine.

<400> SEQUENCE: 98

```
Phe Tyr Xaa Ile Ala Thr
1               5
```

<210> SEQ ID NO 99
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (1)
<223> OTHER INFORMATION: The Xaa at position 1 can be Cha, wherenin the
      Cha can be Cyclohexylalanine.
<220> FEATURE:
<221> NAME/KEY: SITE
<222> LOCATION: (2)
<223> OTHER INFORMATION: he Xaa at position 2 can be Phe-Cl, wherein the
      Phe-Cl can be 4-Chloro-phenylalanine.
<220> FEATURE:
<221> NAME/KEY: SITE
<222> LOCATION: (4)
<223> OTHER INFORMATION: The Xaa at position 4 can be Phe-F, wherein the
      Phe-F can be 4-Fluoro-phenylalanine.
<220> FEATURE:
<221> NAME/KEY: SITE
<222> LOCATION: (6)
<223> OTHER INFORMATION: The Xaa at position 6 can be Cha, wherenin the
      Cha can be Cyclohexylalanine.

<400> SEQUENCE: 99

```
Xaa Xaa Arg Xaa Phe Xaa
1               5
```

<210> SEQ ID NO 100
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:

```
<221> NAME/KEY: SITE
<222> LOCATION: (5)
<223> OTHER INFORMATION: The Xaa at position 5 can be Nle.
<220> FEATURE:
<221> NAME/KEY: SITE
<222> LOCATION: (6)
<223> OTHER INFORMATION: The Xaa at position 6 can be Aib.

<400> SEQUENCE: 100

Leu Leu Phe Ile Xaa Xaa
1               5

<210> SEQ ID NO 101
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (3)
<223> OTHER INFORMATION: The Xaa at position 3 can be hPhe, wherein the
      hPhe can be Homophenylalanine.
<220> FEATURE:
<221> NAME/KEY: SITE
<222> LOCATION: (6)
<223> OTHER INFORMATION: The Xaa at position 6 can be Aib.

<400> SEQUENCE: 101

Ser Tyr Xaa Tyr Leu Xaa
1               5

<210> SEQ ID NO 102
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (1)
<223> OTHER INFORMATION: The Xaa at position 1 can be hArg, wherein the
      hArg can be Homoarginine.
<220> FEATURE:
<221> NAME/KEY: SITE
<222> LOCATION: (2)
<223> OTHER INFORMATION: The Xaa at position 2 can be Nle.
<220> FEATURE:
<221> NAME/KEY: SITE
<222> LOCATION: (5)
<223> OTHER INFORMATION: The Xaa at position 5 can be hArg, wherein the
      hArg can be Homoarginine.
<220> FEATURE:
<221> NAME/KEY: SITE
<222> LOCATION: (6)
<223> OTHER INFORMATION: The Xaa at position 6 can be hArg, wherein the
      hArg can be Homoarginine.

<400> SEQUENCE: 102

Xaa Xaa Arg Tyr Xaa Xaa
1               5

<210> SEQ ID NO 103
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
```

```
<222> LOCATION: (2)
<223> OTHER INFORMATION: The Xaa at position 2 can be Phe-F, wherein the
      Phe-F can be 4-Fluoro-phenylalanine.
<220> FEATURE:
<221> NAME/KEY: SITE
<222> LOCATION: (3)
<223> OTHER INFORMATION: The Xaa at position 3 can be Nap, wherein the
      Nap can be 1-Naphthylalanine.

<400> SEQUENCE: 103

Trp Xaa Xaa Trp Ala Trp
1               5

<210> SEQ ID NO 104
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (1)
<223> OTHER INFORMATION: The Xaa at position 1 can be Aib.
<220> FEATURE:
<221> NAME/KEY: SITE
<222> LOCATION: (2)
<223> OTHER INFORMATION: The Xaa at position 2 can be Nap, wherein the
      Nap can be 1-Naphthylalanine.
<220> FEATURE:
<221> NAME/KEY: SITE
<222> LOCATION: (4)
<223> OTHER INFORMATION: The Xaa at position 4 can be hPhe, wherein the
      hPhe can be Homophenylalanine.

<400> SEQUENCE: 104

Xaa Xaa Arg Xaa Leu Trp
1               5

<210> SEQ ID NO 105
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nle.
<220> FEATURE:
<221> NAME/KEY: SITE
<222> LOCATION: (4)
<223> OTHER INFORMATION: The Xaa at position 4 can be Nle.
<220> FEATURE:
<221> NAME/KEY: SITE
<222> LOCATION: (6)
<223> OTHER INFORMATION: The Xaa at position 6 can be hArg, wherein the
      hArg can be Homoarginine.

<400> SEQUENCE: 105

Tyr Xaa Arg Xaa Trp Xaa
1               5

<210> SEQ ID NO 106
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
```

```
<222> LOCATION: (1)
<223> OTHER INFORMATION: The Xaa at position 1 can be hArg, wherenin the
      hArg can be Homoarginine.
<220> FEATURE:
<221> NAME/KEY: SITE
<222> LOCATION: (3)
<223> OTHER INFORMATION: The Xaa at position 3 can be Phe-Cl, whereni
      the Phe-Cl can be 4-Chloro-phenylalanine.
<220> FEATURE:
<221> NAME/KEY: SITE
<222> LOCATION: (4)
<223> OTHER INFORMATION: The Xaa at position 4 can be hPhe, wherein the
      hPhe can be Homophenylalanine.
<220> FEATURE:
<221> NAME/KEY: SITE
<222> LOCATION: (6)
<223> OTHER INFORMATION: The Xaa at position 6 can be hArg, wherenin the
      hArg can be Homoarginine.

<400> SEQUENCE: 106

Xaa Tyr Xaa Xaa Trp Xaa
1               5

<210> SEQ ID NO 107
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nle.
<220> FEATURE:
<221> NAME/KEY: SITE
<222> LOCATION: (4)
<223> OTHER INFORMATION: The Xaa at position 4 can be Phe-Cl, wherein
      the Phe-Cl can be 4-Chloro-phenylalanine.

<400> SEQUENCE: 107

Thr Xaa Trp Xaa Ser Leu
1               5

<210> SEQ ID NO 108
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (1)
<223> OTHER INFORMATION: The Xaa at position 1 can be hArg, wherenin the
      hArg can be Homoarginine.
<220> FEATURE:
<221> NAME/KEY: SITE
<222> LOCATION: (2)
<223> OTHER INFORMATION: The Xaa at position 2 can be Phe-F, wherein the
      Phe-F can be 4-Fluoro-phenylalanine.
<220> FEATURE:
<221> NAME/KEY: SITE
<222> LOCATION: (3)
<223> OTHER INFORMATION: The Xaa at position 3 can be Phe-Cl, wherein
      the Phe-Cl can be 4-Chloro-phenylalanine.
<220> FEATURE:
<221> NAME/KEY: SITE
<222> LOCATION: (4)
<223> OTHER INFORMATION: The Xaa at position 4 can be Nap, wherein the
      Nap can be 1-Naphthylalanine.
<220> FEATURE:
<221> NAME/KEY: SITE
<222> LOCATION: (6)
<223> OTHER INFORMATION: The Xaa at position 6 can be Cha, wherein the
```

Cha can be Cyclohexylalanine.

<400> SEQUENCE: 108

Xaa Xaa Xaa Xaa Ile Xaa
1               5

<210> SEQ ID NO 109
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (3)
<223> OTHER INFORMATION: The Xaa at position 3 can be Phe-F, wherein the
      Phe-F can be 4-Fluoro-phenylalanine.
<220> FEATURE:
<221> NAME/KEY: SITE
<222> LOCATION: (4)
<223> OTHER INFORMATION: The Xaa at position 4 can be Nle.
<220> FEATURE:
<221> NAME/KEY: SITE
<222> LOCATION: (5)
<223> OTHER INFORMATION: The Xaa at position 5 can be Aib.

<400> SEQUENCE: 109

Tyr Ile Xaa Xaa Xaa Ala
1               5

<210> SEQ ID NO 110
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.

<400> SEQUENCE: 110

Trp Leu Tyr Ile Ala Ser
1               5

<210> SEQ ID NO 111
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nle.
<220> FEATURE:
<221> NAME/KEY: SITE
<222> LOCATION: (3)
<223> OTHER INFORMATION: The Xaa at position 3 can be Phe-F, wherein the
      Phe-F can be 4-Fluoro-phenylalanine.
<220> FEATURE:
<221> NAME/KEY: SITE
<222> LOCATION: (4)
<223> OTHER INFORMATION: The Xaa at position 4 can be Phe-F, wherein the
      Phe-F can be 4-Fluoro-phenylalanine.
<220> FEATURE:
<221> NAME/KEY: SITE
<222> LOCATION: (6)
<223> OTHER INFORMATION: The Xaa at position 6 can be Phe-Cl, wherein the
      Phe-Cl can be 4-Chloro-phenylalanine.

<400> SEQUENCE: 111

Gln Xaa Xaa Xaa Gln Xaa

-continued

```
<210> SEQ ID NO 112
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (4)
<223> OTHER INFORMATION: The Xaa at position 4 can be Nap, wherein the
      Nap can be 1-Naphthylalanine.

<400> SEQUENCE: 112

Phe Ile Arg Xaa Ala Thr
1               5

<210> SEQ ID NO 113
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Cha, wherein the
      Cha can be Cyclohexylalanine.
<220> FEATURE:
<221> NAME/KEY: SITE
<222> LOCATION: (6)
<223> OTHER INFORMATION: The Xaa at position 6 can be hArg, wherenin the
      hArg can be Homoarginine.

<400> SEQUENCE: 113

Ser Xaa Trp Leu Ile Xaa
1               5

<210> SEQ ID NO 114
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nle.
<220> FEATURE:
<221> NAME/KEY: SITE
<222> LOCATION: (6)
<223> OTHER INFORMATION: The Xaa at position 6 can be Nle.

<400> SEQUENCE: 114

Ile Xaa Phe Leu Trp Xaa
1               5

<210> SEQ ID NO 115
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (3)
<223> OTHER INFORMATION: The Xaa at position 3 can be Nap, wherein the
```

```
      Nap can be 1-Naphthylalanine
<220> FEATURE:
<221> NAME/KEY: SITE
<222> LOCATION: (4)
<223> OTHER INFORMATION: The Xaa at position 4 can be Phe-F, wherein the
      Phe-F can be 4-Fluoro-phenylalanine.

<400> SEQUENCE: 115

Tyr Val Xaa Xaa Gly Trp
1               5

<210> SEQ ID NO 116
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be hPhe, wherein the
      hPhe can be Homophenylalanine.
<220> FEATURE:
<221> NAME/KEY: SITE
<222> LOCATION: (3)
<223> OTHER INFORMATION: The Xaa at position 3 can be hPhe, wherein the
      hPhe can be Homophenylalanine.

<400> SEQUENCE: 116

Arg Xaa Xaa Phe Trp Arg
1               5

<210> SEQ ID NO 117
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nle.
<220> FEATURE:
<221> NAME/KEY: SITE
<222> LOCATION: (4)
<223> OTHER INFORMATION: The Xaa at position 4 can be Cha, wherein the
      Cha can be Cyclohexylalanine.
<220> FEATURE:
<221> NAME/KEY: SITE
<222> LOCATION: (6)
<223> OTHER INFORMATION: The Xaa at position 6  can be Nap, wherein the
      Nap can be 1-Naphthylalanine.

<400> SEQUENCE: 117

Ile Xaa Trp Xaa Ala Xaa
1               5

<210> SEQ ID NO 118
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nle.
<220> FEATURE:
<221> NAME/KEY: SITE
<222> LOCATION: (3)
```

```
<223> OTHER INFORMATION: The Xaa at position 3 can be Nap, wherein the
      Nap can be 1-Naphthylalanine.
<220> FEATURE:
<221> NAME/KEY: SITE
<222> LOCATION: (4)
<223> OTHER INFORMATION: The Xaa at position 4 can be hPhe, wherein the
      hPhe can be Homophenylalanine.

<400> SEQUENCE: 118

Ile Xaa Xaa Xaa Ile Ala
1               5

<210> SEQ ID NO 119
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (1)
<223> OTHER INFORMATION: The Xaa at position 1 can be Aib.
<220> FEATURE:
<221> NAME/KEY: SITE
<222> LOCATION: (3)
<223> OTHER INFORMATION: The Xaa at position 3 can be Phe-Cl, wherein
      the Phe-Cl can be 4-Chloro-phenylalanine.
<220> FEATURE:
<221> NAME/KEY: SITE
<222> LOCATION: (5)
<223> OTHER INFORMATION: The Xaa at position 5 can be Aib.

<400> SEQUENCE: 119

Xaa Ile Xaa Leu Xaa Trp
1               5

<210> SEQ ID NO 120
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nle.
<220> FEATURE:
<221> NAME/KEY: SITE
<222> LOCATION: (4)
<223> OTHER INFORMATION: The Xaa at position 4 can be hPhe, wherein the
      hPhe can be Homophenylalanine.

<400> SEQUENCE: 120

Ala Xaa Tyr Xaa Phe Ser
1               5

<210> SEQ ID NO 121
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (3)
<223> OTHER INFORMATION: The Xaa at position 3 can be hPhe, wherein the
      hPhe can be Homophenylalanine.
<220> FEATURE:
<221> NAME/KEY: SITE
<222> LOCATION: (5)
```

-continued

```
<223> OTHER INFORMATION: The Xaa at position 5 can be hArg, wherein the
      hArg can be Homoarginine.
<220> FEATURE:
<221> NAME/KEY: SITE
<222> LOCATION: (6)
<223> OTHER INFORMATION: The Xaa at position 6 can be hArg, wherein the
      hArg can be Homoarginine.

<400> SEQUENCE: 121

Ile Tyr Xaa Ile Xaa Xaa
1               5

<210> SEQ ID NO 122
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Phe-Cl, wherein
      the Phe-Cl can be 4-Chloro-phenylalanine.
<220> FEATURE:
<221> NAME/KEY: SITE
<222> LOCATION: (3)
<223> OTHER INFORMATION: The Xaa at position 3 can be Phe-NO2, wherein
      the Phe-NO2 can be 4-Nitro-phenylalanine.
<220> FEATURE:
<221> NAME/KEY: SITE
<222> LOCATION: (5)
<223> OTHER INFORMATION: The Xaa at position 5 can be Cha, wherein the
      Cha can be Cyclohexylalanine.

<400> SEQUENCE: 122

Arg Xaa Xaa Ile Xaa Gln
1               5

<210> SEQ ID NO 123
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (4)
<223> OTHER INFORMATION: The Xaa at position 4 can be Phe-Cl, wherein
      the Phe-Cl can be 4-Chloro-phenylalanine
<220> FEATURE:
<221> NAME/KEY: SITE
<222> LOCATION: (6)
<223> OTHER INFORMATION: The Xaa at position 6 can be Nle.

<400> SEQUENCE: 123

Arg Val Tyr Xaa Arg Xaa
1               5

<210> SEQ ID NO 124
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Phe-F, wherein the
      Phe-F can be 4-Fluoro-phenylalanine.
<220> FEATURE:
```

```
<221> NAME/KEY: SITE
<222> LOCATION: (3)
<223> OTHER INFORMATION: The Xaa at position 3 can be Phe-Cl, wherein
      the Phe-Cl can be 4-Chloro-phenylalanine.
<220> FEATURE:
<221> NAME/KEY: SITE
<222> LOCATION: (6)
<223> OTHER INFORMATION: The Xaa at position 6 can be hArg, wherenin the
      hArg can be Homoarginine.

<400> SEQUENCE: 124

Ala Xaa Xaa Ile Ser Xaa
1               5

<210> SEQ ID NO 125
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (4)
<223> OTHER INFORMATION: The Xaa at position 4 can be Phe-F, wherein the
      Phe-F can be 4-Fluoro-phenylalanine.
<220> FEATURE:
<221> NAME/KEY: SITE
<222> LOCATION: (6)
<223> OTHER INFORMATION: The Xaa at position 6 can be Phe-Cl, wherein
      the Phe-Cl can be 4-Chloro-phenylalanine.

<400> SEQUENCE: 125

Trp Tyr Phe Xaa Thr Xaa
1               5

<210> SEQ ID NO 126
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (1)
<223> OTHER INFORMATION: The Xaa at position 1 can be Aib.
<220> FEATURE:
<221> NAME/KEY: SITE
<222> LOCATION: (4)
<223> OTHER INFORMATION: The Xaa at position 4 can be Nle.
<220> FEATURE:
<221> NAME/KEY: SITE
<222> LOCATION: (5)
<223> OTHER INFORMATION: The Xaa at position 5 can be Nle.
<220> FEATURE:
<221> NAME/KEY: SITE
<222> LOCATION: (6)
<223> OTHER INFORMATION: The Xaa at position 6 can be hArg, wherenin the
      hArg can be Homoarginine.

<400> SEQUENCE: 126

Xaa Trp Tyr Xaa Xaa Xaa
1               5

<210> SEQ ID NO 127
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
```

```
<221> NAME/KEY: SITE
<222> LOCATION: (3)
<223> OTHER INFORMATION: The Xaa at position 3 can be hArg, wherenin the
      hArg can be Homoarginine.
<220> FEATURE:
<221> NAME/KEY: SITE
<222> LOCATION: (6)
<223> OTHER INFORMATION: The Xaa at position 6 can be hArg, wherenin the
      hArg can be Homoarginine.

<400> SEQUENCE: 127

Tyr Ile Xaa Tyr Ala Xaa
1               5

<210> SEQ ID NO 128
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nle.
<220> FEATURE:
<221> NAME/KEY: SITE
<222> LOCATION: (4)
<223> OTHER INFORMATION: The Xaa at position 4 can be Phe-F, wherein the
      Phe-F can be 4-Fluoro-phenylalanine.

<400> SEQUENCE: 128

Phe Xaa Arg Xaa Gln Trp
1               5

<210> SEQ ID NO 129
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nle.
<220> FEATURE:
<221> NAME/KEY: SITE
<222> LOCATION: (6)
<223> OTHER INFORMATION: The Xaa at position 6 can be Nle.

<400> SEQUENCE: 129

Ser Xaa Trp Trp Ala Xaa
1               5

<210> SEQ ID NO 130
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Nap, wherein the
      Nap can be 1-Naphthylalanine.
<220> FEATURE:
<221> NAME/KEY: SITE
<222> LOCATION: (3)
<223> OTHER INFORMATION: The Xaa at position 3 can be Phe-NO2, wherein
      the Phe-NO2 can be 4-Nitro-phenylalanine.
<220> FEATURE:
```

```
<221> NAME/KEY: SITE
<222> LOCATION: (5)
<223> OTHER INFORMATION: The Xaa at position 5 can be Nap, wherein the
      Nap can be 1-Naphthylalanine.

<400> SEQUENCE: 130

Ile Xaa Xaa Phe Xaa Ile
1               5

<210> SEQ ID NO 131
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (4)
<223> OTHER INFORMATION: The Xaa at position 4 can be Phe-Cl, wherein
      the Phe-Cl can be 4-Chloro-phenylalanine.

<400> SEQUENCE: 131

Leu Tyr Tyr Xaa Tyr Gln
1               5

<210> SEQ ID NO 132
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (5)
<223> OTHER INFORMATION: The Xaa at position 5 can be hArg, wherenin the
      hArg can be Homoarginine.
<220> FEATURE:
<221> NAME/KEY: SITE
<222> LOCATION: (6)
<223> OTHER INFORMATION: The Xaa at position 6 can be Nle.

<400> SEQUENCE: 132

Phe Ile Trp Phe Xaa Xaa
1               5

<210> SEQ ID NO 133
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
<220> FEATURE:
<221> NAME/KEY: SITE
<222> LOCATION: (2)
<223> OTHER INFORMATION: The Xaa at position 2 can be Cha, wherein the
      Cha can be Cyclohexylalanine.

<400> SEQUENCE: 133

Gln Xaa Arg Tyr Trp Arg
1               5

<210> SEQ ID NO 134
<211> LENGTH: 6
<212> TYPE: PRT
<213> ORGANISM: Artificial Sequence
<220> FEATURE:
<223> OTHER INFORMATION: Decoded sequences of the peptide bound to the
      LRH-1 protein.
```

```
<220> FEATURE:
<221> NAME/KEY: SITE
<222> LOCATION: (1)
<223> OTHER INFORMATION: The Xaa at position 1 can be Nap, wherein the
      Nap can be 1-Naphthylalanine.

<400> SEQUENCE: 134

Xaa Val Tyr Ile Phe Thr
1               5

<210> SEQ ID NO 135
<211> LENGTH: 74
<212> TYPE: DNA
<213> ORGANISM: Artificial Sequence
<220> FEATURE:
<223> OTHER INFORMATION: DNA sequences selected by screening PTP1B in
      the peptoid library according to Example 2

<400> SEQUENCE: 135
tctctgaagg tcaactgctg agatctagcc gtagcaggtg tctttggatg agtctgaagg      60
ttgtctgtgc aacc                                                       74

<210> SEQ ID NO 136
<211> LENGTH: 74
<212> TYPE: DNA
<213> ORGANISM: Artificial Sequence
<220> FEATURE:
<223> OTHER INFORMATION: DNA sequences selected by screening PTP1B in
      the peptoid library according to Example 2

<400> SEQUENCE: 136
tctcctgctg acaactgctg agattctcct atagctgctg actttgaagg tgtcttcgag      60
ttgtcaggtg tacc                                                       74

<210> SEQ ID NO 137
<211> LENGTH: 74
<212> TYPE: DNA
<213> ORGANISM: Artificial Sequence
<220> FEATURE:
<223> OTHER INFORMATION: DNA sequences selected by screening PTP1B in
      the peptoid library according to Example 2

<400> SEQUENCE: 137
tctctggatg acaagacttc agataggaca ttagttcgag tctttgctcc agtctctagc      60
atgttggatg aacc                                                       74

<210> SEQ ID NO 138
<211> LENGTH: 74
<212> TYPE: DNA
<213> ORGANISM: Artificial Sequence
<220> FEATURE:
<223> OTHER INFORMATION: DNA sequences selected by screening PTP1B in
      the peptoid library according to Example 2

<400> SEQUENCE: 138
tctccttagc acaactgtgc agataggaca ttagcaggtg tctttcgaca ggtcctgctg      60
atgtcaggtg tacc                                                       74

<210> SEQ ID NO 139
<211> LENGTH: 74
<212> TYPE: DNA
<213> ORGANISM: Artificial Sequence
<220> FEATURE:
<223> OTHER INFORMATION: DNA sequences selected by screening PTP1B in
      the peptoid library according to Example 2
```

```
<400> SEQUENCE: 139
tctctctagc acaacttagc agataggaca ttagcaactg tcttcttagc agtcttcgag      60
ttgtctagct gacc                                                       74

<210> SEQ ID NO 140
<211> LENGTH: 74
<212> TYPE: DNA
<213> ORGANISM: Artificial Sequence
<220> FEATURE:
<223> OTHER INFORMATION: DNA sequences selected by screening PTP1B in
      the peptoid library according to Example 2

<400> SEQUENCE: 140
tctcctgctg acaatcgaca ggattggatg atagtggatg actttctcct agtctctagc      60
atgtttcgag tacc                                                       74

<210> SEQ ID NO 141
<211> LENGTH: 74
<212> TYPE: DNA
<213> ORGANISM: Artificial Sequence
<220> FEATURE:
<223> OTHER INFORMATION: DNA sequences selected by screening PTP1B in
      the peptoid library according to Example 2

<400> SEQUENCE: 141
tctcctgctg acaagacttc agatctgtgc atagctagct gctttggatt agtctggatg      60
atgtgacttc aacc                                                       74

<210> SEQ ID NO 142
<211> LENGTH: 74
<212> TYPE: DNA
<213> ORGANISM: Artificial Sequence
<220> FEATURE:
<223> OTHER INFORMATION: DNA sequences selected by screening PTP1B in
      the peptoid library according to Example 2

<400> SEQUENCE: 142
tctccaactg tcaatcgaca ggatttcgag ttagctgctg actttctagc agtctgctcc      60
atgtgatgac tacc                                                       74

<210> SEQ ID NO 143
<211> LENGTH: 74
<212> TYPE: DNA
<213> ORGANISM: Artificial Sequence
<220> FEATURE:
<223> OTHER INFORMATION: DNA sequences selected by screening PTP1B in
      the peptoid library according to Example 2

<400> SEQUENCE: 143
tctcctgctg acaactgctg agattctcct atagctgctg actttgaagg tgtcttcgag      60
ttgccaggtg tacc                                                       74

<210> SEQ ID NO 144
<211> LENGTH: 74
<212> TYPE: DNA
<213> ORGANISM: Artificial Sequence
<220> FEATURE:
<223> OTHER INFORMATION: DNA sequences selected by screening PTP1B in
      the peptoid library according to Example 2

<400> SEQUENCE: 144
tctcctagct gcaaaggaca tgattctagc atagctagct gcttcaactg tgtcgacttc      60
```
atgtctgtgc aacc                                             74

<210> SEQ ID NO 145
<211> LENGTH: 47
<212> TYPE: DNA
<213> ORGANISM: Artificial Sequence
<220> FEATURE:
<223> OTHER INFORMATION: DNA sequences selected by screening Bcl-xL in
      an alpha-helix analogue library having the triazine-piperazine-
      triazine backbone according to Example 3

<400> SEQUENCE: 145
tctcctacaa tcgacaggat tgctccatag caactgtctt ctagctg          47

<210> SEQ ID NO 146
<211> LENGTH: 47
<212> TYPE: DNA
<213> ORGANISM: Artificial Sequence
<220> FEATURE:
<223> OTHER INFORMATION: DNA sequences selected by screening Bcl-xL in
      an alpha-helix analogue library having the triazine-piperazine-
      triazine backbone according to Example 3

<400> SEQUENCE: 146
tggatgacaa ctgtgcagat gacttcatag cttagcactt caactgt          47

<210> SEQ ID NO 147
<211> LENGTH: 47
<212> TYPE: DNA
<213> ORGANISM: Artificial Sequence
<220> FEATURE:
<223> OTHER INFORMATION: DNA sequences selected by screening Bcl-xL in
      an alpha-helix analogue library having the triazine-piperazine-
      triazine backbone according to Example 3

<400> SEQUENCE: 147
gatgactcaa cttagcagat ctgctgatag caactgtctt tctccta          47

<210> SEQ ID NO 148
<211> LENGTH: 47
<212> TYPE: DNA
<213> ORGANISM: Artificial Sequence
<220> FEATURE:
<223> OTHER INFORMATION: DNA sequences selected by screening Bcl-xL in
      an alpha-helix analogue library having the triazine-piperazine-
      triazine backbone according to Example 3

<400> SEQUENCE: 148
caactgtcaa aggacatgat tctagcatag tctcctactt caggtgt          47

<210> SEQ ID NO 149
<211> LENGTH: 47
<212> TYPE: DNA
<213> ORGANISM: Artificial Sequence
<220> FEATURE:
<223> OTHER INFORMATION: DNA sequences selected by screening Bcl-xL in
      an alpha-helix analogue library having the triazine-piperazine-
      triazine backbone according to Example 3

<400> SEQUENCE: 149
tggatgacaa cttagcagat ctgctgatag caactgtctt tctccta          47

<210> SEQ ID NO 150
<211> LENGTH: 47
<212> TYPE: DNA
<213> ORGANISM: Artificial Sequence
<220> FEATURE:

<223> OTHER INFORMATION: DNA sequences selected by screening Bcl-xL in
      an alpha-helix analogue library having the triazine-piperazine-
      triazine backbone according to Example 3

<400> SEQUENCE: 150
tgaaggtcaa ttcgagtgat tgaaggttag ttcgagtctt tcgacag                47

<210> SEQ ID NO 151
<211> LENGTH: 47
<212> TYPE: DNA
<213> ORGANISM: Artificial Sequence
<220> FEATURE:
<223> OTHER INFORMATION: DNA sequences selected by screening Bcl-xL in
      an alpha-helix analogue library having the triazine-piperazine-
      triazine backbone according to Example 3

<400> SEQUENCE: 151
cttagcacaa tgaaggtgat cttagcatag tctcctactt aggacat                47

<210> SEQ ID NO 152
<211> LENGTH: 47
<212> TYPE: DNA
<213> ORGANISM: Artificial Sequence
<220> FEATURE:
<223> OTHER INFORMATION: DNA sequences selected by screening Bcl-xL in
      an alpha-helix analogue library having the triazine-piperazine-
      triazine backbone according to Example 3

<400> SEQUENCE: 152
tctcctacaa tgaaggtgat tggatgatag tctagcactt ctgtgca                47

<210> SEQ ID NO 153
<211> LENGTH: 47
<212> TYPE: DNA
<213> ORGANISM: Artificial Sequence
<220> FEATURE:
<223> OTHER INFORMATION: DNA sequences selected by screening Bcl-xL in
      an alpha-helix analogue library having the triazine-piperazine-
      triazine backbone according to Example 3

<400> SEQUENCE: 153
caactgtcaa ctgtgcagat tgaaggttag caactgtctt ctgtgca                47

<210> SEQ ID NO 154
<211> LENGTH: 47
<212> TYPE: DNA
<213> ORGANISM: Artificial Sequence
<220> FEATURE:
<223> OTHER INFORMATION: DNA sequences selected by screening Bcl-xL in
      an alpha-helix analogue library having the triazine-piperazine-
      triazine backbone according to Example 3

<400> SEQUENCE: 154
cttagcacaa ctgtgcagat tgctccatag caactgtctt ctgtgca                47

<210> SEQ ID NO 155
<211> LENGTH: 24
<212> TYPE: DNA
<213> ORGANISM: Artificial Sequence
<220> FEATURE:
<223> OTHER INFORMATION: forward primer to amplify a DNA sequence
      encoding a probe

<400> SEQUENCE: 155
tagaaggcac agtcgaggca tctc                                         24

<210> SEQ ID NO 156

```
<211> LENGTH: 26
<212> TYPE: DNA
<213> ORGANISM: Artificial Sequence
<220> FEATURE:
<223> OTHER INFORMATION: reverse primer to amplify a DNA sequence
      encoding a probe

<400> SEQUENCE: 156
ggtcagcata gctgtctcct gatcag                                          26

<210> SEQ ID NO 157
<211> LENGTH: 24
<212> TYPE: DNA
<213> ORGANISM: Artificial Sequence
<220> FEATURE:
<223> OTHER INFORMATION: forward primer to amplify a DNA sequence
      encoding a probe

<400> SEQUENCE: 157
tagaaggcac agtcgaggca tctc                                            24

<210> SEQ ID NO 158
<211> LENGTH: 26
<212> TYPE: DNA
<213> ORGANISM: Artificial Sequence
<220> FEATURE:
<223> OTHER INFORMATION: reverse primer to amplify a DNA sequence
      encoding a probe

<400> SEQUENCE: 158
ggtcagcata gctgtctcct gatcag                                          26

<210> SEQ ID NO 159
<211> LENGTH: 24
<212> TYPE: DNA
<213> ORGANISM: Artificial Sequence
<220> FEATURE:
<223> OTHER INFORMATION: forward primer to amplify a DNA sequence
      encoding a probe

<400> SEQUENCE: 159
tagaaggcac agtcgaggca tctc                                            24

<210> SEQ ID NO 160
<211> LENGTH: 30
<212> TYPE: DNA
<213> ORGANISM: Artificial Sequence
<220> FEATURE:
<223> OTHER INFORMATION: reverse primer to amplify a DNA sequence
      encoding a probe

<400> SEQUENCE: 160
caggcagtca cgtccagtta cactatgagg                                      30
```